United States Patent [19]

Christensen et al.

[11] 4,226,866
[45] Oct. 7, 1980

[54] NOVEL ANTIBIOTIC ANALOGUES OF CEPHALOSPORINS

[75] Inventors: Burton G. Christensen, Scotch Plains; Ronald W. Ratcliffe, North Plainfield, both of N.J.

[73] Assignee: Merck & Co., Inc., Rahway, N.J.

[21] Appl. No.: 47,593

[22] Filed: Jun. 8, 1979

Related U.S. Application Data

[63] Continuation of Ser. No. 869,199, Jan. 13, 1978, abandoned, which is a continuation of Ser. No. 587,526, Jun. 16, 1975, abandoned, which is a continuation-in-part of Ser. No. 395,662, Sep. 18, 1973, abandoned, which is a continuation-in-part of Ser. No. 303,906, Nov. 6, 1972, abandoned.

[51] Int. Cl.$^2$ ................. A61K 31/535; C07D 265/34
[52] U.S. Cl. .......................... 424/248.51; 424/248.4; 424/248.52; 424/248.53; 424/248.54; 542/422; 260/239 A; 260/941; 260/968; 260/340.7; 260/340.9 R; 260/349; 544/90; 549/5; 549/6; 549/7
[58] Field of Search .......... 544/90; 424/248.4, 248.51, 424/248.52, 248.53, 248.54

[56] References Cited

U.S. PATENT DOCUMENTS

| | | | |
|---|---|---|---|
| 3,795,672 | 3/1974 | Murphy | 544/30 |
| 3,852,277 | 12/1974 | Jacobus et al. | 424/246 |
| 3,948,927 | 4/1976 | Wolfe et al. | 260/307 FA |
| 4,011,216 | 3/1977 | Menard et al. | 544/90 |
| 4,013,648 | 3/1977 | Horning et al. | 544/90 |
| 4,013,653 | 3/1977 | Wolfe et al. | 544/90 |

FOREIGN PATENT DOCUMENTS

| | | | |
|---|---|---|---|
| 832174 | 1/1976 | Belgium | 544/90 |
| 1914366 | 10/1970 | Fed. Rep. of Germany | 544/90 |
| 2355206 | 3/1974 | Fed. Rep. of Germany | 544/90 |
| 2355209 | 3/1974 | Fed. Rep. of Germany | 544/90 |
| 2355210 | 3/1974 | Fed. Rep. of Germany | . |

OTHER PUBLICATIONS

Flynn, Cephalosporins & Penicillins, frontispage, pp. 448–449, 508–509, 521–523, 546, 548–549, 553–582 & 694, Academic Press NY (1972).
Lowy et al., An Introduction to Organic Chemistry, Frontispage & p. 213, John Wiley and Sons (6th Ed., Copyrighted 1945).
Burger, Medicinal Chemistry, 2nd Ed., pp. 77 to 81, Interscience Publishers, Inc. NY (1960).
Wolfe et al., Canadian J. of Chemistry, vol. 50, pp. 2902–2905 (1972).
Lowe et al., Chem. Commun. 1971, pp. 577–578.
Brunwin et al., Chem. Commun. 1971, pp. 865–867.
Sheehan et al., J. Heterocyclic Chemistry, vol. 5, pp. 779–783 (1968).
Pearlman, Topics in Pharmaceutical Sciences, vol. 1, Chapter 2, pp. 33 to 51, Interscience Publishers (1968).
Doyle et al., Canadian Journal of Chemistry, pp. 468–483 (1975).
Lednicer et al., The Organic Chemistry of Drug Synthesis, pp. 408–422, John Wiley and Sons (1977).
Kim et al., Tetrahedron Letters, No. 5, pp. 409 to 412 (1978).
Cama et al., J. Am. Chem. Soc. vol. 96, pp. 7582–7584 (1974).
Firestone et al., J. Med. Chem. vol. 20, pp. 551–556 (1977).

*Primary Examiner*—John D. Randolph
*Attorney, Agent, or Firm*—James A. Arno; Julian S. Levitt

[57] ABSTRACT

Novel antibiotics of the formula:

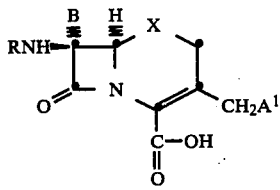

and its salts, esters and amides wherein
R is acyl;
B is H, OMe, Me or SR wherein R is lower alkyl or aryl;
$A^1$ is hydrogen, hydroxy, or an organic group; and,
X is a divalent radical selected from —O—, —$CH_2$—, or —NY— where Y is hydrogen or lower alkyl of from 1 to 6 carbon atoms such as methyl, ethyl, i-propyl, n-butyl, n-pentyl, n-hexyl and the like, formyl or benzyl.

This invention is directed to novel antibiotics, novel intermediates useful in their preparation, and processes for preparing the novel antibiotics. The novel antibiotics are effective against gram-negative bacteria including *Proteus vulgaris*, *E. coli* and *Salmonella schottmulleri*, and gram-positive bacteria including *Staphylococcus aureus* and *Bacillus subtilis* and are useful in combatting bacterial infections in animals or humans in addition to various industrial applications.

19 Claims, No Drawings

NOVEL ANTIBIOTIC ANALOGUES OF CEPHALOSPORINS

This is a continuation of application Ser. No. 869,199, filed Jan. 13, 1978, now abandoned; which is a continuation of U.S. Ser. No. 587,526, filed June 16, 1975 now abandoned; which in turn is a continuation-in-part of U.S. Ser. No. 395,662, filed Sept. 18, 1973, now abandoned; which in turn is a continuation-in-part of U.S. Ser. No. 303,905, filed Nov. 6, 1972, now abandoned.

The novel compounds of this invention have the following structural formula:

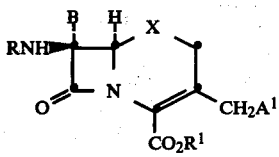

wherein
B is H, $OCH_3$, $CH_3$, SR wherein R is lower alkyl of 1–6 carbon atoms (e.g., methyl, ethyl, propyl, butyl, hexyl) or aryl (e.g., phenyl):
R is an acyl radical;
$R^1$ is hydrogen or a protecting group;
$A^1$ is hydrogen, hydroxy, substituted hydroxy, mercapto, substituted mercapto, a quaternary ammonium group, azido, halo, amino or N-substituted amino;
X is a divalent radical selected from —O—, —$CH_2$—, or —NY— where Y is hydrogen or lower alkyl of from 1 to 6 carbon atoms such as methyl, ethyl, i-propyl, n-propyl, n-pentyl, n-hexyl and the like, formyl or benzyl,
and non-toxic, pharmacologically acceptable salts, esters or amides thereof.

The acyl radical represented by R can be a substituted or unsubstituted aliphatic, aromatic or heterocyclic, araliphatic or heterocylylaliphatic carboxylic acid radical or a carbothioic acid radical such as the acyl radicals of the known cephalosporins and penicillins. These acyl radicals can be represented by the general formula:

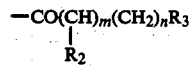

where $R_2$ is a radical of the group defined below, m and n represent 0–4 and $R_3$ represents R" or ZR", which are defined below.

One group of acyl radicals can be represented by the general formula

wherein R" represents a substituted or unsubstituted straight or branched chain alkyl, alkenyl, or alkynyl group; aryl, aralkyl; cycloalkyl; or a heteroaryl or heteroaralkyl group. These groups can be unsubstituted or can be substituted by radicals such as OH, SH, SR (R is alkyl or aryl), alkyl, alkoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3-, or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-quanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)-methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)-methyl, 2- or 3-(5-sulfothienyl)-methyl, 2- or 3-(5-carboxythienyl)methyl, 3-(1,2,5-thiadiazolyl)methyl, 3-(4-methoxy-1,2,5-thiadiazolyl)-methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

wherein n is 0–4, Z represents oxygen or sulfur, and R" is defined as above. Representative members of the substituent

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, p-(carboxy)phenylthiomethyl, p-(carboxymethyl)phenoxymethyl, p-(carboxymethyl)-phenylthiomethyl, 2-pyrimidinylthiomethyl, phenethylthiomethyl, 1-(5,6,7,8-tetrahydronaphthyl)oxomethyl, N-methyl-4-pyridylthio.

Alternatively, the acyl group can be a radical of the formula

wherein R'' is defined as above and R''' is a radical such as amino, hydroxy, azido, carbamoyl, guanidino, acyloxy, halo, sulfamino, tetrazolyl, sulfo, carboxy, carbalkoxy, and the like.

Also of interest is the followng acyl moiety:

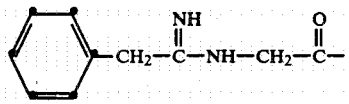

Representative members of the substituent $$-\underset{\underset{R'''}{|}}{C}HR''$$

that might be mentioned are α-aminobenzyl, 2-thienyl-aminomethyl, α-methylaminobenzyl, α-amino-methyl-mercaptopropyl, α-amino-3- or 4-chlorobenzyl, α-amino-3 or 4-hydroxybenzyl, α-amino-2,4-dichlorobenzyl, α-amino-3,4-dichlorobenzyl, β(—)-α-hydroxybenzyl, α-carboxybenzyl, 3-thienyl-aminomethyl D-(—)-α-amino-3-chloro-4-hydroxybenzyl, D(—)-3-thienyl-aminomethyl or 1-aminocyclohexyl, α-(5-tetrazolyl)-benzyl, 2-thienyl-carboxymethyl, 3-thienyl-carboxymethyl, 2-furyl-carboxymethyl, 3-firyl-carboxymethyl, α-sulfaminobenzyl, 3-thienyl-sulfaminomethyl, α-(N-methylsulfamino) benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolylaminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono.

The acyl substituents of the general formula

R₂R₃CHCO wherein R₂ and R₃ are as defined below represent a preferred group of substituents because of their generally useful antibiotic activity. R₃ represents hydrogen, halo, amino, guanidino, phosphono, hydroxy, tetrazolyl, carboxy, sulfo, or sulfamino. R₃ represents phenyl, substituted phenyl, a monocyclic heterocyclic 5- or 6-membered ring containing one or more oxygen, sulfur or nitrogen atoms in the ring, such as furyl, thienyl, thiazolyl, isothiazolyl, tetrazolyl, oxadiazolyl, thiadiazolyl and the like, substituted heterocycles, phenylthio, phenyloxy, lower alkyl of 1–6 carbon atoms, heterocyclic or substituted heterocyclic thio groups; or cyano. The substituents can be halo, carboxymethyl, guanidino, quanidinomethyl, carboxamidomethyl, aminomethyl, nitro, methoxy, or methyl.

Particularly preferred are acyl groups where X is hydrogen, hydroxy, amino or carboxy and R₃ is phenyl, or a 5- or 6-membered heterocyclic ring having one or two sulfur, oxygen or nitrogen hetero atoms, such as tetrazolyl, thienyl, furyl and phenyl.

Examples of acyl radicals of interest are phenylacetyl, 3-bromophenylacetyl, p-aminomethylphenylacetyl, 4-carboxymethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadieneacetyl, α-sulfaminophenylacetyl, α-hydroxyphenylacetyl, α-tetrazolylphenylacetyl and α-sulfophenylacetyl.

However, it is to be understood that any acyl radical that is conventionally employed in the cephalosporin and penicillin antibiotic art may be employed in the practice of the invention and is to be considered within the scope of the invention.

The substituent A¹ in formula (I) above can be hydrogen, hydroxy, halo, mercapto, substituted hydroxy, substituted mercapto, a quaternary ammonium group, azido, amino or a N-substituted amino group.

A¹ can be a halo such as chloro, bromo, fluoro or iodo.

When A¹ is substituted hydroxy or a substituted mercapto group, it can be shown by the formula:

—ZR$_x$ where Z is oxygen or sulfur, and R$_x$ is an acyl group, such as lower alkanoyl of 1–6 carbon atoms, aroyl, carbamoyl, or carbamoylthio, a straight chain or branched chain loweralkyl (1–6 C), alkenyl (1–6 C) or alkynyl group (1–6 C); an aryl group; an aralkyl group; or a heterocyclic group such as heteroaryl or heteroalkyl. The heterocyclic group is preferably a 5- or 6-membered ring containing one or more sulfur, nitrogen or oxygen atoms. These groups can be unsubstituted or can be substituted by radicals such as alkyl (1–6 carbons), alkoxy (1–6 carbon atoms), halo, cyano, carboxy, carbamoyl, N-substituted carbamoyl, azido, sulfo, amino, substituted amino, haloalkyl, carboxyalkyl, carbamoylalkyl, N-substituted carbamoylalkyl, guanidino, N-substituted guanidino, guanidinoalkyl, sulfamyl, substituted sulfamyl, and the like.

Representative of the groups —ZR$_x$ thus presented that might be mentioned are isoxazolylthio, pyrolidenylthio, 1,3,4-thiadiazolylthio, 1-oxidopyridylthio, furazanylthio, tetrazolylthio, thienylthio, thiazolylthio, furylthio, pyranylthio, pyrrolylthio, imidazolylthio, pyrazolylthio, pyridylthio, pyrazinylthio, pyrimidinylthio, pyridazinylthio, isothiazolylthio, methoxy, n-propoxy, methylthio, acetoxy, propionyloxy, benzoyloxy, (p-chlorobenzoyl)oxy, (p-methylbenzoyl)oxy, pivaloyloxy, (1-adamantyl)carboxy, butanoyloxy, carbamoyloxy, (N-methylcarbamoyl)oxy, (N-ethylcarbamoyl)oxy, [N-(2-chloroethyl)carbamoyl]oxy, (N-phenylcarbamoyl)oxy, (N-p-sulfophenylcarbamoyl)oxy, p-carboxymethylphenylcarbamoyloxy, methoxycarbonyloxy, isobutanoyloxy, cyclobutylcarbonyloxy, carbamoylthio, (ethoxythiocarbonyl)thio, (N-propoxythiocarbonyl)thio, (cyclopentanoxythiocarbonyl)thio, methylthio, N,N-diethylthiocarbamoylthio, N-methylpiperazinium-1-thiocarbonylthio, N,N-dimethylpiperazinium-1-thiocarbonylthio, 2-furoylthio, isothiouronium, (5-methyl-1,3,4-thiadiazol-2-yl)thio, p-tolylsulfonylthio, mesyloxy, methyl-1,2,3,4-tetrazolyl-5-thio, tosyloxy, sulfamoyloxy, 1-naphthoyloxy, 2-furylacetoxy, cinnamoyloxy, p-hydroxycinnamoyloxy, p-sulfocinnamoyloxy and 1R:2S-epoxypropylphosphonyloxy.

Alternatively, when A' is hydroxy, the cephalosporin can also exist as the lactone which is formed by internal esterification with the carboxy group.

The substituent A' can also be a group of the general formula $$-Y_1$$

wherein $Y_1$ represents amino or substituted amino including nitrogen heterocycles and substituted heterocyclic groups. Examples of such groups that might be mentioned are amino, acetamido, carbamoylamino, N,N-dimethylamino, N-(2-chloroethyl)amino, 5-cyanotriazol-1-yl, 4-methoxycarbonyltriazol-1-yl.

When $A^1$ is amino the cephalosporin compound can also exist as the lactam formed by loss of water with the adjacent carboxy group.

Representative of the quaternary ammonium groups representing $A^1$ that might be mentioned are pyridinium, lower alkyl (1–6 carbon atoms), pyridinium or halopyridinium such as 3-methylpyridinium, 4-methylpyridinium, 3-chloropyridinium, 3-bromopyridinium, 3-iodopyridinium; aminopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)-pyridinium, 4-(carboxymethyl)pyridinium, 4-(hydroxymethyl)pyridinium, 4-(trifluoromethyl)pyridinium, quinolinium, picolinium and lutidinium.

The preferred groups representing A' are hydrogen, halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5 or 6-membered hetero ring containing one or more nitrogen, oxygen or sulfur atoms. The acyl groups of interest include a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted by radicals such as alkoxy, halo, amino, cyano, carboxy, sulfo, and the like.

It may be noted that the substituent at the 3-position of the nucleus may be converted to or readily replaced by other $A^1$ substituents pursuant to methods well known in this art. For example, upon treating the 3-acetoxymethyl substituted material of this invention with a suitable reagent or combination of reagents, it is possible to substitute various substituents for acetoxy at the 3-position of the nucleus. Suitable reagents include, for example, isocyanates; alkali metal toluenesulfinates, alkali metal azide, polyhydroxybenzene, N-loweralkyl indole, thiourea, mercaptans, thiocyanates, heterocyclic thiols, cycloalkyl xanthates, pyridine, thiobenzoic acid, N-alkyl and N,N-dialkylthioureas or alkali metal N-alkyl and N,N-dialkylthiocarbamates and the like.

Thus by reaction wih a heterocyclic thiol, for example 1-methyl-1,2,3,4-tetrazole-5-thiol or 5-methyl-1,3,4-thiadiazole-2-thiol, the 3-acetoxymethyl material is converted to the corresponding heterothiomethyl compound.

Also, by reaction with a quaternary ammonium compound, for example pyridine, the 3-acetoxymethyl is converted to the corresponding 3-pyridiummethyl compound. Alternatively, the 3-acetoxymethyl material upon treatment with citrus acetylesterase are converted to the corresponding 3-hydroxymethyl compounds which can be acylated to produce other 3-acyloxymethyl including carbamoyloxymethyl, or acylthiomethyl compounds. Similarly, other 3-substituted compounds are prepared following procedures well known in this art.

Thus, the acetoxy group of such compounds can be cleaved to produce the corresponding 3-hydroxymethyl compound by enzymatic hydrolysis with acetylesterase. The resulting hydroxy group may then be reacted to form other substituents at the 3-position. For example, the 3-hydroxy group may be re-esterified with a lower alkanoic acid group or with an aryl acid group by employing acylating agents such as a lower alkyl or aryl carboxylic acid halide or anhydride, a substituted carbamoyl halide, a lower alkyl isocyanate, or phosgene and a secondary amine.

The 3-acetoxy group may also be converted to other analogs by replacing the acetoxy group with nitrogen or sulfur nucleophiles. Many nitrogen and sulfur nucleophiles are well known in the cephalosporin art and the following examples are merely illustrative of the type of compound which may be employed; for example, a tertiary amine such as pyridine and the like, a 5-membered heterocyclic thiol such as 5-methyl-1,3,4-thiadiazolyl-2-thiol, N-methyltetrazolylthio and the like. Alternatively, the 3-acetoxy group can be cleaved by catalytic hydrogenation to afford the 3-methyl compounds.

One method for the introduction of an N,N-diloweralkylcarbamoyloxymethyl or heterocyclic aminocarbonyloxyethyl moiety at position 3 of the instant products consists in treating a 3-hydroxymethyl analog such as a 3-hydroxymethyl-7-methoxy-7-(2-thienylacetamido)-1-methylene-dethia-ceph-3-em-4-carboxylic acid with phosgene and a diloweralkylamine in the presence of a base. In this manner the following products can be obtained: sodium dl-3-(N,N-dimethylcarbamoyloxymethyl)-7-methoxy-7-(2-thienylacetamido)-1-methylenedethiaceph-3-em-4-carboxylate and sodium dl-3-(pyrrolidinylcarbonyloxymethyl)-7-methoxy-7-(2-thienylacetamido)1-methylenedethia-ceph-3-em-4-carboxylate.

The N-mono substituted carbamoyloxyethylcephalosporin products are obtained by treating a 3-hydroxymethyl-material with a suitable isocyanate.

The unsubstituted carbamoyloxymethyl may be obtained by cleaving an N mono- or di-substituted carbamoyloxymethyl material such as N,N-di-p-methoxybenzylcarbamoyloxymethyl or N-2,2,2-trichloroethyl carbamoyloxymethyl. An alternative method for obtaining the carbamoyloxymethyl group at the 3-position involves treating the 3-hydroxymethyl analog with trichloroacetylisocyanate or chlorosulfonylisocyanate, followed by hydrolysis.

Antibiotic compounds of Formula (I) that are of particular interest are those wherein X is —O—, —CH₂—, or NY wherein Y is hydrogen, methyl or formyl; and A is hydrogen, lower alkanyloxy, carbamoyloxy, pyridinium, 1-methyl tetrazolylthio, or 2-methyl-1,3,4-thiadiazolylthio, R is of the formula:

wherein $R^3$ is phenyl, a 5- or 6-membered monocyclic heterocycle containing one or more oxygen, sulfur or nitrogen atoms or

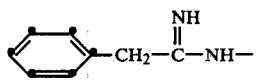

and $R^2$ is hydrogen, halo, amino, guanidino, phosphono, hydroxy, tetrazolyl, carboxyl, sulfo or sulfamino.

The carboxy group of the starting material is blocked or protected, preferably by the use of a group $R^{1'}$, which can be removed to obtain the free acid without disruption of the β-lactam moiety. Protecting groups suitable for this purpose are well known in the art.

The group protecting the carboxyl group may be formed with an alcohol (aliphatic or araliphatic), phenol, silanol, stannanol or acid which may readily be split off at a later stage of the reaction.

Suitable esters thus include compounds containing as the 4-ester group, a group selected from the following list which is representative and not intended to be an exhaustive list of possible ester groups:

(i) —COOCR$^a$R$^b$R$^c$ wherein at least one of R$^a$, R$^b$ and R$^c$ is an electron-donor, e.g. p-methoxyphenyl, 2,4,6-trimethylphenyl, 9-anthryl, methoxy, acetoxy, CH₂SCH₃, tetrahydrofur-2-yl, tetrahydropyran-2-yl or fur-2-yl. The remaining R$^a$, R$^b$ and R$^c$ group may be hydrogen or organic substituting groups. Suitable ester groups of this type include p-methoxybenzyloxycarbonyl and 2,4,6-trimethylbenzyloxycarbonyl.

(ii) —COOCR$^a$R$^b$R$^c$ wherein at least one of R$^a$, R$^b$ and R$^c$ is an electron-attracting group; e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —COOCR$^a$R$^b$R$^c$ wherein at least two of R$^a$, R$^b$ and R$^c$ are hydrocarbon such as alkyl, e.g. methyl or ethyl, or aryl e.g. phenyl and the remaining R$^a$, R$^b$ and R$^c$ group, if there is one, is hydrogen. Suitable esters of this type include t-butyloxycarbonyl, t-amyloxycarbonyl, diphenylmethoxycarbonyl and triphenylmethoxycarbonyl.

(iv) —COOR$^d$ wherein R$^d$ is adamantyl, 2-benzyloxyphenyl, 4-methylthiophenyl or tetrahydropyran-2-yl.

Silyl esters may conveniently be prepared from a halosilane or a silazane of the formula $R^4_3SiX$; $R^4_2SiX_2$; $R^4_3Si.NR^4_2$; $R^4_3SN.R^4_3$; $R^4_3Si.NH.COR^4$; $R^4_3Si.NH.CO.NH.SiR^4_3$; $R^4NH.CO.NR^4SiR^4_3$; or $R^4C(OSiR^4_3)$: $NSiR^4_3$ where X is a halogen and the various groups $R^4$, which can be the same or different, represent hydrogen atoms or alkyl, e.g. methyl, ethyl, n-propyl, iso-propyl; aryl, e.g. phenyl; or aralkyl, e.g. benzyl groups.

Preferred derivatives of silanols are silyl chlorides such as for example trimethylchlorosilane and dimethyldichlorosilane.

Protecting groups of particular interest includes esters of alcohols and phenols, and the like. R" is preferably an alkyl or aralkyl group containing from 1 to about 20 carbon atoms. Thus, R" can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethylgroup such as 2,2,2-trichloroethyl, 2-methylthioethyl or 2-(p-methylphenyl)ethyl, an alkoxyalkyl group such as methoxymethyl, an aryloxyalkyl such as p-methoxyphenoxymethyl, an aralkyloxyalkyl group such as benzyloxymethyl, a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, 2,2,2-trichloroethyl, p-methoxybenzyl, p-nitrobenzyl, benzyl, benzhydryl, methoxymethyl and p-methoxyphenoxymethyl.

The term "blocking group" as utilized herein is employed in the same manner and in accordance with the teaching of U.S. Pat. No. 3,697,515; the contents therein with respect to said blocking group being incorporated herein by reference.

The carboxyl groups may be regenerated from an ester by any of the usual methods; for example, acid- and base-catalysed hydrolysis (especially for silyl and stannyl esters) is generally applicable, as well as enzymically-catalysed hydrolyses; however, aqueous mixtures may be poor solvents for these compounds and they may case isomerizations, rearrangements, side-reactions, and general destruction, so that special methods may be desirable. Five suitable methods of deesterification are:

A- Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole.

B- Reduction: Suitable systems for effecting reduction are zinc/acetic acid, zinc/formic acid, zinc/lower alcohol, palladised-charcoal and hydrogen, electrolysis and sodium and liquid ammonia.

C- Attack by nucleophiles: Suitable nucleophiles are those containing a nucleophilic oxygen or sulphur atom for example alcohols, mercaptans and water.

D- Oxidative methods: For example, which involve the use of hydrogen peroxide and acetic acid.

E- Irradiation.

Of particular interest are the procedures involving cleavage of groups such as benzhydryl, tertiary butyl, p-bromophenacyl, p- methoxybenzyl and p-methoxyphenoxymethyl, and methoxymethyl with an acid such as trifluoroacetic acid and cleavage of the 2,2,2-trichloroethyl and phenacyl groups by reaction with zinc and acetic acid.

The process for preparing the 7-acylamido compounds (I, supra) comprises treating the 7-amino or 7-substituted imino compound (II, infra) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, a mixed acid anhydride with other carboxylic acids and particularly lower alkyl esters of carboxylic acids; also, carboxylic acids in the presence of a carbodiimide such as 1,3-dicyclohexylcarbodiimide, an activated ester of a carboxylic acid such as the p-nitrophenyl ester or by enzymatic acylation.

When an imino compound is employed increased yields are obtained when the imino compound is first treated with a metal catalyst. The first step comprises dissolving the imino compound in an inert solvent such as tetrahydrofuran, dimethylsulfoxide, dioxane, dimethylformamide, methanol, ethanol, methylene chloride or chloroform. A small amount of water is then added such that the solvent to water ratio is about 5-6:1. The metal catalyst is then added and the reaction mixture stirred at ambient temperature for 1-5 hours. The solvent may be removed or the acylating agent added directly to the reaction mixture. The catalyst is of the formula $ML_n$ where M is a metal such as palladium, platinum, nickel, ruthenium, rhodium, cobalt or iron; L is the ligand such as halo; carbonyl; cyclopentadienyl; phenylcyano and the like and n is an integer which is equal to the valence requirements. Palladium chloride ($PdCl_2$) is the preferred catalyst.

The acylation reaction may be conducted at a temperature in the range of from about $-20°$ C. to about $100°$ C. but is preferably conducted at a temperature in the range of from $0°$ C. to $25°$ C. Any solvent in which the reactants are soluble and substantially inert may be employed, for example, hydrocarbons such as benzene, toluene and the like or tertiary amines, for example, trialkylamines and heterocyclic amines such as trimethylamine, pyridine and the like, also methylene chloride, chloroform, ethylacetate or diethylether may be employed. The reaction is conducted for a period of time of from about five minutes to a maximum of three hours, but in general, a reaction time of about 0.5 to about one hour is sufficient. The following equation illustrates this process employing the carboxylic acid halide; however, it is to be understood that by substituting the corresponding carboxylic acid anhydride or other functionally equivalent acylating agents similar products may be obtained.

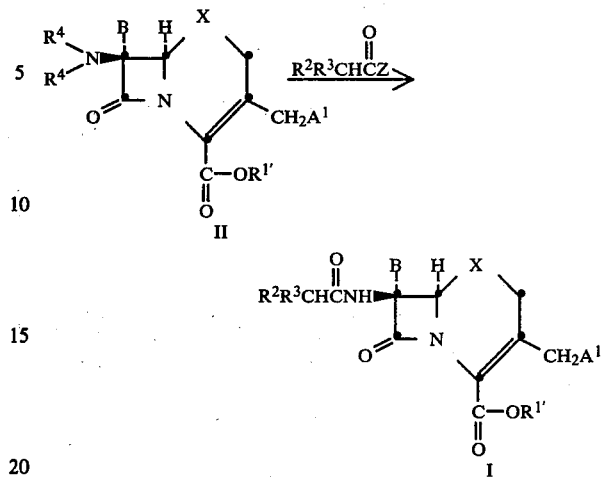

wherein $R^2$, $R^3$, B and X are as defined above; $A^1$ is hydrogen, lower alkanoyloxy, heterocyclic thio, or carbamoyloxy, $R^{1'}$ is a blocking group or H; $R^4$ is hydrogen, or both $R^4$ groups taken together is benzylidene or substituted benzylidene, and Z is halo, for example, chloro, bromo and the like.

The 7β-amino and 7β-substituted imino compounds, (IIa and IIb, respectively, infra) are prepared by various processes depending upon the nature of the X group. When X is methylene, the following procedure depicted in Flow Sheet I is employed:

Flow Sheet I

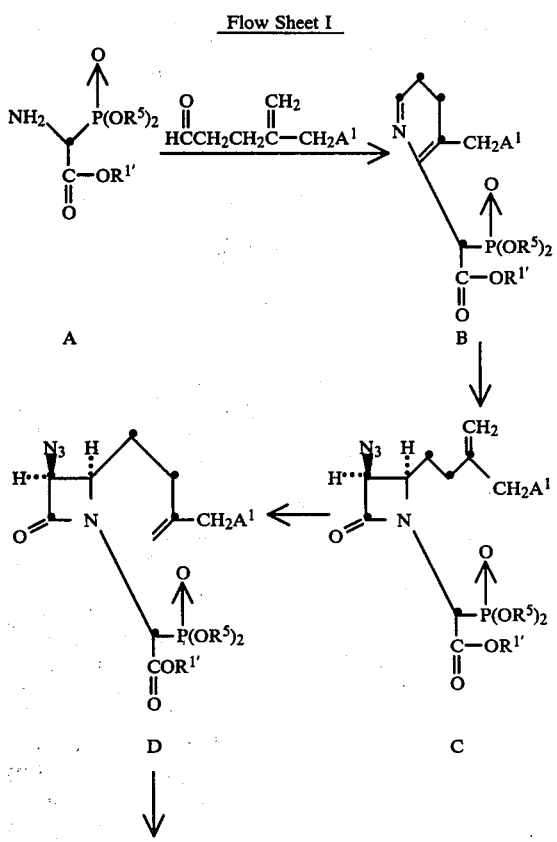

-continued
Flow Sheet I

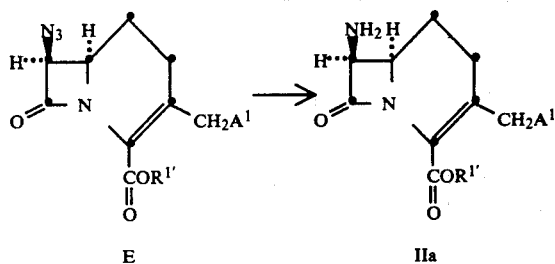

wherein $A^1$ and $R^{1'}$ are as defined above and $R^5$ is lower alkyl of 1–5 carbon atoms such as methyl, ethyl, propyl, n-butyl and the like, or an aryl radical such as phenyl and the like.

In this process the starting material, an ester of α-aminophosphonoacetate (A) is reacted with a 4-methylene-5-substituted-(or unsubstituted)-valeraldehyde to produce the corresponding imine (B). The various phosphono esters of the starting material, A, can be utilized in this process, for example, the di-lower alkyl esters and di-aryl esters of the phosphonic acid group may be employed. This reaction is generally conducted at a temperature in the range of from about 0°–100° C. This reaction is conducted employing a solvent which will azeotrope the water formed during the reaction, with benzene being the preferred solvent. Alternatively, reaction is conducted in an inert solvent such as $CH_2CH_2$, $CHCl_3$, OH, $Et_2O$ and in the presence of a water scavenger such as $MgSO_4$, molecular series, etc. The intermediate compound (B) is then reacted with azidoacetyl chloride in the presence of an acid scavenger to afford the correspondingly substituted methyleneazetidinone (C). This reaction is preferably carried out at low temperatures, for example, at about 0° C. and in the presence of a sufficient amount of base for example, a tertiary amine such as triethylamine to serve as an acid scavenger.

The methyleneazetidinone (C) is converted to the correspondingly substituted oxo-azetidinone (D) by treating with an oxidizing agent, for example, ozone and the like. This reaction is preferably run at low temperatures, for example, a temperature in the range of from −50° to −80° C. Any solvent which is inert or substantially inert to the reactants may be employed, such as ethylacetate, methanol, methylene chloride, chloroform and the like.

The oxo-azetidinone (D) is then cyclized to afford the azabicyclo (4, 2, 0)octene (E). This reaction is conducted employing a base such as an alkali metal hydride or alkali metal carbonate, for example, sodium hydride or potassium carbonate and the like. This reaction is generally run at a temperature in the range of from about 0° C. to about 50° C. Any solvent which is inert or substantially inert may be employed. Suitable solvents include dimethoxyethane, dimethylformamide, dimethylsulfoxide and the like.

The 7β-azido compound (E) is then treated with hydrogen in the presence of a noble metal catalyst such as platinum oxide, palladium on carbon and the like, to obtain the correspondingly substituted 7β-amino compound IIa.

Flow Sheet I' illustrates an alternative method of producing the oxo-azetidinone (D) of Flow Sheet I by utilizing a valeraldehyde which contains a 4-carbonyl precursor or 4-masked carbonyl group in place of the 4-methylene valeraldehyde of Flow Sheet I. The conditions of proceeding from A'→ B'→ C'→ D (Flow Sheet I') are identical with those set forth in Flow Sheet I with respect to the reaction of A→ B→ C→ D.

FLOW SHEET I'

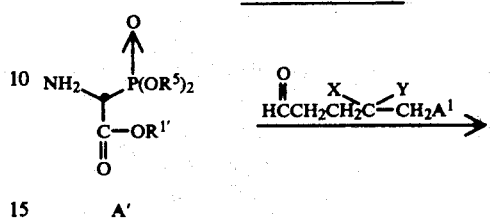

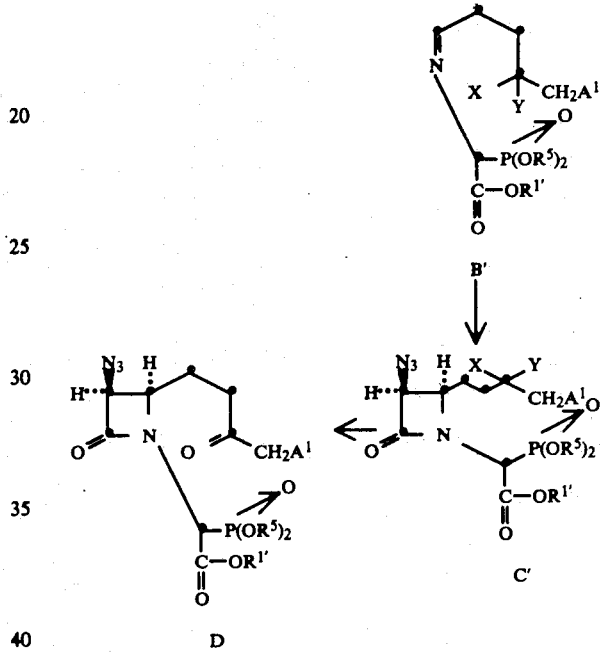

wherein $A^1$ and $R^{1'}$ are as defined above and $R^5$ is lower alkyl of 1–5 carbon atoms such as methyl, ethyl, propyl, n-butyl and the like, or an aryl radical such as phenyl and the like, and X, Y represent a carbonyl precursor or masked carbonyl, representative members of which include the following:

I. Carbonyl precursors $X,Y = =CH_2, =CHR, =CR_2$ (R=lower alkyl)

II. Masked carbonyls

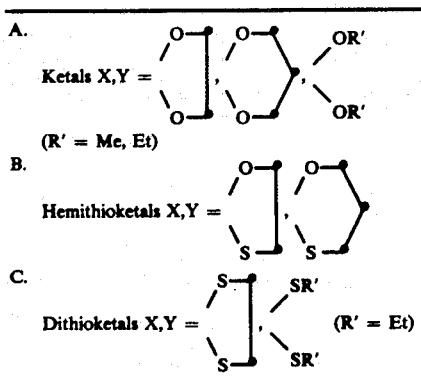

D.

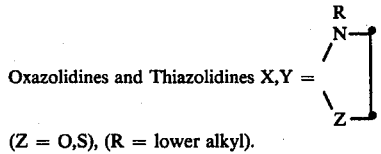

Oxazolidines and Thiazolidines X,Y =

(Z = O,S), (R = lower alkyl).

Regeneration of the carbonyl to form the oxo-azetidinone (D) may be effected by treating the azetidinone (C') with an oxidizing agent such as ozone in the case of the carbonyl presursor and employing acid hydrolysis where X,Y is a masked carbonyl in accordance with technique well known to the art.

Another method for preparing the 7β-amino compound (IIa, infra) and one limited to the preparation of those compounds wherein X is —O— or —NY— where Y is as defined above is shown in the following Flow Sheet, II.

tate, benzhydryl α-amino-diphenylphosphonoacetate, t-butyl, α-amino-dimethylphosphonoacetate, t-butyl α-amino-dipropylphosphonoacetate, methyl α-amino-diphenylphosphonoacetate, phenacyl or p-bromophenacyl α-amino-diethylphosphonoacetate, methoxymethyl α-amino-dimethylphosphonoacetate, p-methoxyphenoxymethyl α-amino-dimethylphosphonoacetate, p-nitrobenzyl α-amino-dimethylphosphonoacetate and benzyl α-amino-diethylphosphonoacetate.

The conversion of compound A to the corresponding thioformamido derivatives (J) is carried out by reacting the starting material with a lower alkyl ($C_1$–$C_6$) ester of thiono formic acid. Thus, the reaction is carried out by reaction with ethyl thionoformate at 0° C. Generally, it is preferred to carry out the reaction in an inert solvent such as benzene, carbon tetrachloride, methylene chloride or hexane. Alternatively, the reaction is carried out in the presence of liquid hydrogen sulfide at room temperature under autogenous pressure. After completion of the reaction, the solvent is evaporated to afford the Flow Sheet II

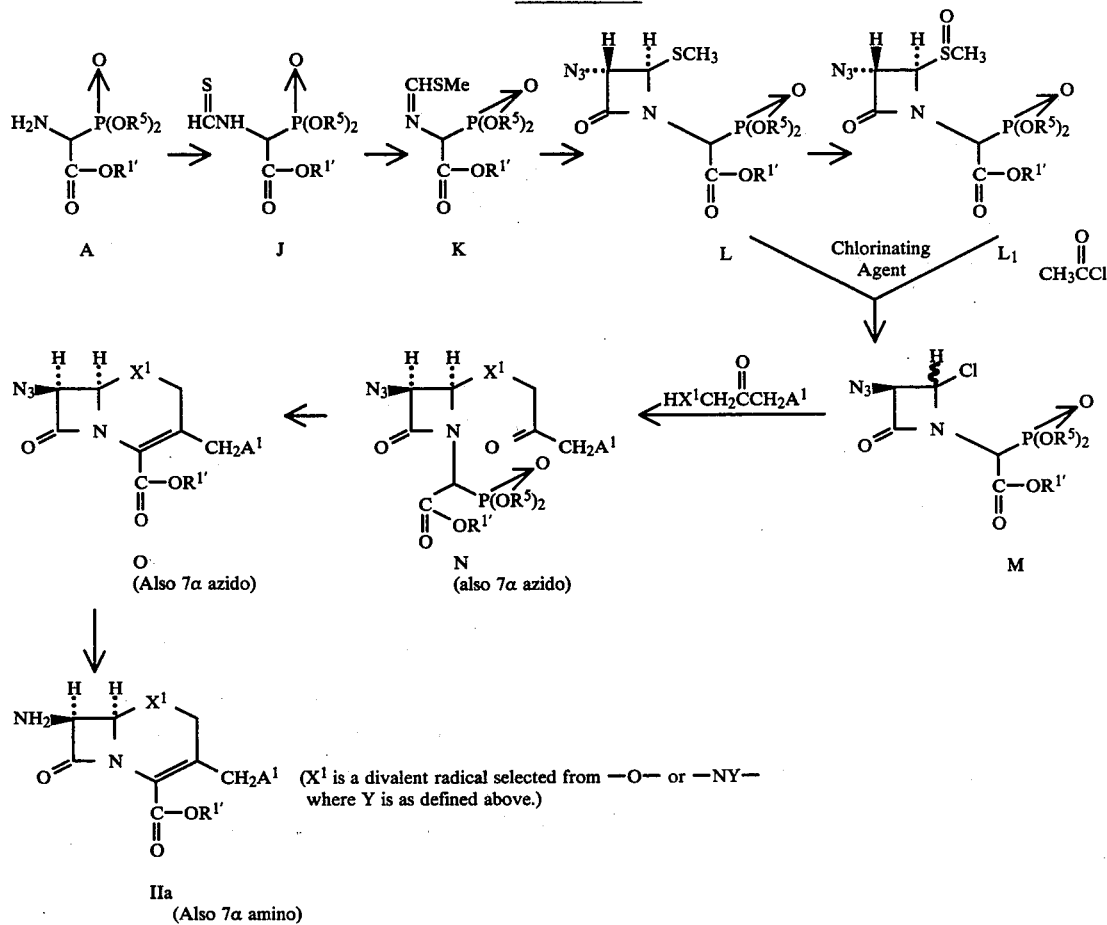

In this process the starting material, an ester of α-aminophosphonoacetate (A) is reacted with a thionoformate ester to produce the corresponding thioformamido ester (J). The protecting group, $R^{1'}$, is as defined above and $R^5$ is as defined above.

Examples of suitable starting materials that might be mentioned are trichloroethyl α-amino-diethylphosphonoacetate, trichloroethyl α-amino-diphenylphosphonoacetate, phenyl α-amino-dimethylphosphonoacetate, p-methoxybenzyl α-amino-diethylphosphononaceproduct, J.

The next step comprises treating the thioformamido compound (J) with an alkylating agent such as methyliodide and the like in the presence of a base such as potassium carbonate, and the like. This step is conveniently conducted at room temperature in the presence of a suitable inert solvent such as acetone, dimethylformamide, and the like. The S-methyl substituted compound (K) obtained is then treated with azidoacetylchloride and an acid scavenger to afford the azido compound (L). This reaction is preferably conducted at low temperatures, for example, at about 0° C. using a sufficient amount of a base such as a tertiary amine to serve as the acid scavenger and also catalyze the cyclo addition to afford compound (L).

The 4-methylthio compound (L) is converted to the correspondingly substituted 4-chloro compound (M) by either of two alternative processes. The first method comprises treating the 4-methylthio compound (L) with an oxidizing agent such as N-bromoacetamide and the like to afford the 4-methylsulfonyl compound (L₁) which upon treatment with acetylchloride affords the desired 4-chloro compound (M).

A second method for preparing the 4-chloro compound comprises treating the 4-methylthio compound (L) with a chlorinating agent such as chlorine and the like, in a suitable inert solvent such as methylene chloride, chloroform, benzene, and the like, at a temperature in the range of from about 0° to about 40° C.

The next step of the process comprises treating the 4-chloro compound (M) with the appropriately substituted propanone or 1-amino (or 1—OH)-3-A'-substituted-2-propanone in the optional presence of a dehalogenating agent, for example, silver fluoroborate, silver oxide, silver trifluoromethanesulfonate, and the like. Suitable solvents for this reaction include methylene chloride, toluene, chloroform, and the like. If the propanone employed as the reactant is a liquid at room temperature then an excess may serve as the solvent. The reaction is conveniently conducted at room temperature.

The 4-propyloxy or propylamino compound (N) is then ring-closed by reaction with a base such as an alkali metal carbonate or an alkali metal hydride in a suitable inert solvent such as dimethoxyethane, dimethylformamide, dimethylsulfoxide, acetone, and the like, at 0°-50° to afford the desired dethiacephalosporanate (O, supra) which is a mixture of the 7α and β-azido compound.

The mixture of the 7α and 7β-azido-dethiacephalosporanate (O) is converted to its correspondingly substituted 7amino compound (IIa, supra) by treating the 7-azido compound (O) with hydrogen in the presence of a noble metal catalyst such as platinum oxide, palladium on charcoal, ruthenium, rhodium and the like.

The compounds, —IIa, described in Flow Sheet I, and the compounds, —IIa, as described in Flow Sheet II, since they result from a total synthesis procedure, are racemic mixtures of both d- and l-forms. The separation of the two optically active components can be conveniently done when the compound of Formula IIa is obtained. Alternatively, the compound of Formula II can be acylated to yield the d, 1-7β-acylamino compound of I and then separated using readily available processes. For example, resolution can be accomplished by reaction with an optically active base, separation of the resulting diastereomers and reconversion of the diastereomers to the free acid or a salt thereof.

The 7β-amino-7α-methoxy compounds (IIc) are prepared by treating the 7-amino compound (IIa) with an aromatic aldehyde to form the corresponding imino compound (IIb or IV, infra).

The imino compound (IIb or IV) may be prepared as follows: (It may be noted that when X=O or NY IIa and IIb may be a mixture of 7α and 7β isomers)

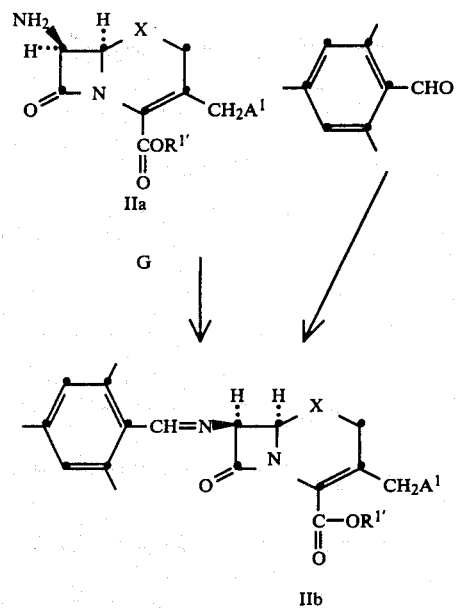

wherein $A^1$ and $R^{1'}$ are as defined above.

The 7-amino compound IIa is reacted with an aromatic aldehyde in which one of the 2, 4 or 6 positions may be substituted with a nitro, halo, cyano, carboxy or hydroxy. The other two positions can either be one of the above substituents or hydrogen. The preferred aromatic aldehydes are benzaldehyde and p-nitrobenzaldehyde. The starting material IIa and the aromatic aldehyde are mixed together in approximately equimolar amounts in an inert solvent, such as ethanol, dioxane, benzene, toluene, methylene chloride, chloroform and the like. The reaction is conducted at room temperature to the reflux temperature of the particular solvent employed. It may be noted that with respect to compound IIa; when X is O or NY a mixture or 7α- and 7β-amino isomers may be present which yield a mixture of 7α and 7β imino compounds (IIb). It will be appreciated that both 7α and 7α compound IIb may be used for introduction of substituents at C-7.

To increase the yields, the water formed during the reaction is removed by any of the known methods including azetropic distillation, molecular sieves, magnesium sulfate and the like.

The imino compound, IIb or IV, is then activated with a strong base preferably an inorganic base, for example, an alkali metal hydride such as sodium hydride and the like, or an organometallic compound such as phenyl lithium LiN(iPr)₂ KOtBu tert-butyl lithium and the like. The base is added to a solution of the imino compound (IV) at a temperature in the range of from about −100° C. to about −60° C. under an inert atmosphere (e.g. nitrogen). An inert solvent such as DMF, tetrahydrofuran or acetonitrile is employed.

The activated intermediate is not isolated but treated directly with a halogenating agent such as N-bromosuccinimide, N-bromoacetamide, bromine, tert-butyl hypochlorite, perchloromethyl hypochlorite and the like, to afford the 7-imino-7-halo compound (III, infra) which upon treatment with methanol in the presence of a base such as silver oxide, barium oxide, calcium oxide, cuprous oxide or triethylamine affords the 7β-imino-7α-methoxy compound (IId) which can be acylated or can be treated with an amine in the presence of an acid catalyst as described above to afford the 7β-amino-7α-methoxy compound (IIc, infra).

FLOW SHEET III

The following equation illustrates this process:

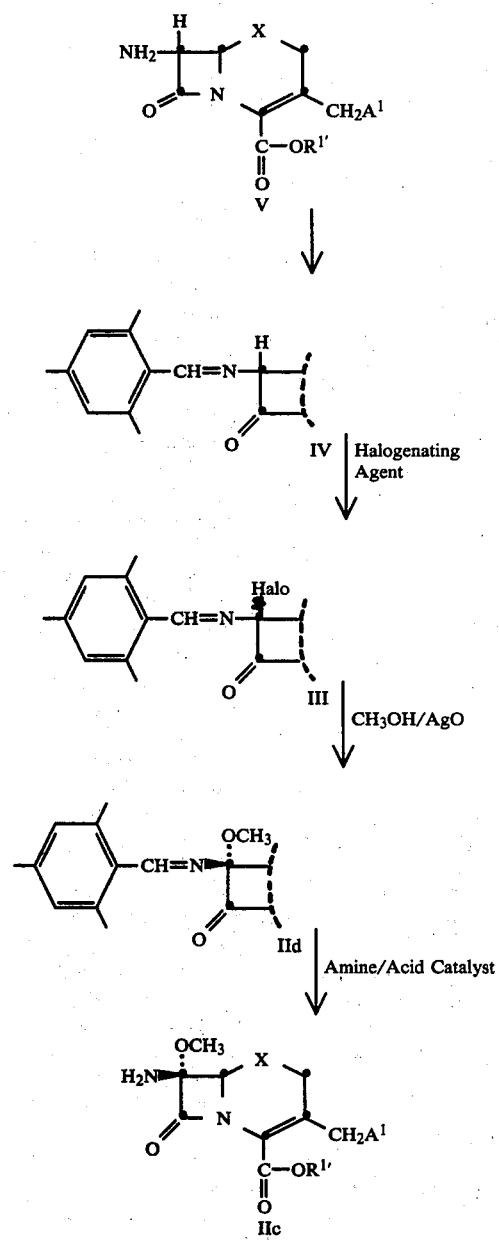

wherein $A^1$, $R^{1'}$ and X are as defined above and halo is bromo or chloro.

An alternative technique for the preparation of novel 7-substituted antibiotics wherein $B = CH_3$, $OCH_3$ or SR (where R is lower alkyl of 1–6 carbon atoms or phenyl) is as follows:

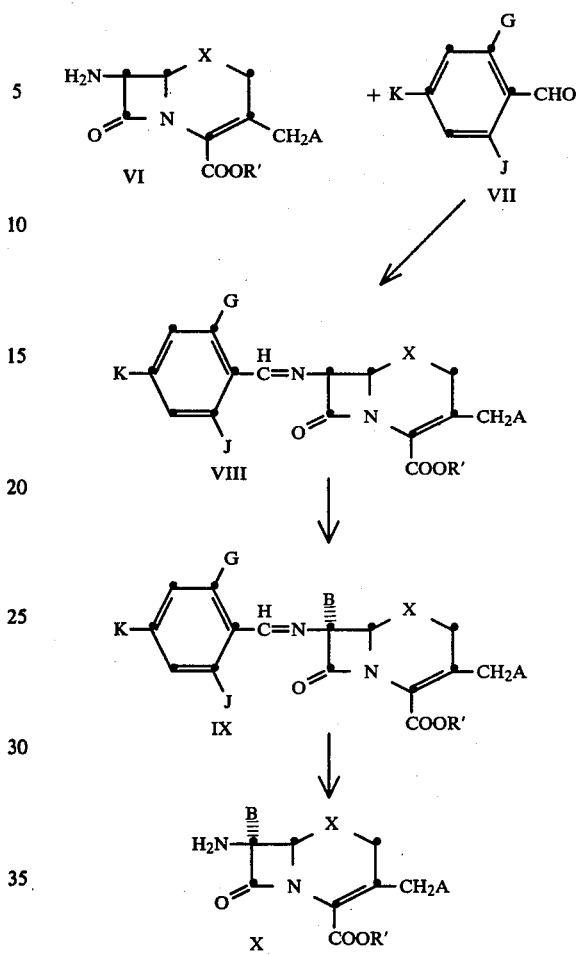

The basic process can be summarized briefly as having three major steps: the first is the preparation of the imino derivative of the 7-amino compound. This imino derivative is then substituted with the chosen reactant supplying the B group desired. The specific reactant depends on the identity of the B group. The third step is then the regeneration of the amino group.

The reactant VII employed in the first of the reaction sequence is an aromatic aldehyde optionally having at least one o- or p-electronegative substituent. In other words, at least one of J, G, and K may be a substituent selected from the group consisting of nitro, methyl, halo, sulfonyl, carboxyl derivatives such as esters or amides, cyano, and the like. The other two of J, G, and K can either be one of the above electronegative substituents, or hydrogen. The preferred reactants are p-nitrobenzaldehyde, where J=nitro, and G and H=hydrogen, and benzaldehyde.

Other carbonyl containing compounds, e.g., aldehydes and ketones such as acetone, hexafluoroacetone or chloral which will form stable imino derivatives will also be operable in this invention. Also, polycyclic aromatic aldehydes can be used, i.e., having 2–3 fused ring nuclei such as 2-hydroxy-1-naphthaldehyde.

The 7-amino starting material VI and the aromatic aldehyde VII are mixed together in approximately equimolar amounts in an inert solvent. Suitable solvents are ethanol, dioxane, acetonitrile, dimethylformamide, dimethylsulfoxide, benzene, toluene, methylene chloride, chloroform, and the like. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The imino derivative VIII is then recovered and used in the next step.

The latter involves the substitution of the B group at the carbon atom adjacent to the imino nitrogen. This reaction takes place in the presence of an inert solvent, such as THf, DMF, DME, and in the additional presence of an activating agent which is an organic or inorganic base.

The activating agent can be any of a number of organic or inorganic bases. Tertiary (loweralkyl) amines are suitable, such as triethylamine, diisopropyl ethylamine; lower alkyl is used as having 1-4 carbon atoms and can be the same or different. Pyridine is also used. Lithium alkyls and lithium aryls, such as lithium alkyls having 1-4 carbon atoms, e.g., t-butyl lithium or phenyl lithium, could be used. Sodium hydride is also suitable LiN(iPr)$_2$ and KOtBu may be used.

The activating agent is added to the solution of compound VIII at a low temperature ($-100°$ to $0°$ C. and preferably $-100°$ to $-60°$ C.) and under an inert atmosphere. The amount of activating agent employed is sufficient to produce a strong color change in the solution. The color is an indicator that the activated form of compound VIII is present.

The activated compound VIII is not isolated, but the next reagent is added directly to the reaction mixture.

The specific reagent which is employed in the reaction with the activated compound VIII to result in the substitution of the chosen B group obviously depends on the B group desired.

The following is of value in defining each reactant in terms of the final B group.

TABLE I

| Reactant | B |
|---|---|
| lower alkyl sulfate or halide (eg. methyl halide) | loweralkyl (eg. CH$_3$) |
| phenylsulfenyl halide | phenylthio |
| lower alkyl peroxide (eg. methyl peroxide) | lower alkoxy (eg. OCH$_3$) |
| loweralkyl disulfide or lower alkane sulfenyl halide (eg. methyl sulfenyl halide) | loweralkylthio (eg. methyl thio) |
| haloloweralkyl disulfide | lowerhaloalkylthio |
| lower alkyl methanethiolsulfonate | lower alkylthio |

The chosen reagent is added in an amount approximately equivalent to the moles of the activated compound VIII. The reaction proceeds immediately, as evidenced by a color change. The reaction mixture is then permitted to warm up to temperatures ranging from between 0° C. to ambient temperatures.

The terms used in Table I and elsewhere in the specification are defined as follows:

"Loweralkyl" refers to an alkyl group having 1-6 carbon atoms.

"Loweralkanoyl" and "loweralkoxy" refer to a carbon chain of 1-6 carbon atoms.

"Halide" and "halo" are used to mean chlorine, bromine, fluorine, and iodine. Different halogens can be employed in the same moiety if more than one is indicated.

"Peroxide" indicates a compound having a —O—O— moiety.

"Disulfide" indicates a —S—S— moiety in a compound.

"Loweralkanoyl peroxide" is used to mean a compound of the formula

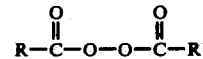

wherein R is loweralkyl having 1-6 carbon atoms.

Once novel compound IX has been prepared, the imino moiety is converted to the amino moiety of compound X.

The regeneration of X from IX takes place by the reaction of IX with an amine in the presence of an acid catalyst. The amine employed can be aniline, hydrazine, or hydrazine derivatives such as phenylhydrazine, 2,4-dinitrophenyl hydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1-5 carbon atoms), such as methanol, ethanol, and the like, although other solvents including dimethoxyethane or dimethyl formamide may also be used. The temperature is that of the surroundings. The relative amounts of acid and amine employed depends on the specific aldehyde IV and amine used, since the regeneration involves an equilibrium. The choice of amounts of the reagents is within the skill of one in the art. Other systems that may be utilized include H$_2$O in methyl ether or DMF or HCl in H$_2$)—methyl ether.

In carrying out the reactions described herein it is preferred to protect the 4-carboxy group and also other groups which may be in the nucleus such as other carboxy groups, amino groups or hydroxy groups. Maximum yields are obtained by employing these protected compounds. Examples of these protecting groups are trichloroethyl, tert-butyl, benzoylmethyl, p-methoxybenzyl, benzyl, benzhydryl, trityl, trimethylsilyl, methoxymethyl, tert-butyloxycarbonyl and the like. These ester groups may be removed by methods well known to those skilled in the art; for example, the benzhydryl or p-nitrobenzyl groups may be removed by hydrogenation in the presence of a catalyst such as palladium-on-carbon or by treatment with a strong organic or inorganic acid. The tert-butyl or methoxymethyl groups may also be removed by treatment with strong organic or inorganic acid. Examples of these acids are hydrochloric acid, sulfuric acid, boron trifluoride etherate, formic acid, trifluoroacetic acid, trichloroacetic acid, nitrobenzoic acid and the like.

Amino protecting groups are well known in the art and are described, for example, in U.S. Pat. Nos. 2,479,295 through 2,479,297, 2,562,407 through 2,562,411 and 2,623,876. Groups such as triphenylmethyl and trimethylsilyl may be employed. The groups set forth in the above indicated patents are incorporated herein by reference. In addition, protective groups formed by reagents such as 1-fluoro-2,4-dinitrobenzene, 1-fluoro-2-nitro-4-carbomethoxy-benzene, p-toluenesulfonyl chloride, phenylisocyanate and methylchloroformate may be employed in the practice of the invention.

Typical of hydroxy protecting groups which may be utilized include tetrahydropyranyl ether, benzyl ether, p-nitrobenzyl ether or p-methoxybenzyl ether. These groups may be subsequently converted to the free hydroxy group by mild aqueous hydrolysis or by hydrogenation.

Preparation of 3-Methyl Analogs

The 3-acetoxy methyl group may be cleaved to form the 3-hydroxymethyl compound without subsequent lacetone formation by employing enzymatic means, for example, by employing acetylesterase. The use of an enzyme allows the hydrolysis of the acetoxy group without the danger of lactone formation. The resulting hydroxy group may be then reacted to form other substituents at the 3-position. For example, the 3-hydroxy group may be re-esterified with a lower alkanoic acid group or with an aryl group by employing acylating agents such as a lower alkyl or aryl carboxylic acid halide or anhydride, a substituted carbamoyl halide or a lower alkyl isocyanate.

The 3-acetoxy methyl group may also be converted to other analogs by replacing the acetoxy group of I, with nitrogen or sulfur nucleophiles. Many nitrogen and sulfur nucleophiles are well known in the cephalosporin art and the following examples are merely illustrative of the type of compound which may be employed; for example, a tertiary amine such as pyridine and the like, a 5-membered heterocyclic thiol such as 5-methyl-1,3,4-thiadiazolyl-2-thiol, N-methyltetrazolyl-thiol and the like.

In accordance with the above, deblocking of the Y-carboxy group of 7-amino or 7-acyl cephalosporins prepared in accordance with the invention shall result in the preparation of the corresponding free acid as follows:

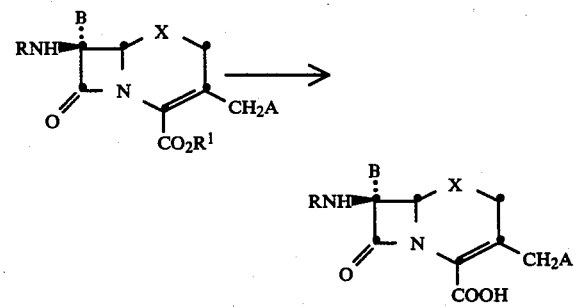

wherein R is H or acyl; $R^1$ is a protecting group; and B and A is as set forth previously.

The nomenclature used in this application is as follows:

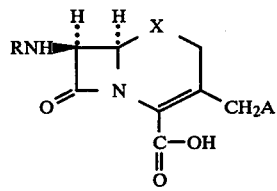

I is called 3-substituted methyl-7$\beta$-acylamido-1-X-1-dethiacephalosporin.

In Formula I, the dotted lines connecting the two hydrogen atoms to the ring indicate that the hydrogen atoms are down (X) from the plane of the $\beta$-lactam ring; the broad line connecting the nitrogen indicates that it is up (B) from the plane of the ring.

There is another possible steric configuration for dethiacephalosporin, which is:

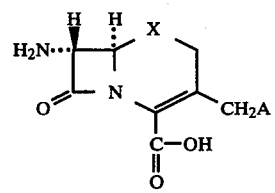

In this formula, the nitrogen and the hydrogen at position 6 is $\alpha$, or down from the ring; the hydrogen at position 7 is $\beta$, or up from the ring. This type of configuration is termed "epi" dethiacephalosporin.

It should be noted that it is unnecessary to specify the configuration of both substituents on the 7-carbon; if the nitrogen configuration is indicated, the other substituent, i.e., the hydrogen, is obviously the other configuration.

EXAMPLE 1

Sodium 7$\beta$-(2-thienylacetamido)-1-methylene-1-dethiacephalosporanate

Step A: Benzyl N-benzylidine-$\alpha$-amino-diethyl-phosphonoacetate

Diethyl N-benzylidine-aminomethylphosphonate (21.8 g.) is dissolved in dry tetrahydrofuran (500 ml.) and cooled to $-78°$ C. under a nitrogen atmosphere. Phenyl lithium (58.6 ml.; 2.3 M) in benzene/ether is added dropwise over a 10-minute period and the resulting solution allowed to stir for 5 minutes. Benzyl chloroformate (9.4 ml.) is then added dropwise over a 30-minute period. The reaction mixture is stirred at $-78°$ C. for one hour and then at $0°$ C. for another half hour. The solvent is evaporated under reduced pressure and the residue is dissolved in ether and washed successively with a phosphate buffer (pH 3) and then with brine. The ether solution is dried and the ether removed to afford 36.0 g. of crude product which is chromatographed on silica gel (1.0 kg.). Elution with ethyl acetate and acetone (9:1) affords 16.5 g. of benzyl N-benzylidine-$\alpha$-amino-diethylphosphonoacetate.

$$\overset{H}{\underset{|}{}}$$
NMR: $\tau$: 1.64 d(C=N); 4.76, s(CH$_2$—C$_6$H$_5$); 5.26; d(CH—P—); 5.9; m(OCH$_2$—CH$_3$); 8.8, t(CH$_3$—CH$_3$—O).

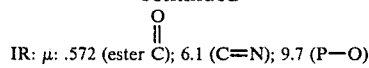
-continued

IR: μ: .572 (ester C); 6.1 (C=N); 9.7 (P—O)

Step B: Benzyl α-amino-diethylphosphonoacetate

Benzyl N-benzylidine-α-amino-diethylphosphonoacetate (16.5 g.) is dissolved in ether (50 ml.) and added dropwise to an ice cold solution of p-toluenesulfonic acid monohydrate (8.08 g.) in ether (300 ml.). After the addition is complete, the reaction mixture is stirred an additional 20 minutes. The ether solution is decanted from the oily product. The oily product is triturated with an ether/petroleum ether solution (1:1) and the soluble material is again decanted. The residual oil is dissolved in dichloromethane (300 ml.) and washed with dipotassium phosphate (1 equivalent of a 1 M solution). The organic solution is dried and the solvent removed to afford 9.6 g. of benzyl α-amino-diethylphosphonoacetate.

NMR: τ: 2.84, s(C₆H₅); 4.77, s(C₆H₅—CH₂); 5.88,

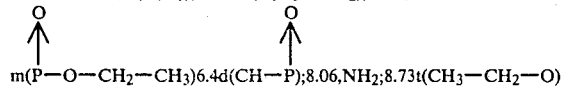
m(P—O—CH₂—CH₃)6.4d(CH—P);8.06,NH₂;8.73t(CH₃—CH₂—O)

IR: μ: 2.95 (NH); 5.72 (ester); 9.7 (P—O—)

Step C: 1-Chloro-2-methylene-3-acetoxypropane

Sodium hydride (4.5 g.; 57% in mineral oil) is placed under a nitrogen atmosphere and the mineral oil removed with petroleum ether. Dimethylsulfoxide (30 ml.) is then added and the mixture is stirred at 70° C. for two hours and then cooled to 10° C. Methyltriphenylphosphonium bromide (35.7 g.) dissolved in dimethylsulfoxide (50 ml.) is added dropwise under nitrogen to afford a yellowish-orange ylide solution. 1-Chloro-3-acetoxy-2-propanone (15 g.) in dimethylsulfoxide (20 ml.) is then added and the reaction mixture is stirred until the color of the ylide disappears and then is stirred an additional hour at room temperature. The reaction mixture is dissolved in hexane (200 ml.) and washed three times with water. The organic phase is filtered to remove triphenylphosphine oxide and then dried over magnesium sulfate. The solvent is evaporated and the residue is distilled under vacuum to afford 1-chloro-2-methylene-3-acetoxypropane.

Step D: 4,4,6-Trimethyl-5,6-dihydro-2-(4'-acetoxy-3'-methylene)butyl-1,3-(4H-oxazine 2,4,4,6-Trimethyl-5,6-dihydro-1,3-(4H)-oxazine (14.1 g.) is dissolved in tetrahydrofuran (100 ml.), cooled to −78° C. under a nitrogen atmosphere and treated with n-butyl lithium (100 ml.; 1 N) in hexane. The reaction mixture is stirred for two hours at −78° C. and then 1-chloro-2-methylene-3-acetoxypropane (14.8 g.) in tetrahydrofuran (50 ml.) is added dropwise. The reaction mixture is allowed to come to room temperature gradually. The solvent is removed under reduced pressure and the residue dissolved in ether (200 ml.) and washed with water. The ether solution is dried and removed by evaporation to afford the crude product which is purified by chromatography on silica gel to afford 4,4,6-trimethyl-5,6-dihydro-2-(4'-acetoxy-3'-methylene)butyl-1,3-(4H)-oxazine.

Step E: 4-Methylene-5-acetoxyvaleraldehyde 4,4,6-Trimethyl-5,6-dihydro-2-(4'-acetoxy-3'-methylene)butyl-1,3-(4H)-oxazine (12.5 g.) is dissolved in tetrahydrofuran (100 ml.) and water is then added until a slightly turbid solution results. The mixture is cooled to −30° C. and sodium borohydride (10 g.) is added in 4 equal amounts. After stirring for one-half hour at −30° C. the reaction mixture is allowed to come to room temperature and is then treated with dilute hydrochloric acid. The reaction mixture is diluted with ether (300 ml.) and then washed successively with water and brine. The ether solution is dried and the solvent removed to afford the tetrahydro oxazine which is then refluxed with oxalic acid (100 ml.; 5%) for one-half hour. The reaction mixture is extracted with ether and the ether solution dried and the solvent removed to afford 4-methylene-5-acetoxyvaleraldehyde.

Step F: Benzyl α-(5''-acetoxy-4'-methylene)-valeraldiminodiethyl phosphonoacetate Benzyl α-aminodiethylphosphonoacetate (3 g.) is mixed with 4-methylene-5-acetoxyvaleraldehyde (1.56 g.). Benzene (150 ml.) is added and the benzene is distilled over a 45-minute period until the volume is 10 ml. The remaining benzene is evaporated under reduced pressure and the residue of benzyl α-5'-acetoxy-4'-methylene-valeraldiminodiethylphosphonoacetate is used immediately in Step G.

Step G: 1-(Benzyloxycarbonyldiethylphosphono)methyl-3-azido-4-cis-(3'-methylene-4'-acetoxy)butyl-2-azetidinone The product of Step F (4.39 g.) is dissolved in methylene chloride (80 ml.) under a nitrogen atmosphere and a solution of azidoacetyl chloride (1.2 g.) in methylene chloride (10 ml.) is added dropwise over a one-half hour period. Triethylamine (distilled from calcium hydride) (1.2 g.) in methylene chloride (10 ml.) is then added dropwise over a 45-minute period and the reaction mixture is allowed to stir at room temperature for another 15 minutes. The reaction mixture is washed with pH 7 phosphate buffer, dried and the solvent removed to afford a crude product which is chromatographed on silica gel (200 g.) to afford 1-(benzyloxycarbonyldiethylphosphono)-methyl-3-azido-4-(cis-(3'-methylene-4'-acetoxy)-butyl-2-azetidinone.

Step H: 1-(Benzyloxycarbonyldiethylphosphono)methyl-3-azido-4-cis-(3'-oxo-4'-acetoxy)butyl-2-azetidinone 1-(Benzyloxycarbonyldiethylphosphono)-methyl-3-azido-4-cis-(3'-methylene-4'-acetoxy)-butyl-2-azetidinone (2.61 g.) is dissolved in ethyl acetate (25 ml.) and cooled to −78° C. and then treated with ozone until the solution shows a blue color. The reaction mixture is stirred at −78° C. for five minutes and then nitrogen is passed into the solution to remove the ozone. The reaction mixture is allowed to come to room temperature and then treated with a 2% solution of potassium iodide and a few drops of acetic acid. The aqueous phase is separated and the organic phase is washed with sodium thiosulfate, dried and the solvent removed. Chromatography on silica gel affords 1-(benzyloxycarbonyldiethylphosphono)methyl-3-azido-4-cis-(3'-oxo-4'-acetoxy)-butyl-2-azetidinone.

Step I: Benzyl 7-β-azido-1-methylene-1-dethiacephalosporanate

Sodium hydride (0.112 g., 57% in mineral oil) is placed under a nitrogen atomsphere and the mineral oil removed with pentane. Anhydrous dimethoxyethane (10 ml.) is added and the mixture is cooled to 0° C. 1-(Benzyloxycarbonyldiethylphosphono)methyl-3-azido-4-cis-(3'-oxo-4'-acetoxy)butyl-2-azetidinone (1.3 g.) in dimethoxyethane (10 ml.) is added dropwise to the sodium hydride suspension and the mixture is stirred for one hour. The reaction mixture is diluted with benzene, washed twice with water, dried and the solvent removed to afford the crude product which is purified by chromatography on silica gel to afford benzyl 7β-azido-1-methylene-1-dethiacephalosporanate.

Step J: Benzyl 7-β-amino-1-methylene-1-dethiacephalosporanate

Benzyl 7β-azido-1-methylene-1-dethiacephalosporanate (1.85 g.) is dissolved in dioxane (30 ml.). Platinum oxide (1.8 g.) is added and the reaction mixture is reduced with hydrogen at atmospheric pressure for three hours. The dioxane is removed under reduced pressure, the residue is dissolved in chloroform and filtered through a short column of silica gel G to remove the catalyst. Evaporation of the solvent afford benzyl 7-β-amino-1-methylene-1-dethiacephalosporanate.

Step K: Benzyl 7β-(2'-thienylacetamido)-1-methylene-1-dethiacephalosporanate Benzyl 7β-amino-1-methylene-1-dethiacephalosporanate (0.5 g.) is dissolved in 20 ml. methylene chloride and cooled to 0° C. Pyridine (0.5 ml.) is added and then 2-thienylacetyl chloride (0.25 g.) is added dropwise and the mixture is allowed to stir at 0° C. for ½ hour. The reaction mixture is washed once with a pH 2 phosphate buffer and then with a pH 8 phosphate buffer. The organic phase is dried and evaporated to afford a residue which is chromatographed on silica gel to give: benzyl 7β-(2-thienylacetamido)-1-methylene-1-dethiacephalosporanate.

Step L: Sodium 7β-(2'-thienylacetamido)-1-methylene-1-dethiacephalosporanate Benzyl 7β-(2-thienylacetamido)-1-methylene-1-dethiacephalosporanate (0.300 g.) is dissolved in ethanol (15 ml.), water is added to turbidity and then 0.300 g. of the catalyst (10% Pd/C) is added. The mixture is reduced under hydrogen at 40 atm. for one-half hour. The catalyst is filtered off. The filtrate is evaporated under reduced pressure to remove most of the ethanol and then treated with sodium bicarbonate (0.1 g.) and the solution is freezedried to afford sodium 7β-(2'-thienylacetamido)-1-methylene-1-dethiacephalosporanate.

EXAMPLE 2

Benzyl 7-β-benzaldimino-1-methylene-1-dethiacephalosporanate

Benzyl 7-β-amino-1-methylene-1-dethiacephalosporanate (1.72 g.) is treated with benzaldehyde (0.55 g.). The mixture is dissolved in benzene (30 ml.) and magnesium sulfate (2.0 g.) is added. The reaction mixture is allowed to stand at room temperature for two hours. The magnesium sulfate is removed by filtration and the filtrate is evaporated to afford benzyl 7-β-benzaldimino-1-methylene-1-dethiacephalosporanate.

EXAMPLE 3

Sodium 7α-(2'-thienylacetamido)-1-oxa-1-dethiacephalosporanate and sodium 7β-(2'-thienylacetamido)-1-oxa-1-dethiacephalosporanate Benzyl α-aminodiethylphosphonoacetate (0.594 g.) is dissolved in carbon tetrachloride (5.0 ml.) and added to ethyl thionoformate (0.1 g.) in carbon tetrachloride (5 ml.) cooled to 0° C. After the addition the reaction mixture is allowed to stir at room temperature overnight. The solvent is removed under reduced pressure to afford 0.602 g. of benzyl α-thioformamido-diethylphosphonoacetate as an oil.

I.R.: 3.1 $\mu$ (NH); 5.71 $\mu$ (C=O); 7.0 (C=S), 9.75 (P-O)

NMR: (CCl$_4$) $\tau$ : −0.1 (NH); 0.6, s(CH—C$^S$—); 2.73, s(C$_6$H$_5$); 3.98, d(j = 10 c.p.s.) (CH—P); 4.3 (—CH$_2$—C$_6$H$_5$) 5.93, m(O—CH$_2$—CH$_3$); 2.75, m(CH$_3$CH$_2$—O).

Step B: Benzyl α-(S-methylthioimidato)-diethylphosphonoacetate

Benzyl α-thioformamido-diethylphosphonoacetate (0.6 g.) is dissolved in acetone (20 ml.). Methyl iodide (0.5 ml.) and potassium carbonate (0.276 g.) are added and the mixture is stirred under N$_2$ overnight. The insoluble salts are filtered off, the filtrate is evaporated, the residue is dissolved in chloroform and filtered again. The filtrate is evaporated to afford 0.536 g. of benzyl α-(S-methylthioimidato)-diethylphosphonoacetate as an oil.

IR: 5.72 $\mu$ (C=O; 6.25 $\mu$ (C=N); 9.75 $\mu$ (P-O)

NMR:$\tau$:1.6, d(H—C=N); 2.7, s(C$_6$H$_5$); 4.83, s(CH$_2$—C$_6$—H$_5$);

5.43, d(HC—P); 5.93, m(O—CH$_2$—CH$_3$); 7.6, s(CH$_3$—S—); 8.73, t(CH$_3$—CH$_2$—O).

Step C: 1-(Benzyloxycarbonyldiethylphosphono)methyl-3-azido-4-(methylthio)-2-azetidinone Benzyl α-(S-methylthioimidato)-diethylphosphonoacetate (0.53 g.) is dissolved in dry methylenechloride (25 ml.) and placed under N$_2$. Azidoacetyl chloride (0.180 ml.) is then added dropwise over two minutes. The mixture is allowed to stir for three minutes and triethylamine (0.264 ml.) in dry methylene chloride (4.0 ml.) is added dropwise over 10 minutes. The resulting solution is allowed to stir for another 10 minutes and then is washed with a pH 7 buffer, dried and evaporated. The residue (0.745 g.) is chromatographed on silica gel using 50% ethyl acetate/benzene to afford 0.349 g. of 1-(benzyloxycarbonyldiethylphosphono)-methyl-3-azido-4-(methylthio)-2-azetidinone.

IR: 4.75 $\mu$ (azide); 5.6 $\mu$ (β-lactam C=O); 5.72 $\mu$ (ester C=O); 9.72 $\mu$ (P-O)

NMR: (CCl$_4$) τ: 2.73 s (C$_6$H$_5$); 4.83 s (CH$_2$-C$_6$H$_5$) 5.1 to 5.66 (β-lactam protons and CH-P-O) 5.91 (O-CH$_2$-CH$_3$); 7.9 (S-CH$_3$); 8.73 (CH$_3$-CH$_2$-O).

Step D: 1(Benzyloxycarbonyldiethylphosphono)methyl-3-azido-4-methylsulfonyl-2-azetidinone 1-(Benzyloxycarbonyldiethylphosphono)methyl-3-azido-4-(methylthio)-2-azetidinone (0.44 g.) is dissolved in methanol (20 ml.) and treated with N-bromoacetamide (0.52 g.) for two hours. Sodium thiosulfate (10 ml.; 0.1N) is then added and the mixture is allowed to stir for five minutes. At the end of this time, the reaction mixture shows no positive reaction to starch iodide paper. The reaction mixture is saturated with sodium chloride and extracted with methylene chloride. The methylene chloride extract is dried and evaporated. The residue is chromatographed to afford 1-(benzyloxycarbonyldiethylphosphono)methyl-3-azido-4-methylsulfonyl-2-azetidinone.

Step E: 1-(Benzyloxycarbonyldiethylphosphono)-methyl-3-azido-4-chloro-2-azetidinone 1-(Benzyloxycarbonyldiethylphosphono)methyl-3-azido-4-methylsulfonyl-2-azetidinone (0.446 g.) is dissolved in acetyl chloride (5 ml.). The mixture is allowed to stand for 10 minutes and the acetyl chloride is removed under reduced pressured to afford 1-(benzyloxycarbonyldiethylphosphono)methyl-3-azido-4-chloro-2-azetidinone.

IR: 4.75 μ (azide); 5.6 μ (β-lactam C=O); 5.72 μ (ester C=O); 9.72 μ (P-O).

The product of Step E can also be prepared by dissolving 1-(benzyloxycarbonyldiethylphosphono)methyl-3-azido-4-(methylthio)-2-azetidinone (0.44 g.) in methylene chloride (10 ml.) and treating with chlorine (0.110 g.) in methylene chloride (2.0 ml.). The mixture is allowed to stand for 10 minutes at room temperature. The solvent is removed under reduced pressure to afford the 1-(benzyloxycarbonyldiethylphosphono)methyl-3-azido-4-chloro-2-azetidinone as described in Step E.

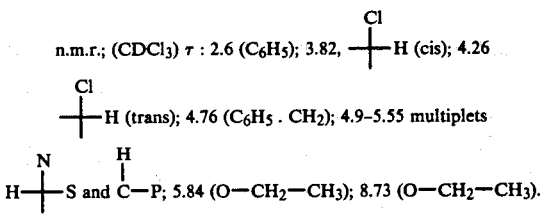

n.m.r.; (CDCl$_3$) τ : 2.6 (C$_6$H$_5$); 3.82, ⊥H (cis); 4.26 ⊥H (trans); 4.76 (C$_6$H$_5$ . CH$_2$); 4.9-5.55 multiplets H⊥S and C⊥P; 5.84 (O—CH$_2$—CH$_3$); 8.73 (O—CH$_2$—CH$_3$).

Step F: Cis and Trans 1-(benzyloxycarbonyldiethylphosphono)methyl-3-azido-4-(3'-acetoxy-2'-oxo)propyloxy-2-azetidinone 1-(Benzyloxycarbonyl-diethylphosphono)methyl-3-azido-4-chloro-2-azetidinone (0.43 g.) is dissolved in methylene chloride (10 ml.), 1,3-dihydroxy-2-propanone monoacetate (0.5 g.) and silver fluoroborate (0.3 g) are added and the mixture is stirred at room temperature for 0.5 hour. The mixture is diluted with CH$_2$Cl$_2$ (20ml), the silver salts are filtered off. The filtrate is washed once with 5% sodium bicarbonate and then with brine, dried and evaporated. The residue is chromatographed on silica gel to afford cis and trans 1-(benzyloxycarbonyl-diethylphosphono)methyl-3-azido-4-(3'-acetoxy-2'-oxo)propyloxy-2-azetidinone. i.r. 4.71 (azide); 5.59 (β-lactam C=O); 5.72 (esters and ketone carbonyls).

Step G: Benzyl 7α- (and β)-azido-1-oxadethiacephalosporanate

Cis and trans 1-(benzyloxycarbonyl-diethylphosphono)methyl-3-azido-4-(3'-acetoxy-2'-oxo)propyloxy-2-azetidinone (0.526 g.) is dissolved in anhydrous dimethoxyethane (20 ml.) under N$_2$ and treated with sodium hydride (0.047 g.; 57% in mineral oil). The reaction mixture is stirred for three hours at room temperature, taken up in benzene and washed once with a pH 7 buffer, and then with brine. The organic phase is dried and evaporated to give a residue which is chromatographed in silica gel to afford benzyl 7β-azido-1-oxadethiacephalosporanate, i.r. 4.71 (azide); 5.58 (β-lactam C=O); 5.75 (ester C=O), 6.09 (C=C).

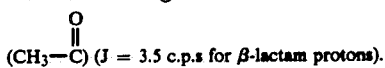

n.m.r. τ (CDCL$_3$): 2.56 (C$_6$—H$_5$); 4.69 (C$_6$H$_5$CH$_2$O); 4.8-5,6 (β-lactam,—CH$_2$—O—C(=O)—CH$_3$ and C-2 proton); 7.95

(CH$_3$—C(=O)) (J = 3.5 c.p.s for β-lactam protons).

and Benzyl 7α-azido-1-oxadethiacephalosporanate
i.r. 4.71 (azide); 5.58 (β-lactam C=O), 5.75 (ester C=O) 6.09 C=C).

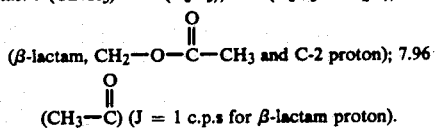

n.m.r. τ (CDCl$_3$): 2.59 (C$_6$H$_5$); 4.66 (C$_6$H$_5$ . CH$_2$O); 4.8-5.6 (β-lactam, CH$_2$—O—C(=O)—CH$_3$ and C-2 proton); 7.96

(CH$_3$—C(=O)) (J = 1 c.p.s for β-lactam proton).

Step H: Benzyl 7α-(and β)-amino-1-oxadethiacephalosporanate

Benzyl 7α- (and β)-azido-1-oxadethiacephalosporanate (0.733 g.) is dissolved in dioxane (30 ml.) Platinum oxide (0.5 g.) is added and the mixture is reduced under hydrogen at atmospheric pressure until the infrared spectrum of an aliquot shows the absence of the azide function. The dioxane is removed under reduced pressure, the residue is taken up in chloroform and filtered through a short column of silica gel G to remove the catalyst. The filtrate is evaporated to afford benzyl 7α-(and β)-amino-1-oxadethiacephalosporanate.

Step I: Benzyl 7α-(2'-thienylacetamido)-1-oxadethiacephalosporanate and benzyl 7β-(2'-thienylacetamido)-1-oxadethiacephalosporanate Benzyl 7α-(and β)-amino-1-oxadethiacephalosporanate (0.692 g.) is dissolved in methylene chloride (25 ml.), cooled to 0° C. and treated with pyridine (0.7 ml.) followed by 2-thienylacetyl chloride (0.33 g.). The mixture is allowed to stir at 0° C. for 30 minutes and then washed once with a pH 2 phosphate buffer and then with a pH 7 phosphate buffer. The organic phase is dried and evaporated to give a residue which on chromatography on silica gel affords benzyl 7β-(2-thienylacetamido)-1-oxadethiacephalosporanate and benzyl 7α-(2-thienylacetamido)-1-oxadethiacephalosporanate.

Step J: Sodium 7α-(2'-thienylacetamido)1-oxadiethacephalosporanate and Sodium 7β(2'-thienylacetamido)-1-oxadethiacephalosporanate Benzyl 7β-(2'-thienylacetamido)-1-oxadethiacephalosporanate (0.5 g) is dissolved in methanol (10 ml.). Water (3 ml.) is added and then 10% palladium on carbon catalyst (0.5 g.) is added and the mixture reduced at 40 lbs. of hydrogen pressure for one hour. The catalyst is filtered off, the filtrate is evaporated to about 2 ml., diluted to 10 ml. with water and one equivalent of sodium bicarbonate is added and the resulting solution is freeze dried to afford sodium 7β-(2'-thienylacetamido)-1-oxadethiacephalosporanate.

n.m.r. ($D_2O$, DSS) τ: 2.73 and 3.03 ( 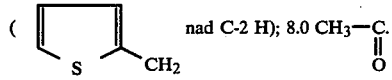 ); 4.56

(C-7H) 4.83 (C-6H, J = 4 c.p.s); 5.66 ($CH_2$—OAc); 6.16

( 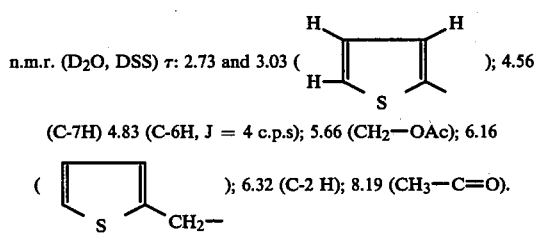 ); 6.32 (C-2 H); 8.19 ($CH_3$—C=O).

Similar reductive cleavage of the benzyl ester of benzyl 7α-(2'-thienylacetamido)-1-oxadethiacephalosporanate affords sodium 7α-(2'-thienylacetamido)-1-oxadethiacephalosporanate.

EXAMPLE 3A

7β-Amino-1-oxadethiacephalosporanate

Benzyl 7β-azido-1-oxadethiacephalosporanate (0.100g) is dissolved in 4 ml. of dioxane and 2 ml. of $H_2O$ and 0.020 g. of 10% Pd/C (Bolhofer) catalyst is added and the mixture is reduced under 40 lbs $H_2$ for 55 minutes. The catalyst is filtered off and the filtrate is freeze-dried to give 7β-amino-1-oxadethiacephalosporanate.

i.r. 5.63 β-lactam, 5.71 (shoulder, ester carbonyl), 6.0 (amide); 6.25 (carboxylate).

EXAMPLE 3B

7β-(2-Thienylacetamido)-1-oxadethiacephalosporanic acid

7β-Amino-1-oxadethiacephalosporanic acid (0.070 g) is dissolved in 4 ml. acetone and 2 ml. $H_2O$ and 0.047 g. of $NaHCO_3$ is added and the mixture is cooled to 0°. 2-Thienylacetyl chloride (0.045 g.) is added and the mixture is stirred at 0° for ½ hour. The acetone is removed under reduced pressure and the residue is diluted with 10 ml $H_2O$ and extracted twice with ethyl acetate. The EtOAc extract is washed once with water and the combined aqueous layers are taken to pH 2 with pH 2 phosphate buffer and extracted twice with ethyl acetate. The ethyl acetate extract is dried and evaporated to give 0.068 g of 7β-(2-thienylacetamido)-1-oxadethiacephalosporanic acid.

i.r. 5.60 (β-lactam); 5.78 (ester carbonyl); 6.03 (amide); 6.5 (amide II).

n.m.r. τ ($CDCl_3$); 2.71 and 3.03 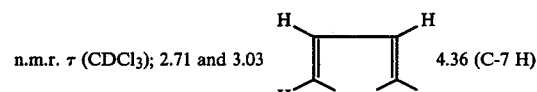 4.36 (C-7 H)

4.95 (C-6 H); 5.70 ($CH_2$—O—C—$CH_3$); 6.08 and 6.1
$\qquad\qquad\qquad\qquad\quad\;\;\;\parallel$
$\qquad\qquad\qquad\qquad\quad\;\;\;O$ ( 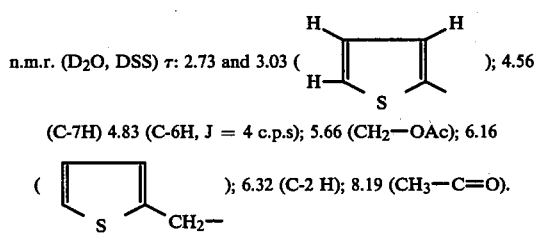 nad C-2 H); 8.0 $CH_3$—C.
$\qquad\qquad\qquad\qquad\qquad\qquad\qquad\;\;\parallel$
$\qquad\qquad\qquad\qquad\qquad\qquad\qquad\;\;O$

EXAMPLE 4

Sodium 7β-(2'-thienylacetamido)-1-methylene-1-dethia-3-methyl-3-cephem-4-carboxylate By substituting for the 4- methylene-5-acetoxyvaleraldehyde of Step F of Example 1, an equimolar quantity of 4-methylenevaleraldehyde and by following substantially the procedures described in Steps F-L of Example 1, there is obtained sodium 7β-(2-thienylacetamido)-1-methylene-1-dethia-3-methyl-3-cephem-4-carboxylate.

Preparation of 4-methylenevaleraldehyde

Step A: 4-Methylenevaleronitrile

Dry acetonitrile (5.0 g.) is placed in a 1-liter flask under $N_2$, dry tetrahydrofuran (200 ml.) is added and the mixture is cooled to −78° C. 38 ml. of a 23.1% solution of n-butyllithium is then added dropwise over 15 min. to the reaction mixture and stirring is continued for another 40 minutes. The reaction mixture is allowed to warm to −25° C. and cuprous iodide (23.8 g.) is then added and stirring is continued for another 15 minutes at −25° C. Methallyl chloride (11.3 g.) in tetrahydrofuran (20 ml.) is then added dropwise over 5 minutes and the mixture is stirred at −25° C. for one hour. Aqueous ammonium chloride is then added and the product is extracted with ether. The ether extract is washed once with brine, dried and evaporated under a Vigreaux column at atmospheric pressure. The residue is then distilled to afford 10.2 g. of 4-methylenevaleronitrile b.p. 165°-173° C.

IR: 4.45 μ (C≡N); 6.02 μ (C=C); 11.1 μ (C=C)

NMR: τ: 5.2 m(C=$\underline{CH_2}$); 7.63, m(—$\underline{CH_2}$—$\underline{CH_2}$—); 8.2, ($\underline{CH_3}$—).

Step B: 4-methylenevaleraldehyde

4-Methylenevaleronitrile (3.0 g.) is dissolved in benzene (10 ml.) and placed under $N_2$. 25 ml. of 20% solution of diisobutylaluminum hydride in hexane is added dropwise so that the reaction mixture is maintained at 40°-45° C. After the addition, the reaction is maintained at 40° C. for ½ hour and then poured into ice cold 2.5 N-hydrochloric acid. The organic phase is separated and the aqueous phase is washed with ether 3 times. The combined organic extract is dried and evaporated using a Vigreaux column. The residue is distilled at atmospheric pressure through a short Vigreaux column to afford 2.45 g. of 4-methylenevaleraldehyde b.p. 135°-142° C.

H
|
IR: 3.7μ (C=O); 5.75μ (C=O); 6.02μ (C=C) and 11.1μ (C=C).

EXAMPLE 5

Sodium 7β-(2'-thienylacetamido)-3-carbamoyloxymethyl-1-methylene-1-dethia-3-cephem-4-carboxylate Step A: 4,4,6-Trimethyl-5,6-dihydro-2-(4'-hydroxy-3'-methylene)-butyl-1,3(4 H)-oxazine 4,4,6-Trimethyl-5,6-dihydro-2-(4'-acetoxy-3'-methylene)-butyl-1,3(4 H)-oxazine (12.5 g.) is dissolved in tetrahydrofuran (100 ml.). Water (50 ml.) is added and then 20 ml. of 2.5 N sodium hydroxide is added dropwise for over one hour. The reaction mixture is allowed to stir at room temperature for another four hours. Ether (200 ml. is then added and the aqueous layer is separated and extracted once with ether (100 ml.). The combined ether extract is washed with brine, dried and evaporated to afford 4,4,6-trimethyl-5,6-dihydro-2-(4'-hydroxy-3'-methylene)-butyl-1,3 (4 H)-oxazine.

Step B: 4,4,6-Trimethyl-5,6-dihydro-2-(4'-carbamoyloxy-3'-methyl)-butyl-1,3 (4 H)-oxazine 4,4,6-Trimethyl-5,6-dihydro-2-(4'-hydroxy-3'-methylene)-butyl-1,3(4 H)-oxazine(21.2 g.) is dissolved in benzene (100 ml.). Sodium cyanate (13.0 g.) is added and then trifluoroacetic acid (22.8 g.) is added dropwise for over one hour. The reaction mixture is stirred for another two hours. Water (20 ml.) is added and the aqueous phase is separated. The organic phase is dried and evaporated to afford 4,4,6-trimethyl-5,6-dihydro-2-(4'-carbamoyloxy-3'-methyl )-butyl-1,3(4 H)-oxazine.

Step C: 4-Methylene-5-carbamoyloxyvaleraldehyde 4,4,6-Trimethyl-5,6-dihydro-2-(4'-carbamoyloxy-3'-methylene)-butyl-1,3(4 H)-oxazine (12.5 g.) is dissolved in tetrahydrofuran (100 ml.). Water is added until a slight turbidity results. The mixture is cooled to −30° C. and sodium borohydride (1.0 g.) is added in four equal amounts. After stirring for ½ hour at −30° C. the reaction mixture is allowed to warm to room temperature and treated with a dilute hydrochloric acid. The reaction mixture is diluted with ether (300 ml.) and washed once with water and then with brine. The organic phase is dried and evaporated to afford the tetrahydro-oxazine which is refluxed with 100 ml. of 5% oxalic acid solution for ½ hour. The reaction mixture is extracted with ether and the ether extract is dried and evaporated to afford 4-methylene-5-carbamoyloxyvaleraldehyde.

Step D: Sodium 7β-(2'-thienylacetamido)-3-carbamoyloxymethyl-1-methylene-1-dethia-3-cephem-4-carboxylate By substituting for the 4-methylene-5-carbamoyloxyvaleraldehyde of Example 1, Step F, an equimolar quantity of 4-methylene-5-carbamoyloxyvaleraldehyde and by following substantially the procedures described in Example 1, Steps F-L there is obtained sodium 7β-(2'-thienylacetamido)-3-carbamoyloxymethyl-1-methylene-1-dethia-3-cephem-4-carboxylate.

By substituting for the sodium cyanate trifluoroacetic acid of Example 5, Step B, an equimolar quantity of methylisocyanate or N,N-diethylcarbamoyl chloride and by following substantially the procedures described in Example 5,Steps B-D, there is obtained respectively sodium 7β-(2'-thienylacetamido-3-(N-methylcarbamoyloxymethyl)1methylene-1-dethia-3-cephem-4-carboxylate and sodium 7β-(2'-thienylacetamido)-3-(N,N-diethylcarbamoyloxymethyl)-1-methylene-1-dethia-3-cephem-4-carboxylate.

EXAMPLE 6

Sodium 7β-(2'-thienylacetamido)-3-carbamoyloxymethyl-1-oxa-1-dethia-3-cephem-4carboxylate Step A: 1-Acetoxy-3-carbamoyloxy-2-propanone To a stirred mixture of 1-acetoxy-3-hydroxy-2-propanone (10.8 g., 0.1 mole) and sodium cyanate (13.0 g., 0.2 mole) in benzene (50 ml.) is slowly added trifluoroacetic acid (15.5 ml., 0.21 mole). The reaction mixture is stirred for three hours, then water (15 ml.) is added. The organic layer is separated, dried and the solvent removed under reduced pressure to afford 1-acetoxy-3-carbamoyloxy-2-propanone.

Step B: 1-Hydroxy-3-carbamoyloxy-2-propanone

Aqueous sodium hydroxide (35 ml. of a 2.5 N solution) is added dropwise over 30 minutes to a stirred solution of 1-acetoxy-3-carbamoyloxy-2-propanone (14.9 g., 0.085 g.) in methanol (10 ml.). The methanol is evaporated under reduced pressure and the aqueous residue extracted with chloroform (3×25 ml.). The combined extracts are dried, and the solvent is removed in vacuo to afford 1-hydroxy-3-carbamoyloxy-2-propanone.

Step C: Sodium 7β-(2'-thienylacetamido)-3-carbamoyloxy-1-oxy-1-dethia-3-cephem-4-carboxylate By substituting for the 1,3-dihydroxy-2-propanone monoacetate of Example 3, Step F, an equimolar quantity of 1-hydroxy-3-carbamoyloxy-2-propanone and by following the procedures described in Example 3, Steps F-J, there is obtained sodium 7β-(2'-thienylacetamodo)-3-carbamoyloxymethyl-1-oxa-1-dethia-3-cephem-4-carboxylate.

EXAMPLE 7

Sodium 7β-(2'-thienylacetamido)-3-acetoxymethyl-1-aza-1-dethia-3-cephem-4-carboxylate Step A: 1-Azido-3-acetoxyacetone 1-Chloro-3-acetoxyacetone (15.05 g.) is dissolved in tetrahydrofuran (50 ml.) and water (25 ml.) is added. Sodium azide (8.7 g.) is added and the mixture is allowed to stir overnight at room temperature. The reaction mixture is diluted with ether (200 ml.) and the aqueous phase is separated. The organic phase is washed once with brine, then dried and evaporated to give 1-azido-3-acetoxyacetone.

STEP B: 1-Amino-3-acetoxyacetone

1-Azido-3-acetoxyacetone (15.7 g.) is dissolved in ethylacetate (200 ml.). The 10% palladium on carbon catalyst (1.0 g.) is added; the mixture is reduced under hydrogen at atmospheric pressure until the infrared spectrum of an aliquot indicates the absence of the azide. The catalyst is filtered off and the filtrate is evaporated to afford 1-amino-3-acetoxy acetone.

Step C: Sodium 7β-(2'-thienylacetamido)-3-acetoxy-methyl-1-aza-1-dethia-3-cephem-4-carboxylate By substituting for the 1,3-dihydroxy-2-propanone monoacetate of Example 3, Step F, an equimolar quantity of 1-amino-3-acetoxyacetone and by following substantially the procedures described in Example 3, Steps F-J, there is obtained sodium 7β-(2'thienylacetamido)-3-acetoxymethyl-1-aza-1-dethia-3-cephem-4-carboxylate.

EXAMPLE 8

Sodium 7β-(2'-thienylacetamido)-3-acetoxymethyl-N-methyl-1-aza-1-dethia-3-cephem-4-carboxylate Step A: 1-(N-methyl)amino-3-acetoxyacetone To 1-amino-3-acetoxyacetone (13.1 g.) is added benzaldehyde (10.6 g.) dropwise with cooling, 10 minutes after the addition, benzene (300 ml.) is added and the solution is dried over $MgSO_4$ for two hours. The $MgSO_4$ is removed and the solvent is evaporated to afford 1-benzaldimino-3-acetoxyacetone. This is redissolved in benzene (200 ml.) and treated with 15 g. of dimethyl sulfate, added dropwise. The resulting solution is heated slowly to reflux and then refluxed for one hour. The benzene is removed under reduced pressure. The residue is taken up in water (200 ml.) and treated with 1 equivalent of 1 N sodium hydroxide, added at such a rate that the pH remains between 4 and 8. After the addition is complete, the reaction mixture is extracted with ether and the ether extract is dried. Anhydrous hydrochloric acid is then bubbled into the ether extract and the precipitated amine hydrochloride is separated. The amine hydrochloride is dissolved in water and the solution is taken to pH 7.5 and extracted with ether. The ether extract is dried and evaporated to afford 1-(N-methyl)-amino-3-acetoxyacetone.

Step B: Sodium 7β-(2'-thienylacetamido)-3-acetoxymethyl-N-methyl-1-aza-1-dethia-3-cephem-4-carboxylate By substituting for the 1,3-dihydroxy-2-propanone monoacetate of Example 3, Step F, an equimolar quantity of 1-(N-methyl)amino-3-acetoxyacetone and by following substantially the procedures described in Example 3, Steps F-J, there is obtained sodium 7β-(2'-thienylacetamido)-3-acetoxymethyl-N-methyl-1-aza-1-dethia-3-cephem-4-carboxylate.

EXAMPLE 9

Sodium 7β-(2'-thienylacetamido)-3-hydroxymethyl-1-methylene 1-dethia-3-cephem-4-carboxylate To a solution of sodium 7β-(2'-thienylacetamido)-3-acetoxymethyl-1-methylene-1-dethia-3-cephem-4-carboxylate (1.0 g.) in water (15.0 ml.) is added acetylesterase. The pH is adjusted to 6.0 and maintained around this level for 15 hours. The solution is then passed through a column containing phenolic amine (in the acetate form) and eluted with aqueous 0.1 M acetic acid which has been adjusted to pH 5.5 by addition of pyridine. The fractions collected are adjusted to pH 8 by the addition of sodium hydroxide and this alkaline mixture is evaporated in vacuo to afford sodium 7β-(2'-thienylacetamido)-3-hydroxymethyl-1-methylene-1-dethia-3-cephem-4-carboxylate.

EXAMPLE 10

Sodium 7β-(2'-thienylacetamido)-3-(pyridinium-methyl)-1-methylene-1-dethia-3-cephem-4-carboxylate A solution of sodium 7β-(2'-thienylacetamido)-3-hydroxymethyl-1-methylene-1-dethia-3-cephem-4-carboxylate (1.0 g.) is brought to pH 2.5. Pyridine (8.0 ml.) is added and the solution is allowed to stand overnight at 45° C. The reaction mixture is then lyophilized and the residue is dissolved in water and passed through a polystyrene trimethylbenzylammonium anion exchange resin (43% $H_2O$). Selected fractions are diluted with water and lyophilized to afford substantially pure sodium 7β-(2'-thienylacetamido)-3-(pyridinium-methyl)-1-methylene-1-dethia-3-cephem-4-carboxylate.

EXAMPLE 11

Sodium 7β-(2'-thienylacetamido)-3-(5-methyl-1,3,4-thiadiazol-2-ylthiomethyl)-1-methylene-1-dethia-3-cephem-4-carboxylate A mixture of benzyl 7β-(2'-thienylacetamido)-1-methylene-1-dethiacephalosporanate (0.654 g.) and 5-methyl-1,3,4-thiadiazolyl-2-thiol (0.37 ml.) in a mixture of one part acetone and one part water (10 ml.) is stirred at room temperature and a 10% sodium hydroxide solution (2.0 ml.) is added with stirring. The mixture is then heated in a sealed tube for 100 hours and the resulting mixture is concentrated in vacuo to afford the substantially pure product.

By substituting for 5-methyl-1,3,4-thiadiazolyl-2-thiol an equimolar quantity of N-methyl tetrazolylthiol and by following substantially the procedure described above there is obtained sodium 7β-(2'-thienylacetamido)-3-(N-methyltetrazolylthiomethyl)-1-methylene-1-dethia-3-cephem-4-carboxylate.

EXAMPLE 12

Benzyl 7β-amino-1-benzyloxycarbonylamino-dethiacephalosporanate and benzyl 7α-amino-1-benzyloxycarbonylamino-dethiacephalosporanate A. 2,2-Dimethyl-4-azidomethyl-1,3-dioxolane 15.05 g. of 2,2-dimethyl-4-chloromethyl-1,3-dioxolane is dissolved in 100 ml. DMF and 6.5 g. of $NaN_3$ are added. The mixture is stirred at 50° overnight, cooled to room temperature, diluted with 300 ml. $C_6H_6$ and washed 5 times with water. The organic phase is dried and evaporated under reduced pressure to give 2,2-dimethyl-4-azidomethyl-1,3-dioxolane.

B. 2,2-dimethyl-4-aminomethyl-1,3-dioxolane 15.7 g. of 2,2-dimethyl-4-azidomethyl-1,3-dioxolane is dissolved in 200 ml. $C_6H_6$. 1.5 g. of $PtO_2$ is added and the mixture is reduced under hydrogen at 40 lbs. pressure, until i.r. of an aliquot shows absence of azide.

The catalyst is filtered off and the filtrate is evaporated to give 2,2-dimethyl-4-aminomethyl-1,3-dioxolane.

C.
1-(benzyloxycarbonyldiethylphosphono)-methyl-3-azido-4-(2,2-dimethyl-1,3-dioxolanyl)-methylamino-azetidin-2-one 0.156 g. of potassium is dissolved in 10 ml. of tBuOH under $N_2$. To this is added 0.524 g. of 2,2-dimethyl-4-aminomethyl-1,3-dioxolane and the mixture is stirred at room temperature for ½ hour. 1.722 g. of 1-(benzyloxycarbonyldiethylphosphono)-methyl-3-azido-4-chloro-azetidin-2-one dissolved in 10 ml. of tBuOH is added dropwise over 15 minutes and the mixture is stirred at room temperature until an aliquot shows a neutral reaction to pH paper.

The reaction mixture is diluted with 100 ml. $C_6H_6$ and washed once with pH 3 buffer and then with pH 7 phosphate buffer. The organic phase is dried and evaporated. The residue is chromatographed on silica gel to give 1-(benzyloxycarbonyldiethylphosphono)-methyl-3-azido-4-(2,2-dimethyl-1,3-dioxolanyl)-methylamino-azetidin-2-one.

D.
1-(benzyloxycarbonyldiethylphosphono)-methyl-3-azido-4-(N-2,2-dimethyl-1,3-dioxolanylmethyl)-benzyloxycarbonylamino-azetidin-2-one 1.05 g. of 1-(benzyloxycarbonyldiethylphosphono)-methyl-3-azido-4-(2,2-dimethyl-1,3-dioxolanyl)-methylaminoazetidin-2-one is dissolved in 50 ml. $CH_2Cl_2$, cooled to 0° and treated with 0.474 g. (3 eq.) pyridine. Benzyloxycarbonyl chloride (0.680, 2 eq.) is then added and the mixture is stirred at 0° for 15 minutes and then at room temperature for 3 hours. The reaction mixture is diluted with $CH_2Cl_2$, washed once with pH 7 phosphate buffer, then pH 3 phosphate buffer and then again with pH 7 phosphate buffer. The organic phase is dried and evaporated. The residue is chromatographed on silica gel (60 g.) to give 1-(benzyloxycarbonyldiethylphosphono)-methyl-3-azido-4-(N-2,2-dimethyl-1,3-dioxolanylmethyl)-benzyloxycarbonylamino-azetidin-2-one.

E.
1-(benzyloxycarbonyldiethylphosphono)-methyl-3-azido-4-(N-2,3-dihydroxypropyl)-benzyloxycarbonylamino-azetidin-2-one 1-(Benzyloxycarbonyldiethylphosphono)-methyl-3-azido-4-(N-2,2-dimethyl-1,3-dioxolanylmethyl)-benzyloxycarbonylamino-azetidin-2-one (1 g.) is dissolved in 10 ml. of THF, 2 ml. $H_2O$ is added and then 0.5 ml. of 7% aqueous $HClO_4$ is added. The mixture is allowed to stand at room temperature for 2¼ hours. The mixture is diluted with $CHCl_3$ (50 ml.) and washed once with pH 7 buffer, then with brine and dried and evaporated to give a residue which is 1-(benzyloxycarbonyldiethylphosphono)-methyl-3-azido-4-(N-2,3-dihydroxypropyl)-benzyloxycarbonylamino-azetidin-2-one.

F.
1-(benzyloxycarbonyldiethylphosphono)-methyl-3-azido-4-(N-2-hydroxy-3-acetoxypropyl)-benzyloxycarbonylaminoazetidin-2-one 0.619 g. of 1-(benzyloxycarbonyldiethylphosphono)-methyl-3-azido-4-(N-2,3-dihydroxypropyl)-benzyloxycarbonylamino-azetidin-2-one is dissolved in 15 ml. of $CH_2Cl_2$ and cooled to 0° C. Pyridine (0.158 g., 2 eq.) and acetic anhydride (0.102 g., 1.1 eq.) is added and the mixture is stirred at 0° C. for 15 minutes and then at room temperature for one hour. The reaction mixture is diluted with $CH_2Cl_2$ and washed once with pH 7 buffer, then with pH 3 buffer and once again with pH 7 buffer. The organic phase is dried and evaporated. The residue is chromatographed on silica gel to give 1-(benzyloxycarbonyldiethylphosphono)-methyl-3-azido-4-(N-2-hydroxy-3-acetoxypropyl)-benzyloxycarbonylaminoazetidin-2-one.

G.
1-(benzyloxycarbonyldiethylphosphono)-methyl-3-azido-4-(N-2-oxo-3-acetoxypropyl)-benzyloxycarbonylaminoazetidin-2-one 1-Benzyloxycarbonyldiethylphosphono)methyl-3-azido-4-(N-2-hydroxy-3-acetoxypropyl)-benzyloxycarbonylamino-azetidin-2-one (0.661 g.) is dissolved in 2 ml. of $CH_2Cl_2$. Chromium trioxide (0.6 g.) is added to a magnetically stirred solution of 0.949 g. pyridine in 15 ml. of methylene chloride under $N_2$. The solution is stirred for 15 minutes at room temperature at the end of which the solution of the alcohol in $CH_2Cl_2$ prepared above is added in one portion. Stirring is continued for 16 minutes, the solution is decanted from the black residue which is washed with 20 ml. of $CH_2Cl_2$. The combined organic phase is washed once with pH 3 buffer then with pH 7 buffer and then dried and evaporated. The residue is chromatographed on silica gel to give 1-(benzyloxycarbonyl-diethylphosphono)- methyl-3-azido-4-(N-2-oxo-3-acetoxypropyl)-benzyloxycarbonylamino-azetidin-2-one.

H.
benzyl-7α-azido-1-(benzyloxycarbonylamino)dethiacephalosporanate and its 7β-azido epimer 1-(Benzyloxycarbonyldiethylphosphono)-methyl-3-azido-4-(N-2-oxo-3-acetoxypropyl)-benzyloxycarbonylamino-azetidin-2-one (0.65 g.) is dissolved in 20 ml. of anhydrous DME under $N_2$ and treated with 0.047 g. of sodium hydride (57% in mineral oil). The reaction mixture is stirred for 3 hours at room temperature. The reaction mixture is diluted with $C_6H_6$ and washed once with pH 7 buffer and then with brine. The organic phase is dried and evaporated to give a residue which on chromatography on silica gel gives benzyl-7α-azido-1-(benzyloxycarbonylamino)dethiacephalosporanate and its 7β-azido epimer.

I. benzyl
7β-amino-1-(benzyloxycarbonylamino)-dethiacephalosporanate and benzyl
7α-amino-1-(benzyloxycarbonylamino)-dethiacephalosporanate 0.800 g. of the benzyl 7β-azido-1-(benzyloxycarbonylamino)-dethiacephalosporanate is dissolved in 50 ml. of $C_6H_6$. 0.400 g. of $PtO_2$ is added and the mixture is reduced under $H_2$ at 40 lbs. pressure until an aliquot shows absence of azide by its i.r. spectrum.

The catalyst is filtered off and the filtrate is evaporated to give 7β-amino-1-(benzyloxycarbonylamino)-dethiacephalosporanate.

Similarly, benzyl 7α-azido-1-(benzyloxycarbonylamino)-dethiacephalosporanate is reduced to benzyl 7α-amino-1-(benzyloxycarbonylamino)-dethiacephalosporanate.

EXAMPLE 13 benzyl
7β-(2-thienylacetamido)-1-benzyloxycarbonylaminodethiacephalosporanate 0.479 g. of benzyl 7β-amino-1-(benzyloxycarbonyl)-dethiacephalosporanate is dissolved in 25 ml. of $CH_2Cl_2$, cooled to 0° C. and treated with 0.160 ml. of pyridine and 0.160 g. of thienylacetyl chloride.

The reaction mixture is stirred at 0° C. for 15 minutes then diluted with $CH_2Cl_2$ and washed once with pH 7 buffer then with pH 3 buffer and then with pH 7 buffer. The organic phase is dried and evaporated to give a residue which is chromatographed on silica gel to give benzyl 7β-(2-thienylacetamido)-1-benzyloxycarbonylamino-dethiacephalosporanate.

EXAMPLE 14

7β-(2-thienylacetamido)-1-aminodethiacephalosporanic acid 0.400 g. of benzyl 7β-(2-thienylacetamido)-1-benzyloxycarbonylaminodethiacephalosporanate is dissolved in 5 ml. of dioxane and 2 ml. of $H_2O$ is added. 0.400 g. of 10% Pd/C (Bolhofer catalyst) is added and the mixture is reduced under 40 lbs. pressure for 1 hour. The catalyst is filtered off and washed with water. The filtrate and washings are extracted with $CHCl_3$ and the aqueous phase is freeze-dried to give 7β-(2-thienylacetamido)-1-aminodethiacephalosporanic acid.

EXAMPLE 15 benzyl
7α-(4-nitrobenzalimino)-1-benzyloxycarbonylaminodethiacephalosporanate

Benzyl 7α-amino-1-(benzyloxycarbonylamino)-dethiacephalosporanate (0.489 g.) is dissolved in 20 ml. $CHCl_3$ and treated with 0.151 g. of p-nitrobenzaldehyde. 3 g. of anhydrous $MgSO_4$ is added and the mixture is stirred at room temperature for 2 hours and filtered. The filtrate is evaporated to give benzyl 7α-(4-nitrobenzalimino)-1-benzyloxycarbonylaminodethiacephalosporanate.

EXAMPLE 16 benzyl
7β-(4-nitrobenzalimino)-1-benzyloxycarbonylaminodethiacephalosporanate and benzyl
7α-(4-nitrobenzalimino-1-benzyloxycarbonylaminodethiacephalosporanate 0.612 g. of the benzyl 7α-(4-nitrobenzalimino)-1-benzyloxycarbonylaminodethiacephalosporanate is dissolved in 25 ml. of anhydrous THF under $N_2$ and cooled to −78° C. 0.5 ml. of a 2 M solution of phenyl lithium in $C_6H_6/Et_2O$ is added dropwise over 2 minutes. The mixture is stirred a further 2 minutes and 20 ml. of DMF are added dropwise over 3 minutes followed by 0.066 g. of HOAc and 0.100 ml. of $H_2O$ in 5 ml. of THF. The reaction mixture is diluted with $C_6H_6$ and washed once with pH 7 phosphate buffer and then with water, and then 4 times with brine. The organic phase is dried and evaporated to give a mixture of benzyl 7β-(4-nitrobenzalimino)-1-benzyloxycarbonylaminodethiacephalosporanate and its epimer at C-7.

EXAMPLE 17 benzyl
7β-amino-1-benzyloxycarbonylaminodethiacephalosporanate and benzyl
7α-amino-1-benzyloxycarbonylaminodethiacephalosporanate 2,4-Dinitrophenylhydrazine (0.198 g.) and p-toluenesulfonic acid monohydrate (0.190 g.) is added to 5 ml. of EtOH and the mixture is stirred at room temperature for 1 hour. The mixture of benzyl 7β-(4-nitrobenzalimino)-1-benzyloxycarbonylaminodethiacephalosporanate and its epimer at C-7 (0.612 g.) is dissolved in 2 ml. EtOH and added to the above mixture and stirred for ½ hour. The orange solid is filtered off and the filtrate is evaporated under reduced pressure. The residue is taken up in $CH_2Cl_2$ and washed with pH 8 phosphate buffer, dried and evaporated to give benzyl 7β-amino-1-benzyloxycarbonylamino-dethiacephalosporanate and its C-7 epimer.

EXAMPLE 18 benzyl
7β-(2-thienylacetamido)-1-benzyloxycarbonylamino-dethiacephalosporanate and benzyl
7α-(2-thienylacetamido)-1-benzyloxycarbonylamino-dethiacephalosporanate The mixture of benzyl 7β-amino-1-benzyloxycarbonylamino-dethiacephalosporanate and its C-7 epimer is acylated with thienyl-acetyl chloride and pyridine as described for the 7β-isomer and the resulting mixture is chromatographed on silica gel to give benzyl 7β-(2-thienylacetamido)-1-benzyloxycarbonylamino-dethiacephalosporanate and benzyl 7α-(2-thienylacetamido)-1-benzyloxycarbonylamino-dethiacephalosporanate.

EXAMPLE 19

7β-(2-thienylacetamido)-1-methylamino-dethiacephalosporanic acid 0.524 g. of 7β-(2-thienylacetamido)-1-aminodethiacephalosporanic acid is dissolved in 4.5 ml. of AcOH, 2.5 ml. of $H_2O$, 0.4 g. of 35% HCHO and 0.3 g. of $PtO_2$ are added and the mixture is reduced under $H_2$ at 40 lbs. for ½ hour. The catalyst is filtered off and the filtrate is freeze-dried to give 7β-(2-thienylacetamido)-1-methylamino-dethiacephalosporanic acid.

EXAMPLE 20 cis- and
trans-1-(1-benzyloxycarbonyl-2-chloromethyl-3-acetoxy-prop-1-enyl)-3-azido-4-chloroazetidin-2-one To a solution of 388 mg. of benzyl-7-azidocephalosporanate (mixture of C-7 epimers) in 10 ml. of anhydrous carbon tetrachloride is added 2.2 equivalents of chlorine in $CCl_2$. After 0.5 hours at room temperature, the solvent is removed in vacuo to give a mixture of cis- and trans-1-(1-benzyloxycarbonyl-2-chloromethyl-3-acetoxy-prop-1-enyl)-3-azido-4-chloroazetidin-2-one.

EXAMPLE 21 benzyl 7α-azido-1-benzylamino-dethiacephalosporanate and benzyl 7β-azido-1-benzylamino-dethiacephalosporanate A solution of 107 mg. (1 mmole) of benzylamine in 2 ml. of N,N-dimethylformamide is added to a suspension of 276 mg. (2 mmoles) of potassium carbonate in 5 ml. of N,N-dimethylformamide containing 427 mg. (1 mmole) of 1-(1-benzyloxycarbonyl-2-chloromethyl-3-acetoxyprop-1-enyl)-3-azido-4-chloro-azetidin-2-one. The reaction mixture is stirred at room temperature overnight under nitrogen and poured onto 100 g. of ice. The organic matter is extracted with 5×20 ml. of 1:1 ether-petroleum ether mixture. Removal of the solvent from the extracts, and drying over anhydrous magnesium sulfate, gives a residue, which on chromatography on silica gel, gives benzyl 7α-azido-1-benzylamino-dethiacephalosporanate, and benzyl 7β-azido-1-benzylamino-dethiacephalosporanate.

EXAMPLE 22 benzyl 7α-azido-1-methylamino-dethiacephalosporanate and benzyl 7β-azido-1-methylamino-dethiacephalosporanate A solution of 1 equivalent of methylamine in anhydrous N,N-dimethylformamide is added to a solution of 427 mg. (1 mmole) of 1-(1-benzyloxycarbonyl-2-chloromethyl-3-acetoxy-prop-1-enyl)-3-azido-4-chloro-azetidin-2-one in 5 ml. of N,N-dimethylformamide, containing 2 equivalents of potassium carbonate. The reaction mixture is stirred under nitrogen at room temperature 1 day, poured into ice-cold water and extracted with a mixture of ether-petroleum ether. The combined organic layers are dried over anhydrous magnesium sulfate. The residue, obtained by removing the solvent, is chromatographed on silica gel to give benzyl 7α-azido-1-methylamino-dethiacephalosporanate and benzyl 7β-azido-1-methylamino-dethiacephalosporanate.

EXAMPLE 23 benzyl 7α-amino-1-benzylamino-dethiacephalosporanate 246 mg. of benzyl 7α-azido-1-benzylamino-dethiacephalosporanate is reduced under hydrogen in benzene, using 59 mg. of platinum oxide as catalyst, at atmospheric pressure, until azide band disappears. The catalyst is filtered and washed with benzene. The solvent removal from the filtrate gives benzyl 7α-amino-1-benzylamino-dethiacephalosporanate.

Similarly, benzyl 7α-azido-1-methylamino-dethiacephalosporanate is reduced to give benzyl 7α-amino-1-methylaminodethiacephalosporanate.

Analogously, benzyl 7β-azido-1-benzylamino-dethiacephalosporanate is reduced to give benzyl 7β-amino-1-benzyl-amino-dethiacephalosporanate.

Also, benzyl 7β-azido-1-methylamino-dethiacephalosporanate gives benzyl 7β-amino-1-methylamino-dethiacephalosporanate.

EXAMPLE 24 benzyl 7α-nitrobenzaldimino-1-benzylamino-dethiacephalosporanate

To a solution of 152 mg. (1 mmole) of p-nitrobenzaldehyde in 4 ml. of chloroform is added a solution of 435 mg. (1 mmole) of benzyl 7α-amino-1-benzylamino-dethiacephalosporanate in 6 ml. of chloroform. 1.5 g. of anhydrous magnesiumsulfate is added and the mixture is stirred for 2 hours. The solid is filtered and washed with chloroform. The solvent removal from the filtrate gives benzyl 7α-p-nitrobenzaldimino-1-benzylamino-dethiacephalosporanate.

Similarly, condensation of benzyl 7α-amino-1-methylaminodethiacephalosporanate with p-nitrobenzaldehyde gives benzyl 7α-p-nitrobenzaldimino-1-methylamino-dethiacephalosporanate.

EXAMPLE 25 benzyl 7α-p-nitrobenzaldimino-1-benzylamino-dethiacephalosporanate and benzyl 7β-nitrobenzaldimino-1-benzylaminodethiacephalosporanate To a solution of 523 mg. of benzyl 7α-p-nitrobenzaldimino-1-benzylamino-dethiacephalosporanate in 10 ml. of anhydrous tetrahydrofuran is added under nitrogen 0.435 ml. of 2.3 M solution of phenyl lithium at −78° C. 10 ml. of N,N-dimethylformamide is slowly added followed by a mixture of 30 μl. of water and 76 μl. of glacial acetic acid in 2 ml. of tetrahydrofuran. The reaction mixture is let to warm to room temperature, diluted with benzene and washed with water and brine. Evaporation of the solvent gives a mixture of the starting material and its C-7 epimer Similarly, a mixture of starting Schiff base and its epimer at C-7 is obtained from benzyl 7α-p-nitrobenzaldimino-1-methylamino-dethiacephalosporanate.

EXAMPLE 26 benzyl 7α-amino-1-benzylamino-dethiacephalosporanate and benzyl 7β-amino-1-benzylamino-dethiacephalosporanate To a solution of 198 mg. (1 mmole) of 2,4-dinitrophenylhydrazine in 10 ml. of ethanol is added 190 mg. (1 mmole) of p-toluenesulfonic acid monohydrate and the mixture is allowed to stir for 0.5 hour at room temperature. A solution of 523 mg. (1 mmole) of benzyl-7-p-nitrobenzaldimino-1-benzylamino-dethiacephalosporanate (C-7 α and β epimeric mixture) in 10 ml. of ethanol is then added. The reaction mixture is stirred for 0.5 hour at room temperature, filtered and the filtrated evaporated. The residue is taken up in 100 ml. of methylene chloride, washed with 2×50 ml. of brine, dried over anhydrous magnesium sulfate and evaporated to give benzyl-7-amino-1-benzylamino-dethiacephalosporanate (α & β epimers at C-7).

Similarly, C-7 epimeric mixture of benzyl-7-amino-1-methylamino-dethiacephalosporanate is obtained from benzyl-7-p-nitrobenzaldimino-1-methylamino-dethiacephalosporanate (mixture of α & β epimers at C-7).

EXAMPLE 27 benzyl 7β-thienylacetamido-1-benzylamino-dethiacephalosporanate, and benzyl 7α-thienylacetamido-1-benzylaminodethiacephalosporanate 143 μl. (2 mmoles) of pyridine is added to an ice-cold solution of 435 mg. (1 mmole) of a mixture of C-7 epimers of benzyl-7-amino-1-benzylamino-dethiacephalosporanate in 20 ml. of methylene chloride. 134 μl (1 mmole) of thienyl acetyl chloride is added dropwise and the mixture is allowed to stir 30 minutes at 0° C. The reaction mixture is washed with 20 ml. of water, 20 ml. of pH 2 buffer to remove excess base and then with 20 ml. of brine. The resulting solution is dried over anhydrous magnesium sulfate and the solvent is evaporated to give a residue, which is chromatographed on silica gel to give benzyl 7β-thienylacetamido-1-benzylamino-dethiacephalosporanate, and benzyl 7α-thienylacetamido-1-benzylamino-dethiacephalosporanate.

Similarly, acylation of a mixture of C-7 epimers of benzyl-7-amino-1-methylamino-dethiacephalosporanate and subsequent chromatography gives benzyl 7β-thienylacetamido-1-methylamino-dethiacephalosporanate and benzyl 7α-thienyl-acetamido-1-methylamino-dethiacephalosporanate.

Analogously, acylation of benzyl 7β-amino-1-benzylamino-dethiacephalosporanate with thienyl acetyl chloride gives benzyl 7β-thienylacetamido-1-benzylamino-dethiacephalosporanate.

Also, acylation of benzyl 7β-amino-1-methylamino-dethiacephalosporanate with thienyl acetyl chloride gives benzyl 7β-thienylacetamido-1-methylamino-dethiacephalosporanate.

EXAMPLE 28 sodium 7β-thienylacetamido-1-amino-dethiacephalosporanate 203 mg. of benzyl 7β-thienylacetamido-1-benzylamino-dethiacephalosporanate is hydrogenated in a mixture of dioxane and water, using 50 mg. of 10% palladium on carbon as catalyst in an atmosphere of hydrogen at 45 p.s.i. The catalyst is filtered and washed with a mixture of dioxane-water. The filtrate is concentrated and 1 equivalent of sodium bicarbonate is added. The resulting solution is freeze-dried to give sodium 7β-thienylacetamido-1-amino-decephalosporanate.

Similarly, benzyl 7α-thienylacetamido-1-benzylamino-dethiacephalosporanate is hydrogenated to give 7α-thienylacetamido-1-amino-dethiacephalosporin, which after neutralization and freeze-drying gives its sodium salt.

EXAMPLE 29 sodium 7β-thienylacetamido-1-methylamino-dethiacephalosporanate 483 mg. (1 mmole) of benzyl 7β-thienylacetamido-1-methylamino-dethiacephalosporanate is dissolved in 10 ml. of dioxane and 84 mg. (1 mmole) of sodium bicarbonate in 2 ml. of water and 50 mg. of 10% palladium on carbon are added. The mixture is reduced in hydrogen atmosphere at 45 p.s.i. for 1 hour. The catalyst is filtered and washed with 5 ml. dioxane and 5 ml. water. The filtrate is freeze-dried to give sodium 7β-thienylacetamido-1-methylamino-dethiacephalosporanate.

Similarly, benzyl 7α-thienylacetamido-1-methylamino-dethiacephalosporanate is hydrogenolyzed to give after neutralization sodium 7α-thienylacetamido-1-methylamino-dethiacephalosporanate.

EXAMPLE 30 sodium 7β-thienylacetamido-1-formamido-dethiacephalosporanate 379 mg. (1 mmole) of 7β-thienylacetamido-1-amino-dethiacephalosporin is dissolved in 15 ml. of methylene chloride and 72 μl. (1 mmole) of dry pyridine and 96 mg. (1 mmole) of N-formylimidazole are added. The reaction mixture is stirred 3 hours at room temperature, then washed with pH 2 buffer and then with brine. The organic phase is dried over anhydrous magnesium sulfate and the solvent removed to give 7β-thienylacetamido-1-formamido-dethiacephalosporanate, which on neutralization with sodium bicarbonate and freeze-drying gives sodium 7β-thienylacetamido-1-formamido-dethiacephalosporanate.

EXAMPLE 31 p-methoxybenzyl d,1-7β-(2-thienylacetamido)-1-oxa-dethiacephalosporanate

Oxalyl chloride (0.5 ml.) and dimethylformamide (0.02 ml.) are added to a stirring suspension of d,1-7β-(2-thienylacetamido)-1-oxa-dethiacephalosporanic acid (1.04 g.) in dry methylene chloride (75 ml.). The reaction mixture is stirred at room temperature for 20 minutes to give an orange solution. The solvent and excess oxalyl chloride are removed in vacuo. The residue is diluted with dry benzene and evaporated in vacuo to afford the crude acid chloride.

The acid chloride is dissolved in dry methylene chloride (40 ml.), and the solution is treated with p-methoxybenzyl alcohol (1.45 g.) and d,1-α-pinene (0.61 g.). The solution is stirred at room temperature for 40 minutes. Evaporation of the solvent in vacuo leaves a dark oil which is chromatographed on silica gel (75 g.). Elution with 20% ethylacetate in benzene affords p-methoxybenzyl d,1-7β-(2-thienylacetamido)-1-oxa-dethiacephalosporanate.

EXAMPLE 32 p-Methoxybenzyl d,1-7α-methoxy-7-(2-thienylacetamido)-1-oxa-dethiacephalosporanate Phenyllithium (2.6 ml of a 2.3 M solution) and anhydrous methanol (5 ml) are added with stirring to ice-cold, anhydrous tetrahydrofuran (50 ml) under nitrogen. The resulting solution is cooled to −78° C. (dry ice-acetone) and treated with a solution of p-methoxybenzyl d,1-7β-(2-thienylacetamido)-1-oxa-dethiacephalosporanate (1.00 g) in dry tetrahydrofuran (15 ml). After stirring for 2 minutes, the cold reaction mixture is treated with t-butyl hypochlorite (0.29 ml) and stirred for an additional 10 minutes. Glacial acetic acid (5 ml) is then added and the reaction mixture is concentrated in vacuo. The residue is dissolved in methylene chloride and the solution is washed with dilute aqueous sodium thiosulfate, aqueous sodium bicarbonate, and saturated brine. The methylene chloride solution is dried over magnesium sulfate, filtered, and evaporated in vacuo to yield p-methoxybenzyl d,1-7α-methoxy-7-(2-thienylacetamido)-1-oxa-dethiacephalosporanate.

EXAMPLE 33

Sodium d,1-7α-methoxy-7-(2-thienylacetamido)-1-oxa-dethiacephalosporanate

To an ice-cold mixture of p-methoxybenzyl d,1-7α-methoxy-7-(2-thienylacetamido)-1-oxa-dethiacephalosporanate (0.86 g) and anisole (4 ml) is added ice-cold trifluoroacetic acid (20 ml). The mixture is swirled to make homogeneous and then kept at 0° for 3 minutes. The trifluoroacetic acid is evaporated in vacuo at 0°, and the residue is warmed to 35° in vacuo. The remaining oil is diluted with water (50 ml) containing sodium bicarbonate (1.35 g) and extracted with methylene chloride (2×25 ml). The aqueous portion is acidified to pH 2.6 with 6N hydrochloric acid and extracted with ethyl acetate (3×25 ml). The combined ethyl acetate extracts are dried over magnesium sulfate, filtered, and evaporated in vacuo to provide d,1-7α-methoxy-7-(2-thienylacetamido)-1-oxa-dethiacephalosporanic acid.

A portion of the above free acid (0.41 g ) is stirred with sodium bicarbonate (0.09 g) in water (30 ml) for 20 minutes. The resulting mixture is washed with ethyl acetate (2×10 ml). The aqueous phase is separated, concentrated in vacuo to remove dissolved ethyl acetate, and lyophilized to afford sodium d,1-7α-methoxy-7-(2-thienylacetamido)-1-oxa-dethiacephalosporanate.

EXAMPLE 34

Potassium d,1-7α-methoxy-7-(2-thienylacetamido)-3-hydroxymethyl-1-oxa-dethiaceph-3-em-4-carboxylate A solution of sodium d,1-7α-methoxy-7-(2-thienylacetamido)-1-oxa-dethia cephalosporanate (0.41 g) in citrus acetyl esterase (13 ml) is placed in a thermostated 30° bath and stirred at that temperature. The pH of the reaction mixture is maintained at 6.7±0.1 by the periodic addition of 1N sodium hydroxide. After 16 hrs. at 30°, the rate of base addition is very slow and the reaction is stopped. The mixture is brought to room temperature, treated with powdered sodium chloride (4.5 g), and stirred. The resulting, thin suspension is overlaid with ethylacetate (20 ml) and, with vigorous stirring, acidified to pH 2.1 with 6N hydrochloric acid. The layers are separated and the aqueous portion is extracted with more ethylacetate (2×5 ml). The combined ethylacetate solution is backwashed with water (2×10 ml) and then layered with water (50 ml). The mixture is stirred vigorously while 6N potassium hydroxide is added to pH 5.4. The aqueous phase is separated, pumped under vacuum to removed dissolved ethyl acetate, and lyophilized to yield potassium d,1-7α-methoxy-7-(2-thienylacetamido)-3-hydroxymethyl-1-oxa-dethiaceph-3-em-4-carboxylate.

EXAMPLE 35

Sodium d,1-7α-methoxy-7-(2-thienylacetamido)-3-carbamoyloxymethyl-1-oxa-dethiaceph-3-em-4-carboxylate Potassium d,1-7α-methoxy-7-(2-thienylacetamido)-3-hydroxymethyl-1-oxy-dethiaceph-3-em-4-carboxylate (0.27 g) is dissolved in 0.05M pH 7 phosphate buffer (8 ml). The aqueous solution is layered with ethyl acetate (8 ml), cooled in an ice-bath, and, with vigorous stirring, acidified to pH 2.2 with 2.5N hydrochloric acid. The layers are separated and the aqueous portion is extracted with more ethyl acetate (2×8 ml). The combined ethyl acetate solution is washed with saturated aqueous sodium chloride, dried over sodium sulfate, and evaporated in vacuo to yield d,1-7α-methoxy-7-(2-thienylacetamido)-3-hydroxymethyl-1-oxa-dethiaceph-3-em-4-carboxylic acid.

The above free acid is dissolved in anhydrous tetrahydrofuran (15 ml) and the solution is cooled to −40° (dry ice-tetrachloroethane) under nitrogen. Chlorosulfonyl isocyanate (0.07 ml) is added to the solution via syringe. The resulting mixture is stirred at −40° for 4 hrs. and then treated with 0.1M pH 7 phosphate buffer (1.2 ml) at that temperature. The tetrahydrofuran is removed in vacuo and the wet residue is treated with 0.1M pH 7 phosphate buffer (8 ml) and ethyl acetate (8 ml). The resulting mixture is stirred at room temperature for 1 hour. The pH of the aqueous layer is brought to 8 with 2.5N sodium hydroxide and 5% aqueous trisodium phosphate. The organic layer is then separated and extracted with 0.1M pH 7 phosphate buffer (8 ml). The combined aqueous solution is acidified to pH 2.3 with 2.5N hydrochloric acid and extracted with ethyl acetate (2×20 ml). The ethyl acetate extracts are washed with saturated sodium chloride solution, dried over sodium sulfate, filtered, and evaporated in vacuo to afford d,1-7α-methoxy-7-(2-thienylacetamido)-3-carbamoyloxymethyl-1-oxa-dethiaceph-3-em-4-carboxylic acid.

A portion of the above free acid is dissolved in water containing 1.05 equivalents of sodium bicarbonate. The solution is washed with ethyl acetate, pumped under vacuum to remove dissolved ethyl acetate, and lyophilized to yield sodium d,1-7α-methoxy-7-(2-thienylacetamido)-3-carbamoyloxymethyl-1-oxa-dethiaceph-3-em-4-carboxylate.

EXAMPLE 36 p-Methoxybenzyl d,1-7α-methylthio-7-(2-thienylacetamido)-1-oxa-dethiacephalosporanate A solution of p-methoxybenzyl d,1-7β-(2-thienylacetamido)-1-oxa-dethiacephalosporanate (0.50 g) in anhydrous tetrahydrofuran (25 ml) is stirred and cooled to −78° (dry ice-acetone) under nitrogen. Phenyllithium (0.44 ml of a 2.3M solution) and, after 2 minutes, t-butyl hypochlorite (0.14 ml) are added to the cold solution. The reaction mixture is warmed to −17° and treated with a solution of methyl mercaptan (0.10 g) in dry tetrahydrofuran (2 ml). The reaction mixture is then concentrated in vacuo and the residue is dissolved in methylene chloride. The solution is washed with dilute aqueous sodium thiosulfate, water, and saturated brine, dried over magnesium sulfate, and evaporated in vacuo. Chromatographic purification of the residue on silica gel provides p-methoxybenzyl d,1-7α-methylthio-7-(2-thienylacetamido)-1-oxa-dethiacephalosporanate.

EXAMPLE 37

Sodium d,1-7α-methylthio-7-(2-thienylacetamido)-1-oxa-dethiacephalosporanate Ice-cold trifluoroacetic acid (7.5 ml.) is added to an ice-cold mixture of p-methoxybenzyl d,1-7α-methylthio-7-(2-thienylacetamido)-1-oxa-dethiacephalosporanate (0.33 g.) and anisole (1.5 ml.). After swirling to make homogeneous, the reaction mixture is kept at 0° for 5 minutes. The trifluoroacetic acid is removed in vacuo at 0°, and the residue is then warmed to 30° in vacuo. The resulting oil is partitioned between water (40 ml.) containing sodium bicarbonate (0.50 g.) and methylene chloride (20 ml.). The aqueous phase is separated, acidified to pH 2.5, and extracted with ethyl acetate. The extracts are dried over magnesium sulfate, filtered, and evaporated in vacuo to afford d,1-7α-methylthio-7-(2-thienylacetamido)-1-oxa-dethiacephalosporanate acid.

The free acid is stirred with a solution of sodium bicarbonate (0.05 g.) in water (20 ml.) for 15 minutes at room temperature. The resulting mixture is washed with ethyl acetate (2×10 ml.). The aqueous phase is separated and lyophilized to afford sodium d,1-7α-methylthio-7-(2-thienylacetamido)-1-oxa-dethiacephalosporanate.

EXAMPLE 38

7β-Amino-3-(2-methyl-1,3,4-thiadiazolyl-5-thiomethyl)-1-oxa-dethia-3-cephem-4-carboxylic acid To a mixture of 1 g. 7β-amino-1-oxa-dethiacephalosporanic acid, 10 ml. water and 5 ml. acetone is added NaHCO$_3$ until the pH of the solution is 7.9. A solution of 1½ equivalents 2-methyl-1,3,4-thiadiazole-5-thiol in 10 ml. acetone is added and the reaction kept in an 80° C. water bath 3 hours. The mixture is then cooled to 10° and the pH adjusted to 3.9 with 6N hydrochloric acid. 7β-amino-3-(2-methyl-1,3,4-thiadiazolyl-5-thiomethyl)-1-oxa-dethia-3-cephem-4-carboxylic acid crystallizes, and is filtered and dried.

7β-amino-3-(1-methyl-1,2,3,4-tetrazolyl-5-thiomethyl)-1-oxa-dethia-3-cephem-4-carboxylic acid is made in accordance with the above process, using 1-methyl-1,2,3,4-tetrazole-5-thiol in place of 2-methyl-1,3,4-thiadiazole-5-thiol.

EXAMPLE 39

7β-(D-2-phenyl-2-hydroxyacetamido)-3-(1-methyl-1,2,3,4-tetrazolyl-5-thiomethyl) 1-oxa-dethia-3-cephem-4-carboxylic acid To a solution of 10 mmoles 7β-amino-3-(1-methyl-1,2,3,4-tetrazolyl-5-thiomethyl)-1-oxa-dethia-3-cephem-4-carboxylic acid in 100 ml water and 100 ml acetone containing 5 g NaHCO$_3$ is added 20 mmoles D-phenyl-formyloxyacetyl chloride in 40 ml acetone at 0° C. After 1 hr stirring at 0° and 2 hrs at 25° the acetone is pumped off in vacuo and the aqueous solution added to 100 ml water and 200 ml EtOAc. The pH is adjusted to 2.0 with HCl and the ethyl acetate layer dried with MgSO$_4$, filtered and evaporated. The residue is stirred 3 hrs in 50 ml water containing 2.5 g NaHCO$_3$ and its pH adjusted to 0° C. to 2.0 with HCl. 7β-(D-2-phenyl-2-hydroxyacetamido)-3-(1-methyl-1,2,3,4-tetrazolyl-5-thiomethyl)-1-oxa-dethia-3-cephem-4-carboxylic acid is extracted into ethyl acetate and isolated by drying the solution with MgSO$_4$, filtering and evaporating the solvent.

EXAMPLE 40

7β-(2-tetrazoylacetamido)-3-(2-methyl-1,3,4-thiadiazolyl-5-thiomethyl)-1-oxa-dethia-3-cephem-4-carboxylic acid To a solution of 10 mmoles 7β-amino-3-(2-methyl-1,3,4-thiadiazolyl-5-thiomethyl)-1-oxa-dethia-3-cephem-4-carboxylic acid in 100 ml water and 100 ml acetone containing 5 g NaHCO$_3$ is added 20 mmoles 2-tetrazolacetyl chloride in 40 ml acetone at 20° C. After 1 hr stirring at 0° and 2 hrs at 20° the acetone is pumped off in vacuo and the aqueous solution added to 100 ml water and 200 ml EtOAc. The pH is adjusted to 2 with HCl and the ethyl acetate layer separated, dried with MgSO$_4$, filtered and evaporated, affording 7β-(2-3-(2-methyl-1,3,4-thiadiazolyl-5-thiomethyl)-1-oxa-dethia-3-cephem-4-carboxylic acid.

EXAMPLE 41

Benzyl 7-(2'-thienylacetamido)-7α-methoxy-1-methylene-1-dethiacephalosporanate

Step A: Benzyl 7-benzaldimino-7-bromo-1-methylene-1-dethiacephalosporanate

Benzyl 7β-benzaldimino-1-methylene-1-dethiacephalosporanate (527 mg.) is dissolved in 20 ml. of dry tetrahydrofuran. At −78° C., under nitrogen, 0.435 ml. of 2.3 M phenyl lithium is added. The reaction mixture is stirred at −78° C. for 5 minutes. 0.2 Grams of N-bromosuccinimide in 3 ml. of anhydrous tetrahydrofuran is then added. The cooling bath is removed and the reaction mixture allowed to come to 0° C. The solvent is removed under reduced pressure and the residue taken up in methylene chloride (30 ml.) and washed with pH 7 phosphate buffer and then with water, dried, and evaporated to a volume of about 12 ml. This solution of benzyl 7-benzaldimino-7-bromo-1-methylene-1-dethiacephalosporanate is used directly in the next step.

Step B: Benzyl 7-benzaldimino-7α-methoxy-1-methylene-1-dethiacephalosporanate Silver oxide (0.2 g.) is suspended in 20 ml. of methanol. The solution of the 7-bromo derivative obtained in Step A is added dropwise over 10 minutes to the silver oxide suspension. The reaction mixture is stirred for another 15 minutes. The silver salts are removed by filtration, the filtrate evaporated, and the residue taken up in benzen and washed twice with pH 7 phosphate buffer, then dried and evaporated to afford benzyl 7-benzaldimino-7α-methoxy-1-methylene-1-dethiacephalosporanate.

Step C: Benzyl 7-(2'-thienylacetamido)-7α-methoxy-1-methylene-1-dethiacephalosporanate 50 Mg. of benzyl 7-benzaldimino-7α-methoxy-1-methylene-1-dethiacephalosporanate is dissolved in 4 ml. of methylene chloride, cooled to 0° C., and 0.08 ml. of thienylacetyl chloride added. To this is added 0.4 ml. of a 1% solution of water in tetrahydrofuran and the mixture stirred at 0° C. for two minutes. 0.2 M. of pyridine is then added dropwise over 30 minutes. The reaction mixture is then washed with pH 2 phosphate buffer followed by pH 7 buffer then dried and evaporated to yield the desired product, after purification using preparative TLC on silica gel using 2% methanol/chloroform as eluant, to afford benzyl 7-(2'-thienylacetamido)-7α-methoxy-1-methylene-1-dethiacephalosporanate.

EXAMPLE 42

Benzyl 7β-phenylacetamido-7-methoxy-1-methylene-1-dethiacephalosporante

Benzyl 7-benzaldimino-7α-methoxy-1-methylene-1-dethiacephalosporanate (0.14 g.) is dissolved in 6 ml. tetrahydrofuran, 1 ml. of water is added and then 0.025 g. of PdCl₂. The mixture is stirred at room temperature for 3 hours. The solvent is removed under reduced pressure at ambient temperature. The residue is triturated with petroleum ether and the soluble material is discarded. The residue is taken up in 25 ml. methylene chloride, dried over MgSO₄ and evaporated to afford the residue containing the 7-amino metal complex which is taken up in 4 ml. of methylene chloride, cooled to 0° C. treated with 0.142 g. of pyridine and then with 0.042 ml. of phenylacetylchloride. The reaction mixture is stirred at 0° C. for 15 minutes. The reaction mixture is diluted with methylene chloride and washed once with pH 2 buffer and then with pH 7 buffer. The organic phase is dried and evaporated to afford the crude product which is purified by thin-layer chromatography.

EXAMPLE 43

1-(Benzyloxycarbonyldiethylphosphono)-methyl-3-azido-4-(2'-oxo)propyloxy-2-azetidinone 0.860 G. of 1-(benzyloxycarbonyldiethylphosphono)-methyl-3-azido-4-chloro-2-azetidinone is dissolved in 8 ml. of hydroxy acetone and 0.800 g. of silver fluroborate is added and the mixture stirred at room temperature for 15 minutes. The excess hydroxy acetone is removed under reduced pressure, the residue is taken up in CH₂Cl₂ and filtered. The filtrate is washed once with 5% NaHCO₃ and then with brine. The organic phase is dried and evaporated. Chromatography on silica gel (45 g) using 50% EtOAc in C₆H₆ as eluant gives 0.231 g 1-(benzyloxycarbonyldiethylphosphono)-methyl-3-azido-4-(2'-oxo)propyloxy-2-azetidinone as a mixture of cis and trans isomers.

i.r. 4.74 (azide); 5.62 (β-lactam); 4.75 (ester and ketone carbonyl).

n.m.r. τ 2.66 (C₆H₅—); 4.75 (C₆H₅—CH—); 5.0–6.1 multiplets (β-lactam, C—CH₂—O and O—CH₂—CH₃ protons)
‖
O 7.85 (CH₃—C—); 8.73 (CH₃—CH₂—).
‖
O

EXAMPLE 44

Cis and Trans 4-Benzyloxycarbonyl-3-methyl-7-azido-1-oxa-dethia-3-cephem 0.468 G. of cis and trans 1-benzyloxycarbonyl-dethiacephalosporanate)methyl-3-azido-4-(2'oxo)-propyloxy-2-azetidinone is dissolved in 20 ml. anhydrous DME under N₂ and treated with 0.047 g. sodium hydride (57% in mineral oil). The reaction mixture is stirred for 2 hours and then taken up in C₆H₆, washed once with pH 7 buffer and then with brine. The organic phase is dried and evaporated to give a residue which on chromatography on silica gel using 10% ethylacetate in C₆H₆ as eluant gives cis and trans 4-benzyloxycarbonyl-3-methyl-7-azido-1oxa-dethia-3cephem.

i.r. 4.72 (azide); 5.60 (β-lactam) 5.80 (ester carbonyl) 6.09 (C=C).

EXAMPLE 45

Cis and trans 4-benzyloxycarbonyl-3-methyl-7-amino-1-oxadethia-3-cephem 0.300 G. of cis and trans 4-benzyloxycarbonyl-3-methyl-7-azido-1-oxa-dethia-3-cephem is dissolved in 20 ml C₆H₆, 0.160 g. of PtO₂ is added and the mixture is reduced under 40 lbs. H₂ pressure for ½ hour. The catalyst is filtered off and the filtrate is evaporated to give cis and trans 4-benzyloxycarbonyl-3-methyl-7-amino-1-oxadethia-3-cephem.

EXAMPLE 46

4-Benzyl-oxycarbonyl-3-methyl-7 α-(D-α-azido)-phenylacetamido-1-oxadethia-3-cephem and 4-benzyloxycarbonyl-3-methyl-7 β-(D-α-azido)-phenylacetamido-1-oxadethia-3-1-cephem 0.274 G. cis and trans 4-benzyloxycarbonyl-3-methyl-7-amino-1-oxa-dethia-3-cephem is dissolved in 25 ml CH₂Cl₂ and cooled to 0°. 0.195 G. of D-α-azido-phenylacetyl chloride and 0.196 g. of pyridine are added and the mixture is stirred for 15 minutes. The reaction mixture is washed once with pH 7 phosphate buffer, then pH 3 phosphate buffer and then once again with pH 7 phosphate buffer. The organic phase is dried and evaporated. The residue is chromatographed on silica gel to give 4-benzyl-oxycarbonyl-3-methyl-7 α-(D-α-azido)-phenylacetamido-1-oxadethia-3-cephem and 4-benzyloxycarbonyl-3-methyl-7 β(D-α-azido)-phenylacetamido-1-oxa-dethia-3-cephem.

EXAMPLE 47

3-Methyl-7-β-(D-α-amino)-phenylacetamido-1oxa-dethia-3-cephem-4-carboxylic acid.

0.150 G. of 4-benzyloxycarbonyl-3-methyl-7β-(D-α-azido)-phenylacetamido-1-oxa-dethia-3-cephem is dissolved in 5 ml. dioxane and 5 ml. H₂O is added followed by 0.075 g. of 10% Pd/C (Bolhofer catalyst). The mixture is reduced under 40 lbs H₂ pressure for ½ hour. The catalyst is filtered off and the filtrate is freeze-dried to give 3-methyl-7-β-(D-α-amino)-phenylacetamido-1-oxa-dethia-3-cephem-4-carboxylic acid.

EXAMPLE 48

4-Pentenoyl chloride

Into a solution of 10 g. (0.1 mole) of commercial 4-pentenoic acid in 40 ml. of ether is dropped slowly a solution of 10 ml. of oxalyl chloride in 10 ml. of dry ether. Effervescence stops after 0.5 hour. After 3 hours further stirring, the reaction mixture is distilled slowly to give 92% of 4-pentenoyl chloride, boiling at 126°–9° C.

n.m.r (CDCl₃) Δ: 2.51

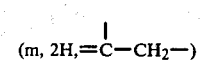

3.00 (t, 2H, O=C—CH₂—)
4.90–6.20 (m, 3H, CH₂=CH—)
i.r. (film) λ: 5.55 (>C=O)
6.06 (>C=C<)

EXAMPLE 49

1-Diazo-5-hexen-2-one

A solution of diazomethane in 1000 ml of ether is prepared from 0.75 mole of N-nitrosomethylurea. To this solution, cooled to 5° C., is added dropwise a solution of 0.1 mole of 4-pentenoyl chloride in 100 ml. of dry ether. The resulting solution, protected from light with aluminum foil, is kept overnight at room temperature. Concentration of the crude solution gives yellow 1-diazo-5-hexen-2-one in almost quantitative yield.

i.r. (film): λ 4.72 (—N₂)
6.06 (>C=C< and >C=O)

EXAMPLE 50

1-Acetoxy-5-hexen-2-one

Into 35 ml of glacial acetic acid at 60°–70° C. is dropped slowly 12.4 g. (0.1 mole) of 1-diazo-5-hexen-2-one. After the nitrogen evolution stops, the reaction mixture is heated to reflux for one hour. The resulting mixture is extracted with 3×50 ml of methylene chloride. The organic layer is dried over anhydrous magnesium sulfate. Concentration of the filtrate gives 1-acetoxy-5-hexen-2-one as a brown oil in 90% yield, based on the starting 4-pentenoyl chloride.

n.m.r. (CDCl₃)σ : 2.17 (OCCH₃, S, 3H)
   O
   ‖
4.67 (—CCH₂—OAc, S, 2H)
2.47 (—CH₂—CH₂—, m, 4H)
4.82–6.17 (CH₂=CH—, m, 3H)
   O
   ‖
i.r. (film), τ : 5.70 (—OCCH₃)

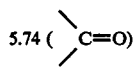
5.74 ( C=O)

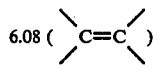
6.08 ( C=C )

EXAMPLE 51

2-Acetoxymethyl-2-(3-buten-1-yl)-1,3-dioxolane

A mixture of 15.6 g. (0.1 mole) of 1-acetoxy-5-hexen-2-one, 18.6 g. (0.3 mole) of ethylene glycol in 250 ml. of benzene containing 1.56 g. of p-toluene sulfonic acid monohydrate is heated to reflux using a Dean-Stark water separator. After 2 hours, the reaction mixture is shaken well with 250 ml. of cold water. The aqueous layer is washed with 3×25 ml. of ether. The combined organic layers are dried over anhydrous magnesium sulfate. Evaporation of the solvent gives 2-acetoxymethyl-2-(3-buten-1-yl)-1,3-dioxolane in 90% yield as a light brown oil.

O
   ‖
n.m.r. (CDCl₃) δ : 2.03 (s, OCCH₃)
1.7–2.15 (m, —CH₂—CH₂—)
3.95 (s, —OCH₂CH₂O—)
4.00 (s, —CH₂OAc)
4.80–6.1 (m, CH₂=CH—)
   O
   ‖
i.r. (film) λ :  5.70 (—OCCH₃)
6.06 (CH₂=CH—)

EXAMPLE 52

2-Acetoxymethyl-2-(3-propanal-1-yl)-1,3-dioxolane

To a well-stirred mixture of 5.0 g. (25 mmoles) of 2-acetoxymethyl-2-(3-buten-1-yl)-1,3-dioxolane and 300 mg. of osmium tetroxide in 75 ml. of ether and 75 ml. of water is added portionwise 11.6 g. (54 mmoles) of sodium metaperiodate so that the reaction temperature remains 24°–27° C. After the addition of the periodate, a voluminous white solid starts precipitating out. After 2.5 hours, the reaction mixture is extracted with 3×50 ml. of methylene chloride. Drying over anhydrous magnesium sulfate and solvent removal affords crude 2-acetoxymethyl-2-(3-propanal-1-yl)-1,3-dioxolane which soon darkens. Chromatography of the crude product on silica gel (30 g. per gm. of the crude material) using 50:50 ethyl acetate-benzene mixture as eluent gives 2-acetoxymethyl-2-(3-propanal-1-yl)-1,3-dioxolane in 60% yield. Pure aldehyde is stable only at the freezer-temperatures.

n.m.r. (CDCl₃) δ:
   O
   ‖
2.10 (s, OCCH₃)
2.04–2.60 (m, —CH₂CH₂—)
4.0 (—OCH₂CH₂O—, s)
4.03 (s, CH₂OAc)
9.73 (t, O=C—H)
i.r. (film) λ:
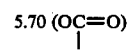
3.66 ( >C—H)

5.70 (OC=O)

5.79 (H—C=O)

EXAMPLE 53 cis and trans-benzyl-α-[5-acetoxy-4,4-ethylenedioxypentanaldimino]-diethylphosphonoacetate To a solution of 75 mg. (0.25 mmole) of benzyl-α-amino-diethylphosphonoacetate in 5 ml. of ether under nitrogen is added 2 g. of anhydrous magnesium sulfate and then a solution of 50 mg. (0.25 mmole) of 5-acetoxy-4,4-ethylenedioxy-pentanal in 5 ml. of ether. The mixture is stirred for 50 minutes. Filtration and concentration of the filtrate gives a mixture of cis and trans benzyl-α-[5-acetoxy-4,4-ethylenedioxy-pentanaldimino]-diethylphosphonoacetate in almost quantitative yield. This Schiff base is very unstable and hence is used soon after its preparation.

n.m.r. (CDCl₃):σ
1.27 (t, OCH₂CH₃)

2.08 (s, OCCH₃);
      ‖
      O 3.96 & 4.02 (singlets; —OCH₂CH₂O— & —CH₂OAc)

4.5 (d, J = 20 cps; HC—P—)

5.25 (s, OCH₂φ)
7.38 (—φ,S)

7.82 (d,d, one of the isomeric —C=N—)
                                  |
                                  H i.r. (film) λ:
      O
      ‖
5.72 (OCCH₃ & O=COCH₂φ)

6.00 ( >C=N—)

EXAMPLE 54

Cis-1-(benzyloxycarbonyldiethylphosphono)methyl-3-azido-4-(3-ethylenedioxy-4-acetoxy)butyl-2-azetidinone A solution of 0.075 ml. of anhydrous triethylamine in 2 ml. of anhydrous ether is added dropwise under nitrogen to a solution of 0.04 ml. of azidoacetyl chloride in 2 ml. of anhydrous ether at −60° C. (acetone-water-dry ice bath). After stirring for an hour, to this white solid suspension in ether at −60° C. under nitrogen is added slowly a solution of 115 mg. of freshly prepared benzyl-α-[5-acetoxy-4,4-ethylenedioxy-pentanaldimino]-diethylphosphonoacetate in 2 ml. of anhydrous ether. The resulting mixture is stirred as it warms up to room temperature over a period of 3-4 hours. After continued stirring of the reaction mixture overnight at room temperature, it is diluted with 20 ml. of methylene chloride and washed with ~15 ml. of brine. The organic layer, dried over anhydrous magnesium sulfate is concentrated to give 130 mg. of a dark residue. This is purified on silica gel preparative TLC to give 40 mg. of cis-1-(benzyloxycarbonyldiethylphosphono)methyl-3-azido-4-(3-ethylenedioxy-4-acetoxy)butyl-2-azetidinone.

n.m.r. (CDCl₃) (100 mc) σ:
        O
        ‖
2.08 (s, OCCH₃); 4.7 (d, J =
                    H
                    |
5.5 cps) —N₃—C—
              ‖
              O⟋—N—

5.00 (d; HC—P—; J = 24 cps)

5.22 (s, CH₂φ); 7.34 (s, aromatic)

i.r. (film) λ:
4.70 (—N₃); 5.52 (β-lactam —N—C=O)
            CH₃
5.69 (—OC⟨   and COOCH₂φ)
            O

EXAMPLE 55

Cis-1-(benzyloxycarbonyl-diethylphosphono)methyl-3-azido-4-(3-oxo-4-hydroxy)butyl-2-azetidinone A suspension of 100 mg. of cis-1-(benzyloxycarbonyl-diethylphosphono)methyl-3-azido-4-(3-ethylenedioxy-4-acetoxy)butyl-2-azetidinone in 8 ml. of aqueous 10% sulfuric acid and 1 ml. glacial acetic acid is heated 2 hours with stirring at 50° C. The reaction mixture is then cooled to room temperature and extracted with 3×15 ml. of methylene chloride. The combined organic layers are washed with 2×5 ml of brine, and dried over anhydrous magnesium sulfate. The solvent is removed to give 89% of cis-1-(benzyloxycarbonyl-diethylphosphono)methyl-3-azido-4-(3-oxo-4-hydroxy)butyl-2-azetidinone as a light brown gum.

i.r. (film) λ: 2.56 (OH)
4.70 (—N₃)
5.62 (β-lactam >C=O)
5.72–5.80 (>C=O and —COOCH₂φ).

EXAMPLE 56

Cis-1-(benzyloxycarbonyl-diethylphosphono)-methyl-3-azido-4-(3-oxo-4-acetoxy)butyl-2-azetidinone To a solution of 26 mg. of cis-1-(benzyloxycarbonyl-diethylphosphono)-methyl-3-azido-4-(3-oxo-4-hydroxy)butyl-2-azetidinone in 1 ml. of anhydrous methylene chloride under nitrogen are added 8 μl of acetyl chloride and subsequently 8.5 μl. of anhydrous pyridine. The clear solution is let stand overnight at room temperature, diluted with 10 ml. of methylene chloride and washed with 3×5 ml. of brine. The resulting organic layer, dried over anhydrous magnesium sulfate, is concentrated to give 82.5% of cis-1-(benzyloxycarbonyl-diethylphosphono)-methyl-3-azido-4-(3-oxo-4-acetoxy)butyl-2-azetidinone as light brown gum.

n.m.r. (CDCl₃) δ: (100 Mc)
         O
         ‖
2.14 (s, —OCCH₃)
1.25 (m, OCH₂CH₃)
4.13 (m, OCH₂CH₃)
4.63 (s, —CH₂OAc)

H
                  |
4.73 (d, J = 5.5 cps, N₃—C—C=O)

4.99 (d, J = 24 cps, H—C—P⟨)

i.r. (film) λ:
7.32 and 7.34 (aromatic protons)
4.70 (—N₃)

5.62 (β-lactam >C=O)

5.70 (—OCCH₃ & COOCH₂φ)
        ‖
        O

EXAMPLE 57

Benzyl-7β-azido-1-methylene-dethiacephalosporanate 3.7 Mg. of sodium hydride (57% in paraffin oil) is added to a solution of 40 mg. of cis-1-(benzyloxycarbonyldiethylphosphono)-methyl-3-azido-4-(3-oxo-4-acetoxy)-butyl2-azetidinone in 0.5 ml. of freshly distilled anhydrous dimethoxyethane under nitrogen. After 15 minutes stirring at room temperature, the reaction mixture is heated 1.5 hrs. at 50° C. The residue after the solvent removal is shaken well with 2 ml. of brine and extracted with 3×5 ml. of methylene chloride. The combined organic layers are dried over anhydrous magnesium sulfate. Removal of the solvent from the filtrate gives 30 mg. of crude material, which is purified on silica gel preparative TLC with 1:1 ethyl acetate-benzene to give benzyl-7β-azido-1-methylenedethiacephalosporanate in ~62% yield.

| nmr (CDCl₃) δ: (100 Mc) | 1.98 (s, OCCH₃) with C=O |
|---|---|
|  | 3.72 (m, C—C—N— with H) |
|  | 4.91 (AB quartet, CH₂OAc) |
|  | 4.85 (d, J - 5.5 cps; N₃—C—H) |
|  | 5.20 (s, CH₂φ) |
|  | 7.21 (m, aromatic protons) |
| ir (film) λ: | 4.70 (—N₃) |
|  | 5.62 (β-lactam >C=O) |
|  | 5.73 (COOCH₂φ and OCCH₃ with C=O) |
|  | 6.09 ( >C=C< ) |

EXAMPLE 58

7β-Amino-1-methylenedethiacephalosporanic acid

A mixture of 74 mg. of benzyl-7β-azido-1-methylenedethiacephalosporanate and 10 mg. of 10% Palladium on carbon (Bolhoffer catalyst) in 4 ml. of dioxane and 2 ml. of water is hydrogenated 0.5 hr. in an atmosphere of hydrogen at 45 psi and at room temperature. The catalyst is filtered and washed with 4×2 ml. of water. The solvent is removed from the filtrate to give 55 mg. of an amorphous solid, 7β-amino-1-methylenedethiacephalosporanic acid.

| ir (Nujol) λ: | 2.94 (—NH₂ & OH of COOH) |
|---|---|
|  | 5.57 (β-lactam >C=O) |
|  | 5.74 (COOH & OCCH₃ with C=O) |

EXAMPLE 59

7β-(2-Thienyl)acetamido-1-methylene-dethiacephalosporanic acid

A suspension of 50.8 mg. of 7β-amino-1-methylenedethiacephalosporanic acid in 6 ml. of aqueous 67% acetone is cooled in an ice bath. 33.6 Mg. of sodium bicarbonate and then 26.8 μl. of thienylacetyl chloride are added. After stirring an hour at 0° C., acetone is removed and the residual aqueous layer is diluted with 10 ml of brine. The resulting solution is washed with 3×10 ml. of methylene chloride, then acidified with 2.5N hydrochloric acid solution. The acidified aqueous phase is extracted with 3×10 ml. of ethyl acetate. The combined organic layers are dried over anhydrous magnesium sulfate. The solvent is removed from the filtrate to afford 52 mg. of crude material, which is triturated with 2×2 ml. of anhydrous ether to give 27 mg. of 7β-(2-thienyl)acetamido-1-methylene-dethiacephalosporanic acid as a white amorphous powder.

| nmr (D₆-acetone) σ: | 2.03 (s, OCCH₃ with C=O) |
|---|---|
|  | 3.89 (s, NCCH₂— with C=O) |
|  | 5.50 (—N—C with H ; q, J₁ = 5.5 cps; J₂ = 9 cps) |
|  | 4.97 (AB quartet, —CH₂OAc) |
|  | 8.00 (d, NH; J = 9 cps) |
| ir (Nujol) λ: | 5.70 (β-lactam >C=O) |
|  | 5.80 (COOH & OC=O with CH₃) |

EXAMPLE 60

Sodium 7β-(2-thienyl)acetamido-1-methylene-dethiacephalosporanate

19 Mg. of 7β-(2-thienyl)acetamido-1-methylene-dethiacephalosporanate is suspended in 2 ml. of distilled water. 4.10 Mg. of sodium bicarbonate is added. The resulting solution is freeze-dried to give the sodium salt as a white foam.

| nmr (D₂O) δ: | 2.07 (s, —OCCH₃ with C=O) |
|---|---|
|  | 3.90 (s, =CCH₂CNH with C=O) |
|  | 5.28 (d, J = 5 cps, —N—C—C=O with H) |
|  | 4.80 (AB quartet, CH₂OAc) |
| ir (Nujol) λ: | 5.67 (β-lactam >C=O) |
|  | 5.73 (OC=O with CH₃) |
|  | 5.98 (HN—C=O) |
|  | 6.22 (COO⁻) |
| uv λH₂O: & | 238 (ε = 320 255 (ε = 261 |

EXAMPLE 61

Benzyl-7β-amino-1-methylene-dethiacephalosporanate

To an ice-cooled solution of 18 mg. of benzyl-7β-azido-1-methylene-dethiacephalosporanate in 0.5 ml. of anhydrous chloroform is added 14 μl. of anhydrous triethylamine under nitrogen. Hydrogen sulfide is slowly passed into this stirred solution. Colloidal yellow precipitate is formed instantaneously. After 5 minutes introduction of hydrogen sulfide, the solvent is removed to give benzyl-7β-amino-1-methylene-dethiacephalosporanate.

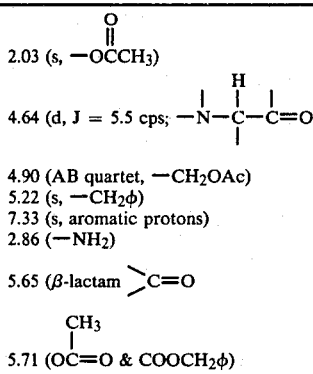

nmr (CDCl₃):
2.03 (s, —OCCH₃)
4.64 (d, J = 5.5 cps; —N—C—C=O with H)
4.90 (AB quartet, —CH₂OAc)
5.22 (s, —CH₂φ)
7.33 (s, aromatic protons)

ir (film) λ:
2.86 (—NH₂)
5.65 (β-lactam >C=O)
5.71 (OC=O & COOCH₂φ) CH₃

EXAMPLE 62

Benzyl-7β-(2thienyl)acetamido-1-methylene-dethiacephalosporanate 17.5 Mg. of benzyl-7β-amino-1-methylene-dethiacephalosporanate is dissolved in 2 ml. of anhydrous methylene chloride under nitrogen. 7 μl. Of anhydrous triethylamine and 5.8 μl. of thienylacetyl chloride are added. After letting the reaction mixture stand 6 hrs. at room temperature, it is diluted with 5 ml. of methylene chloride and washed with 2×4 ml. of brine. The organic layer is dried over anhydrous magnesium sulfate. The solvent is removed from the filtrate to give crude benzyl-7β-(2-thienyl)acetamido-1-methylene-dethiacephalosporanate, which is purified by silica gel preparative TLC.

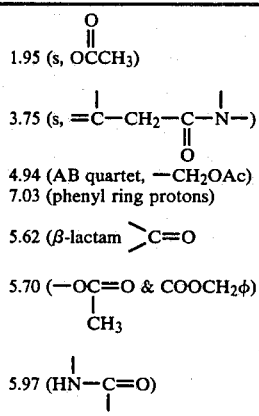

nmr (CDCl₃) δ:
1.95 (s, OCCH₃)
3.75 (s, =C—CH₂—C—N—)
       O
4.94 (AB quartet, —CH₂OAc)
7.03 (phenyl ring protons)

ir (film) λ:
5.62 (β-lactam >C=O)
5.70 (—OC=O & COOCH₂φ) CH₃
5.97 (HN—C=O)

EXAMPLE 63

7-β-(D-α-azido)-phenylacetamido-1-methylene-dethiacephalosporanic acid 1.016 g. of 7-β-amino-1-methylene-dethiacephalosporanic acid is dissolved in 5 ml. of acetone and 10 ml. of H₂O containing 0.672 g. of sodium bicarbonate. The mixture is cooled to 0° C. and treated with 0.784 g. of D-α-azido-phenyl-acetyl chloride in 5 ml. acetone. The mixture is stirred at 0° C. for 15 minutes and the acetone is removed under reduced pressure. The residual aqueous solution at pH 8 is extracted once with ethyl acetate and then acidified to pH 2 with pH 2 phosphate buffer and extracted with ethyl acetate. The ethyl acetate extract is dried and evaporated to give 7-β-(D-α-azido)-phenylacetamido-1-methylene-dethiacephalosporanic acid.

EXAMPLE 64 sodium 7-β-(D-α-azido)-phenylacetamido-3-hydroxymethyl-1-methylene-dethia-3-cephem-4-carboxylate 7-β-(D-α-azido)-phenylacetamido-1-methylene-dethiacephalosporanic acid (1 g.) is dissolved in 100 ml. of a solution of citrus acetyl esterase (J. D. A. Jeffery, et. al., Biochem. J. (1961) 81, 591). The pH is adjusted to 6.6 and the mixture is maintained at 30° C. 1 N NaOH is added dropwise to maintain the pH at 6.6 as the reaction proceeds and the reaction is continued until no further pH change occurs. 10 g. NaCl is added and the mixture is layered with 50 ml. EtOAc, the pH is adjusted to 2.1 with HCl and the mixture is stirred vigorously. The EtOAc layer is separated and washed once with water and then layered with water and stirred and the pH of the aqueous phase is adjusted to 5.9 with 6 N NaOH. The aqueous layer is separated and freeze-dried to give sodium 7-β-(D-α-azido)-phenylacetamido-3-hydroxymethyl-1-methylene-dethia-3-cephem-4-carboxylate.

EXAMPLE 65

7-β-(D-α-azido)-phenylacetamido-3-carbamoyloxymethyl-1-methylene-dethia-3-cephem-4-carboxylic acid 0.464 g. of the sodium 7-β-(D-α-azido)-phenylacetamido-3-hydroxymethyl-1-methylene-dethia-3-cephem-4-carboxylate is dissolved in 10 ml. of 0.05 M NaH₂PO₄ and the pH is adjusted to 2.2 with 2.5 N HCl. The mixture is extracted with ethyl acetate 3 times and the combined ethyl acetate extract is dried and evaporated to 2 ml. This is diluted with 20 ml. THF and cooled to −78° C. and treated with 0.141 g. of chlorosulfonylisocyanate. The reaction mixture is stirred for 1½ hours at −78° C. then treated with 0.1 M pH 2 phosphate buffer (2 ml.) and the THF is removed under reduced pressure. Ethyl-acetate (10 ml.) and 0.1 M pH 2 phosphate buffer (10 ml.) are added and the mixture is stirred for 1 hour at room temperature. The pH of the aqueous layer is adjusted to 8, the mixture shaken and the organic phase is separated. The aqueous phase is adjusted to pH 2 and extracted with ethyl acetate. 3×30 ml. The ethyl acetate extract is dried and evaporated to give 7-β-(D-α-azido)-phenylacetamido-3-carbamoyloxymethyl-1-methylene-dethia-3-cephem-4-carboxylic acid.

EXAMPLE 66

7-β-(D-α-amino)-phenylacetamido-3-carbamoyloxymethyl-1-methylene-dethia-3-cephem-4-carboxylic acid 0.300 g. of 7-β-(D-α-azido)-phenylacetamido-3-carbamoyloxymethyl-1-methylene-dethia-3-cephem-4-carboxylic acid is dissolved in 5 ml. H₂O and 5 ml. dioxane, 0.150 g. of 10% Pd/C (Bolhofer catalyst) is added and the mixture is reduced under 40 lbs H₂ pressure for ½ hour. The catalyst is filtered off and the filtrate is freeze-dried to give 7-β-(D-α-amino)-phenylacetamido-3-carbamoyloxymethyl-1-methylene-dethia-3-cephem-4-carboxylic acid.

EXAMPLE 67 benzyl 7-amino-1-benzyloxycarbonylamino-dethiacephalosporanate

A solution of 505 mg. (1 mmole) benzyl 7-azido-1-benzyloxycarbonylamino-dethiacephalosporanate in 20 ml. of benzene is stirred in an atmosphere of hydrogen in the presence of 50 mg. of platinum oxide at atmospheric pressure and room temperature until the azide band disappears. The catalyst is filtered and washed with 3×4 ml. of benzene. The filtrate is concentrated to give benzyl 7-amino-1-benzyloxycarbonylamino-dethiacephalosporanate.

EXAMPLE 68 benzyl 7-(p-nitrobenzaldimino)-1-benzyloxycarbonylamino-dethiacephalosporanate

To a solution of 152 mg. (1 mmole) of p-nitrobenzaldehyde in 5 ml. of chloroform is added a solution of 479 mg. (1 mmole) of benzyl 7-amino-1-benzyloxycarbonylamino-dethiacephalosporanate in 5 ml. of chloroform. 2 g. of anhydrous magnesium sulfate is added and the mixture is stirred for 2 hours. The solid is filtered and washed with 3×5 ml. of chloroform. The solvent removal from the filtrate give benzyl 7-(p-nitrobenzaldimino-1-benzyloxycarbonylamino-dethiacephalosporanate.

EXAMPLE 69 benzyl 7α-methyl-7-p-nitrobenzaldimino-1-benzyloxycarbonylamino-dethiacephalosporanate To a solution of 306 mg. (0.5 mmole) of benzyl 7-p-nitrobenzaldimino-1-benzyloxycarbonylaminodethiacephalosporanate in 10 ml. of anhydrous tetrahydrofuran at −78° C. is added under nitrogen 0.22 ml. of 2.3 M phenyllithium (0.5 mmole) slowly. 0.4 ml. of methyliodide in 10 ml. of N,N-dimethylformamide is added dropwise. The reaction mixture is allowed to warm to room temperature, poured into ice water and extracted with 3×20 ml. of ethyl acetate. The mixed organic layers are washed with 2×10 ml. brine and dried over anhydrous magnesium sulfate. The solvent removal from the filtrate gives benzyl 7α-methyl-7-p-nitrobenzaldimino-1-benzyloxycarbonylamino-dethiacephalosporanate.

EXAMPLE 70 benzyl 7α-methyl-7-amino-1-benzyloxycarbonylaminodethiacephalosporanate

To a solution of 99 mg. (0.5 mmole) of 2,4-dinitrophenylhydrazine in 5 ml. of ethanol is added 95 mg. (0.5 mmole) of p-toluene sulfonic acid monohydrate and the mixture is allowed to stir half an hour at room temperature. A solution of 313 mg. (0.5 mmole) of benzyl-7α-methyl-7β-p-nitrobenzaldimino-1-benzyloxycarbonylamino-dethiacephalosporanate in 5 ml. of ethanol is then added. The reaction mixture is stirred for 0.5 hour at room temperature, filtered and the filtrate evaporated. The residue is taken up in 50 ml. methylene chloride, washed with 2×20 ml. brine, dried over anhydrous magnesium sulfate and evaporated to give benzyl 7α-methyl-7-amino-1-benzyloxycarbonylaminodethiacephalosporanate.

EXAMPLE 71 benzyl 7α-methyl-7-(2-thienyl)acetamido-1-benzyloxycarbonylamino-dethiacephalosporanate 72 µl. of pyridine is added to an ice-cold solution of 247 mg. of benzyl 7α-methyl-7β-amino-1-benzyloxycarbonylamino-dethiacephalosporanate in 10 ml. of methylene chloride. 67 µl. of 2-thienylacetyl chloride is added and the mixture is washed with 10 ml. of water, 10 ml. of pH 2 buffer and then with 10 ml. of pH 7 buffer. The resulting solution is dried over anhydrous magnesium sulfate and the solvent is evaporated to give a residue, which is chromatographed on silica gel to give benzyl 7α-methyl-7-(2-thienyl)acetamido-1-benzyloxycarbonylamino-dethiacephalosporanate.

EXAMPLE 72 sodium 7α-methyl-7β-(2-thienyl)-acetamido-1-amino-dethiacephalosporanate 256 mg. of benzyl 7α-methyl-7β-(2-thienyl)-acetamido-1-benzyloxycarbonylamino-dethiacephalosporanate is hydrogenated in a mixture of dioxane and water, using 59 mg. of 10% palladium on carbon as catalyst in an atmosphere of hydrogen at 45 p.s.i. The catalyst is filtered and washed with a mixture of dioxane-water. The filtrate is concentrated and one equivalent of sodium bicarbonate is added. The resulting solution is freezedried to give sodium 7α-methyl-7β-(2-thienyl)-acetamido-1-amino-dethiacephalosporanate.

EXAMPLE 73

7β-(2-thienyl)-acetamido-3-(1-pyridyl)-methyl-1-formamidodethia-3-cephem-4-carboxylic acid betaine A solution of 407 mg. (1 mmole) of 7β-(2-thienyl)-acetamido-1-formamido-dethiacephalosporanic acid, 217 mg. (2.25 mmoles) of potassium thiocyanate, and 0.216 mg. (2.70 mmole) of pyridine in 1.1 ml. of water is adjusted to pH 6.5 with 85% phosphoric acid and heated 5.5 hours with stirring at 58°–61° C. The solution is cooled to room temperature and extracted with 25% Amberlite-LA-1 (acetate form) in methyl isobutyl ketone and washed with methyl isobutyl ketone. The aqueous solution is allowed to stand 15 hours below 5° C. to give 7β-(2-thienyl)-acetamido-3-(1-pyridyl)-methyl-1-formamido-dethia-3-cephem-4-carboxylic acid betaine.

EXAMPLE 74

7-methoxy-7-(α-carboxy-3-thienyl)acetamido-3-carbamoyloxy methyl-1-methylene-dethia-ceph-3-em-4-carboxylic acid disodium salt A. benzhydryl 7β-amino-1-methylene-dethiacephalosporanate 1.54 g. of 7-β-amino-1-methylene-dethiacephalosporanic acid is stirred 5 minutes at 25° C. in 70 ml. of dioxane with 1.7 g. of p-toluenesulfonic acid hydrate. Methanol (20 ml.) is added and the solvents are removed in vacuo. The residue is dissolved in 80 ml. of dioxane and 2.9 g. of diphenyldiazomethane are added. After evolution of nitrogen is complete the dioxane is removed under reduced pressure and the residue is stirred with methylene chloride (100 ml.) and water (100 ml.) containing sufficient dipotassium hydrogen phosphate to bring the pH to 8. The layers are separated and the aqueous portion is extracted with methylene chloride. The combined organic layers are dried over magnesium sulfate, filtered and evaporated leaving benzhydryl 7β-amino-1-methylene-dethiacephalosporanate.

B. benzhydryl 7β-(p-nitrobenzylideneamino)-1-methylene-dethiacephalosporanate A mixture of p-nitrobenzaldehyde (0.58 g.), anhydrous magnesium sulfate (9 g.) and benzhydryl 7-β-amino-1-methylene-dethiacephalosporanate (1.14 g.) in 70 ml. of methylene chloride is stirred at room temperature for 15 hours. The mixture is filtered and the filtrate is evaporated under reduced pressure to give benzhydryl 7β-(p-nitrobenzylideneamino)-1-methylene-dethiacephalosporanate.

C. benzhydryl 7-α-methylthio-7-(p-nitrobenzylideneamino)-1-methylenethiacephalosporanate A solution of benzhydryl 7β-(p-nitrobenzylideneamino)-1-methylenedethiacephalosporanate (1.98 g.) in anhydrous tetrahydrofuran (70 ml.) is stirred at −78° C. under a nitrogen atmosphere. Phenyllithium (1.9 ml. of a 2.3 M solution in 7:3 benzene-ether) is added followed by anhydrous dimethylformamide (88 ml.) dropwise over a six-minute period. Freshly prepared methylsulfenyl chloride (470 mg.) in tetrahydrofuran (8 ml.) is then added. The reaction mixture is stirred for 45 minutes allowing it to gradually warm to room temperature. The resulting red-brown solution is diluted with 1.4 liters of benzene and washed successively with 600 ml. portions of water, 0.5 M pH 3 phosphate buffer, water, 0.5 M dipotassium hydrogen phosphate, water and saturated brine. The benzene solution is dried with magnesium sulfate, filtered and the filtrate is evaporated under reduced pressure to give an orange oil. Chromatography of the crude product on silica gel (110 g) using 1:9 ethylacetate-benzene as eluting solvent gives substantially pure benzhydryl 7-α-methylthio-7-(p-nitrobenzylideneamino)-1-methylenedethiacephalosporanate.

D. benzhydryl 7-amino-7-α-methylthio-1-methylene-dethiacephalosporanate

To a suspension of 300 mg. of 2,4-dinitrophenylhydrazine p-toluenesulfonate in 8 ml. of tetrahydrofuran is added a solution of benzhydryl 7-α-methylthio-7-(p-nitrobenzylideneamino)-1-methylene-dethiacephalosporanate (400 mg.) in 12 ml. of tetrahydrofuran. After stirring for 90 minutes at room temperature, the reaction mixture is filtered and the filtrate is evaporated under reduced pressure. The crude residue is taken up in 40 ml. of methylene chloride and the solution is shaken vigorously for 4 minutes with aqueous dipotassium hydrogen phosphate (272 mg. in 10 ml. of water). The organic phase is separated, washed with saturated brine, dried with magnesium sulfate and filtered. The filtrate is evaporated under reduced pressure to give benzhydryl 7-amino-7-α-methylthio-1-methylene-dethiacephalosporanate.

E. 7-α-methylthio-7-β(α-carboxy-3-thienyl)acetamido-1-methylene-dethiacephalosporanic acid bis-benzhydryl ester To a solution of 584 mg. of benzhydryl-3-thienyl malonic acid in 4 ml. of dry acetonitrile cooled to 0° C. is added 340 mg. of dicyclohexyl-carbodiimide followed immediately by a cooled solution of 250 mg. of benzhydryl 7-amino-7-α-methylthio-1-methylene-dethiacephalosporanate in 2 ml. of acetonitrile. The mixture is stirred at 0° C. for 25 minutes. The acetonitrile is rapidly evaporated in vacuo and to the residue is added 10 ml. of chloroform and 5 ml. of 10% sodium dihydrogen phosphate. The mixture is separated by centrifugation and the chloroform is extracted twice with N pH 7 phosphate buffer. The organic phase is filtered, dried over anhydrous magnesium sulfate and evaporated. The residual oil is chromatographed on silica gel using 5% ethylacetate-chloroform as eluting solvent giving 7-α-methylthio-7-β(α-carboxy-3-thienylacetamido-1-methylene-dethiacephalosporanic acid bis-benzhydryl ester.

F. disodium salt of 7-α-methoxy-7-β(α-carboxy-3-thienyl)-acetamido-1-methylene-dethiacephalosporanic acid To a solution of 7-α-methylthio-7-β(α-carboxy-3-thienyl)acetamido-1-methylene-dethiacephalosporanic acid bis-benzhydryl ester (195 mg.) in methanol (3 ml.) and tetrahydrofuran (0.5 ml.) is added a solution of thallium trinitrate trihydrate (132 mg.) in methanol (1.5 ml.). The resulting mixture is stirred at room temperature for 10 minutes and then treated with sodium bicarbonate (65 mg.). After stirring for two minutes, the mixture is filtered and the filtrate is evaporated in vacuo to dryness. The residue is dissolved in methylene chloride (10 ml.) and the solution is filtered. The filtrate is washed with 5 ml. portions of water, 5% aqueous dipotassium hydrogen phosphate and water and dried with magnesium sulfate, filtered and the filtrate is evaporated under reduced pressure to give 7-α-methoxy-7-β(α-carboxy-3-thienyl)-acetamido-1-methylene-dethiacephalosporanic acid bis-benzhydryl ester.

The ester is dissolved in a mixture of 1 ml. of anisole and 5 ml. of trifluoroacetic acid at 0° C. and stirred for 8 minutes. The reagents are removed under reduced pressure and the residue is triturated with chloroform which is removed under reduced pressure. The residue is stirred with a mixture of 10 ml. of chloroform and 40 mg. of sodium bicarbonate in 10 ml. of water. The aqueous layer is separated by centrifugation, filtered and lyophilized to give the disodium salt of 7-α-methoxy-7-β(α-carboxy-3-thienyl)acetamido-1-methylene-dethiacephalosporanic acid.

G. disodium salt of 7-α-methoxy-7-β(α-carboxy-3-thienyl)-acetamido-3-hydroxymethyl-1-methylene-dethiaceph-3-em 4-carboxylic acid 2.0 g. of disodium 7-α-methoxy-7-β(α-carboxy-3-thienyl)-acetamido-1-methylene-dethiacephalosporanate dissolved in 200 ml. of citrus acetylesterase solution is adjusted to pH 6.6 with N sodium hydroxide solution. The mixture is stirred and heated at 32° C. for six hours while the pH is maintained between 6.5 and 6.7 by the addition of N sodium hydroxide solution under the control of a pH stat. Sodium chloride (20 g.)

is added and the solution is filtered. The filtrate is overlayered with ethyl acetate, cooled to 5° C. and acidified to pH 2 with hydrochloric acid. The emulsion which forms is separated by centrifugation and the aqueous phase is extracted twice with ethyl acetate. The ethyl acetate solutions are washed once with water and extracted with sodium bicarbonate solution at pH 5.6. The sodium bicarbonate extract is freeze-dried leaving the disodium salt of 7-α-methoxy-7-β(α-carboxy-3-thienyl)acetamido-3-hydroxymethyl-1-methylene-dethiaceph-3-em-4-carboxylic acid.

H. disodium salt of 7-α-methoxy-7-β(α-carboxy-3-thienyl)-acetamido-3-carbamoyloxymethyl-1-methylene-dethiacephalosporanic acid A solution of 1 g. of disodium 7-α-methoxy-7-β(α-carboxy-3-thienyl)acetamido-3-hydroxymethyl-1-methylene-dethiaceph-3-em-4-carboxylic acid in 20 ml. of ice water is acidified to pH 2 and extracted with three 20 ml. portions of cold ethyl acetate. The ethyl acetate solutions are washed with cold saturated brine, dried with magnesium sulfate and rapidly evaporated under reduced pressure. The residue is dissolved in 50 ml. of dry tetrahydrofuran and the solution is cooled to −40° C. in a dry-ice bath. Chlorosulfonyl isocyanate (0.4 ml.) is added and the reaction mixture is stirred at −40° C. for two hours. 10 ml. of 0.1 N pH 7 phosphate buffer is added and the tetrahydrofuran is removed under reduced pressure. Ethyl acetate is added and the solution is brought to pH 2 by the addition of phosphate buffer. The mixture is stirred for one hour at room temperature, then the pH is adjusted to 7.5 by the addition of 1 N sodium hydroxide solution. The organic phase is separated and the aqueous phase is extracted with ethylacetate. The combined ethyl acetate extracts are washed with water, then extracted with aqueous sodium bicarbonate solution at pH 5.6. The sodium bicarbonate extract is lyophilized leaving the disodium salt of 7-α-methoxy-7-β(α-carboxy-3-thienyl)acetamido-3-carbamoyloxymethyl-1-methylene-dethiacephalosporanic acid.

EXAMPLE 75

7α-methoxy-7-(D-2-hydroxy-2-phenylacetamido)-3-[5(1-methyl-1,2,3,4-tetrazoyl)thiomethyl]-1-methylene-dethia-3-cephem-4-carboxylic acid sodium salt

A. 7-β-amino-3-(1-methyl-1,2,3,4-tetrazoyl-5-)thiomethyl-1-methylene-dethia-ceph-3-em-4-carboxylic acid A saturated solution of sodium bicarbonate is added with stirring to a mixture of 2.54 g. of 7β-amino-1-methylene-dethiacephalosporanic acid in 20 ml. of water and 10 ml. of acetone until the pH is 7.9. The solution is placed in a bath at 80° C. and a solution of 1.74 g. of 1-methyl-1,2,3,4-tetrazole-5-thiol is added. The mixture is stirred at 80° C. for 3 hours then cooled to 10° C. whereupon the pH is adjusted to 3.9 by the addition of 6 N hydrochloric acid. The mixture is chilled for one hour and the precipitate is recovered by filtration and washed with acetone and dried affording 7-β-amino-3-(1-methyl-1,2,3,4-tetrazoyl-5-)thiomethyl-1-methylene-dethia-ceph-3-em-4-carboxylic acid.

B. Benzhydryl 7-β-amino-3-(1-methyl-1,2,3,4-tetrazoyl-5)thiomethyl-1-methylene-dethia-ceph-3-em-4-carboxylate 3.09 g. of 7β-amino-3-(1-methyl-1,2,3,4-tetrazoyl-5)-thiomethyl-1-methylene-dethia-ceph-3-em-4-carboxylic acid is stirred 5 minutes at 25° C. in 70 ml. of dioxane with 1.7 g. of p-toluenesulfonic acid hydrate. Methanol (20 ml.) is added and the solvents are removed in vacuo. The residue is flushed twice with dioxane, then dioxane (80 ml.) is added followed by 2.9 g. of diphenyldiazomethane. After evolution of nitrogen is complete, the dioxane is removed under reduced pressure and the residue is stirred with methylene chloride (100 ml.) and water (100 ml.) containing sufficient $K_2HPO_4$ to bring the pH to 8. The layers are separated and the aqueous portion extracted with methylene chloride. The combined organic layers are dried over magnesium sulfate, filtered and evaporated leaving benzhydryl 7-β-amino-3-(1-methyl-1,2,3,4-tetrazoyl-5)-thiomethyl-1-methylene-dethia-ceph-3-em-4-carboxylate. 4-carboxylate. The crude product is chromatographed on silica gel (58 g.) using 1:9 ethylacetate-benzene as eluting solvent.

E. Benzhydryl 7-amino-7-α-methylthio-3-(1-methyl-1,2,3,4-tetrazoyl-5)thiomethyl-1-methylenedethia-ceph-3-em-4-carboxylate To a suspension of 300 mg. of 2,4-dinitrophenylhydrazine p-toluene sulfonate in 8 ml. of tetrahydrofuran is added a solution of benzhydryl 7-α-methylthio-7-(p-nitrobenzylideneamino)-3-(1-methyl-1,2,3,4-tetrazoyl-5)-thiomethyl-1-methylenedethia-ceph-3-em-4-carboxylate (512 mg) in 12 ml. of tetrahydrofuran. After stirring for 90 minutes at room temperature, the reaction mixture is filtered and the filtrate is evaporated under reduced pressure. The crude residue is taken up in 40 ml. of methylene chloride and the solution is shaken vigorously for 4 minutes with aqueous dipotassium hydrogen phosphate (272 mg. in 10 ml. of water). The organic phase is separated, washed with saturated brine, dried with magnesium sulfate and filtered. The filtrate is evaporated under reduced pressure to give benzhydryl 7-amino-7-α-methylthio-3-(1-methyl-1,2,3,4-tetrazoyl-5)thiomethyl-1-methylenedethia-ceph-3-em-4-carboxylate.

F. Benzhydryl 7-α-methylthio-7-(D-2-formyloxy-2-phenylacetamido)-3-(1-methyl-1,2,3,4-tetrazoyl-5)thiomethyl-1-methylenedethia-ceph-3-em-4-carboxylate A solution of benzhydryl 7-amino-7-α-methylthio-3(1-methyl-1,2,3,4-tetrazoyl-5)thiomethyl-1-methylenedethia-ceph-3-em-4-carboxylate (430 mg.) in 10 ml of methylene chloride is cooled in an ice-bath. D-2-Formyloxy-2-phenylacetylchloride (243 mg.) and pyridine (150 ml.) are added and the resulting solution is stirred for 25 minutes. Cold water (10 ml.) is added and the mixture is stirred for 5 minutes. The organic phase is separated and washed with cold 10-ml. portions of 1 M pH 3 phosphate buffer, water,

C. benzhydryl 7β(p-nitrobenzylideneamino)-3-(1-methyl-1,2,3,4-tetrazoyl-5)thiomethyl-1-methylene-dethiaceph-3-em-4-carboxylate A mixture of p-nitrobenzaldehyde (1.07 g.), anhydrous magnesium sulfate (18.0 g.) and benzhydryl 7-β- amino-3-(1-methyl-1,2,3,4-tetrazoyl-5)-thiomethyl-1-methylene-dethiaceph-3-em-4-carboxylate (3.37 g.) in 140 ml. of methylene chloride is stirred at room temperature for a period of 15 hours. The mixture is filtered and the filtrate is evaporated under reduced pressure to give benzhydryl 7β(p-nitrobenzylideneamino)-3-(1-methyl-1,2,3,4-tetrazoyl-5)thiomethyl-1-methylene-dethiaceph-3-em-4-carboxylate as a yellow oil.

D. benzhydryl 7-α-methylthio-7-β-(p-nitrobenzylideneamino)-3-(1-methyl-1,2,3,4-tetrazoyl-5)thiomethyl-1-methylene-dethia-ceph-3-em-4-carboxylate A solution of benzhydryl 7β(p-nitrobenzylideneamino)-3-(1-methyl-1,2,3,4-tetrazoyl-5)thiomethyl-1-methylenethiaceph-3-em-4-carboxylate (1.33 g.) in anhydrous tetrahydrofuran (35 ml.) is stirred at −78° C. under a nitrogen atmosphere. Phenyllithium (0.95 ml. of a 2.3 M solution in 7:3 benzene:ether) is added following by anhydrous dimethylformamide (44 ml.) dropwise during a six-minute period. Freshly prepared methylsulfenyl chloride (235 mg.) in tetrahydrofuran (4 ml.) is then added. The reaction mixture is stirred for 45 minutes allowing it to gradually warm to room temperature. The resulting solution is diluted with 700 ml. of benzene and washed successively with 300 ml. portions each of water, 0.5 M pH 3 phosphate buffer, water, 0.5 M dipotassium hydrogen phosphate, water and saturated brine. The benzene solution is dried over magnesium sulfate, filtered and the filtrate is evaporated under reduced pressure to give benzhydryl-7-α-methylthio-7-β-(p-nitrobenzylideneamino)-3-(1-methyl-1,2,3,4-tetrazoyl)-5)thiomethyl-1-methylene-dethia-ceph-3-em-5% dipotassium hydrogen phosphate, water and saturated brine. It is then dried with magnesium sulfate, filtered and the filtrate is evaporated under reduced pressure to give an oil. Chromatography of the crude product on silica gel (34 g.) using 1:4 ethyl acetate-benzene as eluting solvent gives substantially pure benzhydryl 7-α-methylthio-7-(D-2-formyloxy-2-phenylacetamido)-3-(1-methyl-1,2,3,4-tetrazoyl-5)thiomethyl-1-methylenedethia-ceph-3-em-4-carboxylate.

G. Benzhydryl 7α-methoxy-7(D-2-formyloxy-2-phenylacetamido)-3-(1-methyl-1,2,3,4-tetrazoyl-5)thiomethyl-1-methylene-dethia-ceph-3-em-4-carboxylate To a solution of benzhydryl 7α-methylthio-7-(D-2-formyloxy-2-phenylacetamido)-3-(1-methyl-1,2,3,4-tetrazoyl-5)thiomethyl-1-methylenedethia-ceph-3-em-4-carboxylate (170 mg.) in methanol (3 ml) and tetrahydrofuran (0.5 ml.) is added a solution of thallium trinitrate trihydrate (132 mg.) in methanol (0.5 ml.). The resulting mixture is stirred at room temperature for a period of 10 minutes and then treated with sodium bicarbonate (65 mg.). After stirring for an additional two minutes, the mixture is filtered and the filtrate is evaporated in vacuo to dryness. The residue is dissolved in 10 ml. of methylene chloride and the solution is filtered. The filtrate is washed with 5 ml. portions of water, 5% aqueous dipotassium hydrogen phosphate and water and dried with magnesium sulfate, filtered and the filtrate is evaporated under reduced pressure to give an oil. Chromatography of the crude product on silica gel (10.5 g.) using 15% ethyl acetate/benzene as eluting solvent gives substantially pure benzhydryl 7α-methoxy-7-(D-2-formyloxy-2-phenylacetamido)-3-(1-methyl-1,2,3,4-tetrazoyl-5)thiomethyl-1-methylenedethia-ceph-3-em-4-carboxylate.

H. 7-α-Methoxy-7-(D-2-formyloxy-2-phenylacetamido)-3-(1-methyl-1,2,3,4-tetrazoyl-5)thiomethyl-1-methylenedethia-ceph-3-em-4-carboxylic acid.

Trifluoroacetic acid (0.5 ml.) is added to a cold solution of benzhydryl 7α-methoxy-7-(D-2-formyloxy-2-phenylacetamido)-3-(1-methyl-1,2,3,4-tetrazoyl-5)thiomethyl-1-methylenedethia-ceph-3-em-4carboxylate (60 mg.) and anisole (0.5 ml.). The resulting solution is stirred for 5 minutes at 0° C. and then the excess trifluoroacetic acid is removed in vacuo. The residue is partitioned between aqueous sodium bicarbonate (15 mg. in 5 ml. of water) and methylene chloride (5 ml.). The aqueous phase is separated and extracted again with methylene chloride. The aqueous phase is then layered with ethylacetate (5 ml.) and acidified to pH 2.6. The aqueous phase is separated and extracted with ethyl acetate (2×5 ml.). The combined ethyl acetate solutions are dried on magnesium sulfate, filtered and the filtrate is evaporated under reduced pressure to give 7-α-methoxy-7-(D-2-formyloxy-2-phenylacetamido)-3-(1-methyl-1,2,3,4-tetrazoyl-5)thiomethyl-1-methylenedethia-ceph-3-em-4-carboxlyic acid.

I. 7-α-Methoxy-7-(D-2-hydroxy-2-phenylacetamido)-3-(1-methyl-1,2,3,4-tetrazoyl-5)thiomethyl-1-methylenedethia-ceph-3-em-4-carboxylate sodium salt A solution of 7-α-methoxy-7-(D-2-formyloxy-2-phenylacetamido)-3-(1-methyl-1,2,3,4-tetrazoyl-5)-thiomethyl-1-methylenedethia-ceph-3-em-4-carboxylic acid (30 mg.) in aqueous sodium bicarbonate (30 mg. in 0.4 ml. of water) is stirred at room temperature for three hours. The solution is diluted with 2 ml. of water, layered with 2 ml. of ethyl acetate and then acidified to pH 2.6 with pH 2 phosphate buffer. The aqueous phase is separated and extracted with ethyl acetate (2×3 ml). The combined ethyl acetate solutions are dried with magnesium sulfate, filtered and the filtrate is evaporated under reduced pressure. The residue is dissolved in 1 ml. of acetone and aqueous sodium bicarbonate (4.2 mg. in 3.2 ml. water) is added. The acetone is removed in vacuo and the aqueous solution remaining is lyophilized to give 7-α-methoxy-7-(D-2-hydroxy-2-phenylacetamido)-3-(1-methyl-1,2,3,4-tetrazoyl-5)-thiomethyl-1-methylenedethia-ceph-3-em-4-carboxylate sodium salt as a white powder.

By following the procedures illustrated in the Flow Sheets and described in detail in the Examples and by employing an appropriately substituted 2-aminophosphonate there is obtained the 7β-amino or 7-substituted imino compound II which upon treatment with an acylating agent such as an acylating agent of the formula,

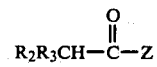

via techniques well known to the art affords those compounds wherein $A^1$ is as defined above. These compounds can be further treated if desired, by the methods described above to form other 3-substituted analogs described in the following Table I. The following equation and Table I together with Flow Sheets I and II illustrate the various products embraced by this invention:

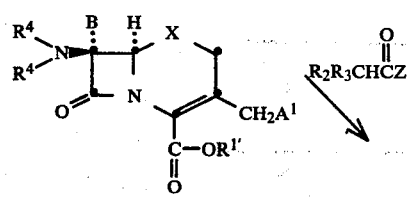 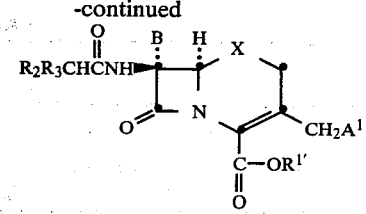

TABLE I

| Ex. No. | R | R¹ | A | X |
|---|---|---|---|---|
| 76 | phenyl-CH(NH₂)-C(O)- | $-C(CH_3)_3$ | H | O |
| 77 | 2-thienyl-CH₂-C(O)- | $-C(CH_3)_3$ | $-OCONH_2$ | $-CH_2-$ |
| 78 | 2-furyl-CH₂-C(O)- | $-CH(\phi)_2$ | $-OCOCH_3$ | $-NH-$ |
| 79 | 4-HO-phenyl-CH(NH₂)-C(O)- | $-CH(\phi)_2$ | H | $-CH_2-$ |
| 80 | thiazol-2-yl-CH₂-C(O)- | $-CH_2C(Cl)_3$ | pyridinium | O |
| 81 | phenyl-CH(tetrazol-5-yl)-C(O)- | $-CH_2-$(4-OCH₃-phenyl) | $-OCOCH_3$ | $-N(CH_3)-$ |
| 82 | 3-thienyl-CH₂-C(O)- | $-CH(\phi)_2$ | $-S-$(5-methyl-1,3,4-thiadiazol-2-yl) | $-N(CH_3)-$ |
| 83 | phenyl-CH(COOH)-C(O)- | $-CH(\phi)_2$ | $-OCOCH_3$ | $-NH-$ |
| 84 | 2-thienyl-CH(COOH)-C(O)- | $-C(CH_3)_3$ | $-OCOCH_3$ | O |
| 85 | phenyl-CH₂-C(O)- | $-CH_2-C(O)-\phi$ | $-S-$(5-methyl-1,3,4-thiadiazol-2-yl) | $-CH_2-$ |
| 86 | 3-Br-phenyl-CH₂-C(O)- | $-C(CH_3)_3$ | $-S-$(1-methyl-tetrazol-5-yl) | $-CH_2-$ |

TABLE I-continued

| Ex. No. | R | R¹ | A | X |
|---|---|---|---|---|
| 87 | NH₂CH₂-C₆H₄-CH₂C(O)- | —CH(φ)₂ | —OCOCH₃ | —O— |
| 88 | HOOC-CH₂-C₆H₄-CH₂C(O)- | —CH(φ)₂ | —OCOCH₃ | —NH— |
| 89 | H₂NC(O)-CH₂-C₆H₄-CH₂C(O)- | —CH₂-C₆H₄-OCH₃ | —OCOCH₃ | O |
| 90 | 5-NO₂-furan-2-CH₂C(O)- | —CH₂C(Cl)₃ | —N⁺(pyridinium)= | —N(CH₃)— |
| 91 | furan-3-CH₂C(O)- | —CH₂C(O)-φ | —OCOCH₃ | —CH₂— |
| 92 | 5-Cl-thiophene-2-CH₂C(O)- | —C(CH₃)₃ | —OCOCH₃ | —N(CH₃)— |
| 93 | 5-CH₃O-thiophene-2-CH₂C(O)- | —CH(φ)₂ | H | —NH— |
| 94 | thiophene-2-CH(NHC(=NH)NH₂)C(O)- | —CH(φ)₂ | —OCONH₂ | —O— |
| 95 | 5-CH₃-thiophene-2-CH₂C(O)- | —CH₂-C₆H₄-OCH₃ | H | —CH₂— |
| 96 | isothiazol-3-CH₂C(O)- | —CH₂C(Cl)₃ | —OCOCH₃ | O |
| 97 | 3-CH₃O-isothiazol-4-CH₂C(O)- | —CH₂C(Cl)₃ | H | —N(CH₃)— |
| 98 | isothiazol-4-CH₂C(O)- | —C(CH₃)₃ | —OCOCH₂ | —CH₂— |
| 99 | 3-CH₃-isothiazol-4-CH₂C(O)- | —CH(φ)₂ | H | —NH— |
| 100 | 3-Cl-isothiazol-4-CH₂C(O)- | —CH₂-C₆H₄-OCH₃ | —OCH₃ | —NH— |
| 101 | 3-CH₃-1,2,5-oxadiazol-4-CH₂C(O)- | —CH₂C(O)-φ | —OCH₃ | —N(CH₃)— |

TABLE I-continued

| Ex. No. | R | R¹ | A | X |
|---|---|---|---|---|
| 102 | 1,2,5-thiadiazol-3-yl-CH$_2$C(O)— | —CH$_2$C(O)—$\phi$ | pyridinium (—N$^+$=) | O |
| 103 | 4-methyl-1,2,5-thiadiazol-3-yl-CH$_2$C(O)— | —CH$_2$C(Cl)$_3$ | H | —CH$_2$— |
| 104 | 4-chloro-1,2,5-thiadiazol-3-yl-CH$_2$C(O)— | —CH($\phi$)$_2$ | —OCONH$_2$ | —CH$_2$— |
| 105 | 4-methoxy-1,2,5-thiadiazol-3-yl-CH$_2$C(O)— | —CH($\phi$)$_2$ | H | —N(CH$_3$)— |
| 106 | phenyl-SCH$_2$C(O)— | —C(CH$_3$)$_3$ | —OCH$_3$ | —CH$_2$— |
| 107 | pyridin-4-yl-SCH$_2$C(O)— | —C(CH$_3$)$_3$ | —S-(5-methyl-1,3,4-thiadiazol-2-yl) | —O— |
| 108 | CNCH$_2$C(O)— | —CH($\phi$)$_2$ | —OCOCH$_3$ | —CH$_2$— |
| 109 | 1H-tetrazol-1-yl-CH$_2$C(O)— | —CH($\phi$)$_2$ | —S-(5-methyl-1,3,4-thiadiazol-2-yl) | —O— |
| 110 | phenyl-CHF-C(O)— | —CH($\phi$)$_2$ | —OCOCH$_3$ | —NH— |
| 111 | thien-2-yl-CH(NH$_2$)-C(O)— | —CH$_2$C(O)—$\phi$ | H | —CH$_2$— |
| 112 | thien-3-yl-CH(NH$_2$)-C(O)— | —CH$_2$-C$_6$H$_4$-OCH$_3$ | H | —NH— |
| 113 | thien-3-yl-C(O)CH$_2$C(O)— | —C(CH$_3$)$_3$ | —OCOCH$_3$ | —N(CH$_3$)— |
| 114 | phenyl-CH(PO(OH)$_2$)-C(O)— | —CH$_2$C(Cl)$_3$ | —OCONH$_2$ | —NH— |
| 115 | phenyl-CH(NHSO$_3$H)-C(O)— | —CH($\phi$)$_2$ | —OCOCH$_3$ | —N(CH$_3$)— |
| 116 | phenyl-CH(OH)-C(O)— | —CH($\phi$)$_2$ | —S-(1-methyl-1H-tetrazol-5-yl) | —CH$_2$— |

TABLE I-continued

| Ex. No. | R | R¹ | A | X |
|---|---|---|---|---|
| 117 | phenyl-CH(-C(=O)-)-SO₂(OH) | —CH(φ)₂ | —OCONH₂ | —NH— |
| 118 | 2-thienyl-CH₂-C(=O)- | —CH₂OCH₃ | —OCOCH₃ | —O— |

It will be appreciated by one skilled in the art that the products illustrated in the chart above, wherein B=H, are merely representative of the variety and scope of compounds embraced by this invention. Corresponding novel useful antibiotic compounds wherein B=OCH₃, CH₃ or SR shall also be obtained in accordance with the teachings of the invention. It will be further appreciated that although Examples 76–118 are illustrated with respect to the ester moiety (R¹), conversion to the free acid (R¹=H) may be effected employing techniques well known to the art as indicated previously.

EXAMPLE 119

7α-Methoxy-7β-2-thienyl)acetamido-3-carbamoyloxymethyl-1-carbadethio-decephalosporanic acid

STEP A

Benzhydryl 7β-(2-thienyl)acetamido-1-carbadethiocephalosporanate

7β-(2-thienyl)acetamido-1-carbadethiocephalosporanic acid, 870 mg., is treated in 60 ml. acetonitrile with 485 mg. diphenyldiazomethane. After 1 hr., the excess diazo compound is destroyed with glacial acetic acid and the solvent removed i.v. The residue is taken up in 40 ml. benzene, washed with aqueous bicarbonate and brine, dried with MgSO₄, filtered, evaporated i.v. and chromatographed on silica gel, eluting with 3:1 benzene-EtOAc, affording 642 mg. pure benzhydryl 7β-(2-thienyl)acetamido-1-carbadethiocephalosporanate.
NMR: (δ, CDCl₃) 1.99s (Ac), 1.9–2.3m (CH₂CH₂), 3.74s (CH₂CO), 3.7m (H-6), 4.75d, 5.10d, J=13 (CH₂OAc), 5.40 d of d, J=7.5 (H-7), 6.9–7.4m (CHO₂and thienyl), 7.31s (φ). IR (μ, film): 3.0 (NH), 5.63 (β-lactam), 5.72 (ester), 5.95 (amide). MS: 544, 484, 377, 167 et al. TLC: Rf=0.4, silica gel, 4:1 CHCl₃-EtOAc.

STEP B

Benzhydryl 7α-methoxy-7β-(2-thienyl)acetamido-1-carbadethiocephalosporanate

Benzhydryl 7β-(2-thienyl)acetamido-1-carbadethiocephalopsporanate, 578 mg., in 10.6 ml. THF, is added at −46° to a solution of LiOMe in 26 ml. THF (prepared from 2.07 ml. 2.3 M φLi and 4.2 ml. MeOH). After 1 min. at −46°, 154λt-BuOCl is added. After 3 min. more, a solution of 4.2 ml. AcOH in 4.2 ml. THF is added. The reaction mixture is allowed to warm to room temperarture, diluted with benzene, stripped partially i.v., diluted again with benzene, and washed successively with water, aq. Na₂SO₃, pH 8 phosphate and brine. After drying with MgSO₄, filtration, evaporation and chromatography on silica gel, eluting with 3:1 benzene-EtOAc, pure benzhydryl 7α-methoxy-7β-(2-thienyl)acetamido-1-carbadethiocephalosporanate, 166 mg., is obtained. NMR (δ, CDCl₃): 199 s (Ac), 2.0–2.4m, (CH₂CH₂), 3.47 s (OMe), 3.78 s (CH₂CO), 3.98 d of d, J=11.3 (H-6), 4.82 d, 4.95d, J=14 (CH₂OAc), 6.9–7.4 m (CHφ₂ and thienyl), 7.34 s (φ). IR (μ, film): 3.0 (NH), 5.63 (β-lactam), 5.72 (ester), 5.9 (amide). MS: 574, 514, 407, 167 et al. TLC: RF=0.4, S.G., 3:1 benzene-EtOAc.

STEP C

Sodium 7α-methoxy-7β-(2-thienyl)acetamido-1-carbadethiocephalosporanate

Benzhydryl 7α-methoxy-7β-(2-thienyl)acetamido-1-carbadiethiocephalosporanate, 230 mg., is dissolved in 1.0 ml. anisole and treated for 2.0 min. at 0° with 5.0 ml. trifluoroacetic acid. The TFA is pumped off in the cold, then the anisole at 30°. More anisole is added and pumped off. The residue is treated with 10 ml. water and 42 mg. NaHCO₃, washed twice with CH₂Cl₂ and lyophilized, affording 168 mg. sodium 7α-methoxy-7β-(2-thienyl)acetamido-1-carbadethiocephalosporanate.
NMR (δ, D₂O): 2.40 s (acetyl), 2.3–2.6 m (CH₂CH₂), 3.78 s (OMe), 4.24 s (CH₂CO), 4.2 m (H-6, 4.99 s (HDO), 4.93 d, 5.30 d, J=17 (CH₂OAc), 7.3 d, J=3, 7.65 m (thienyl). MS of Me ester: 363, 212, 210, 152, 97 et al.

STEP D

Sodium 7α-methoxy-7β-(2-thienyl)acetamido-3-hydroxymethyl-1-carbadethio-decephalosporanate Sodium 7α-methoxy-7β-(2-thienyl)acetamido-1-carbadethiocephalosporanate, 168 mg. was dissolved in 7 ml. citrus acetyl esterase solution and maintained on the pH-start at pH 6.7 overnight at 31°. The solution was cooled to 0°, saturated with NaCl, layered with EtOAc and its pH brought to 2 with phosphate buffer. It was extracted 5 times with EtOAc. The combined EtOAc was re-extracted with water containing 66 mg. NaHCO₃. The aq extracts were lyophilized, affording 161 mg. sodium 7α-methoxy-7β-(2-thienyl)acetamido-3-hydroxymethyl-1-carbadethio-decephalosporanate admixed with NaOAc. NMR (δ, D₂O): 2.0–2.4 m, (CH₂CH₂), 3.40 s (OMe), 3.83 s (CH₂CO), 3.8 m (H-6), 4.60 s (HDO), 6.94 d, J=3, 7.25 m (thienyl), 4.09 s (CH₂OH).

STEP E

Sodium 7α-methoxy-7β-(2-thienyl)acetamido-3-carbamoyloxymethyl-1-carbadethio-decephalosporanate Sodium 7α-methoxy-7β-(2-thienyl)acetamido-3-hydroxymethyl-1-carbadethio-decephalosporanate admixed with NaOAc, 161 mg., is dissolved in 5 ml. water saturated with NaCl, layered with EtOAc at 0° and brought to pH 2 with phosphate buffer. Five extractions with EtOAc are combined, dried at 0° with MgSO$_4$, filtered and evaporated, affording the free acid of sodium 7α-methoxy-7β-(2-thienyl)-acetamido-3-hydroxymethyl-1-carbadethio-decephalosporanate. This is dissolved in 7.3 ml. THF and treated for 4 hours with 36 λ chlorosulfonyl isocyanate under N$_2$ at −40°. Then, 0.62 ml. 0.1 m pH 7 phosphate buffer is added. The solvent is stripped i.v. in the cold and the residue treated with 4.15 ml. 0.1 M pH 7 aq phosphate and 4 ml. EtOAc, stirring 1 hr. at 25°. The pH is adjusted to 8 with alkali, the EtOAc layer is separated and washed once with 4 ml. 0.1 M pH 7 phsophate, and the combined aq portions saturated with NaCl, adjusted to pH 2 and extracted 5 times with EtOAc. The EtOAc portion is dried with MgSO$_4$, filtered, evaporated and pumped 2½ hrs. at 0.050 Torr. The weight of sodium 7α-methoxy-7β-(2-thienyl)acetamido-3-carbamoyloxymethyl-1-carbadethio-decephalosporanate free acid is 62 mg. NMR (δ, acetone-D$_6$): 2.0–2.3 m (CH$_2$CH$_2$), 3.30 (OMe), 3.81 s (CH$_2$CO), 3.8 m (H-6), 4.70 d, 4.83 d, J=14 (C$\underline{H}_2$O-CONH$_2$), 5.95 m (NH), 6.83 d, J=3, 7.14 m (thienyl), 8.0 m, (NH$_2$, COOH). IR (μ, film): 3.0 (NH and OH), 5.65 (β-lactam), 5.8 (ester), 5.9 (amide). UV (sodium 7α-methoxy-7β-(2-thienyl)acetamido-3-carbamoyloxymethyl-1-carbadethio-decephalosporanate, H$_2$O): 234 nm (E% 218), 256 nm (sh, E% 175).

Sodium 7α-methoxy-7β-(2-thienyl)acetamido-3-carbamoyloxymethyl-1-carbadethio-decephalosporanate is obtained from its free acid by treatment with 17 mg. NaHCO$_3$ in aq acetone, evaporation i.v., addition of water and lyophilization. Yield 64 mg.

EXAMPLE 120

7β-(l-2-phenyl-2-hydroxyacetamido)-3-(5-[1-methyl-1,2,3,4-tetrazolyl]-thiomethyl)-1-carbadethio-decephalosporanic acid

STEP A 4,4-(2,2-dioxolanyl)-5-acetoxy pentanaldimine of p-methoxybenzyl-2-amino-2-diethylphosphonoacetate p-Methoxybenzyl-2-amino-2-diethylphosphonoacetate, 893 mg., and 490 mg. 4,4-(2,2-dioxolanyl)-5-acetoxy pentanal are stirred 2 hrs. in 70 ml. CH$_2$Cl$_2$, and then an additional hour with 300 mg. MgSO$_4$. After filtration and evaporation of the solvent, pure 4,4-(2,2-dioxolanyl)-5-acetoxy pentanaldimine of p-methoxybenzyl-2-amino-2-diethylphosphonoacetate is obtained, 1.442 g. NMR (δ, CDCl$_3$): 1.32 t, J=7, POCH$_2$C$\underline{H}_3$; 2.12 s, Ac; 3.88 s, OCH$_3$; 4.0–4.4 m, OCH$_2$CH$_2$ and OCH$_2$CH$_3$; 4.52 d, J=20, 5.23 s, OC$\underline{H}_2$Ar; 6.95, 7.40 d of d, J=9, C$_6$H$_4$, 7.88 m C$\underline{H}$=N.

STEP B p-Methoxybenzyl-2-(2-oxo-3-azido-4-[3,3{2,2-dioxolanyl}-4-acetoxybutyl]-N-azetidinyl)-2-diethylphosphonoacetate 4,4-(2,2-Dioxolanyl)-5-acetoxy pentanaldimine of p-methoxybenzyl-2-amino-2-diethylphosphonoacetate, 1.442 g. is flushed four times with dry benzene and taken up in 27 ml. benzene and 27 ml. cyclohexane. Triethylamine, 0.751 ml., is added, and then over one hour a solution of 0.471 ml. azidoacetyl chloride in 55 ml. cyclohexane. The mixture is diluted with benzene, washed with aq. pH 3 phosphate, water, aq pH 8 phosphate, brine, dried with MgSO$_4$, filtered and evaporated, affording 1.667 g. crude product. Pure p-methoxybenzyl-2-(2-oxo-3-azido-4-[3,3-{2,2-dioxolanyl}-4-acetoxybutyl]-N-azetidinyl)-2-diethylphosphonoacetate, 0.558 g., is obtained by chromatography on silica gel eluting with 2:1 cyclohexane-isopropyl alcohol. Preparative layer chromatography of mixed fractions gives additional pure p-methoxybenzyl-2-(2-oxo-3-azido-4-[3,3-{2,2-dioxolanyl}-4-acetoxybutyl]-N-azetidinyl)-2-diethylphosphonoacetate for a total of 0.787 g. IR (μ, film): 4.74 (azide), 5.65 (β-lactam), 5.73 (ester). MS: 598, 570 et al. NMR (δ, CDCl$_3$): 1.25 m, POCH$_2$C$\underline{H}_3$; 1.75 m, CH$_2$CH$_2$; 2.10 s, Ac; 3.81 s, OCH$_3$; 4.02 s, OCH$_2$CH$_2$O; 4.1 m, OC$\underline{H}_2$CH$_3$; 4.52 d, J=19, CHP; 4.7 m CHN$_3$; 5.18 s, OC$\underline{H}_2$Ar; 6.90, 7.31 d of d, J=9, C$_6$H$_4$.

STEP C

2-Oxo-3-azido-4-(3-keto-4-hydroxybutyl)-N-azetidinyl diethylphosphonoacetic acid To 6.77 g., p-methoxybenzyl-2-(2-oxo-3-azido-4-[3,3-{2,2-dioxolanyl}-4-acetoxybutyl]-N-azetidinyl)-2-diethylphosphonoacetate is added 6.4 ml. AcOH and then 51.3 ml. 10% aq. H$_2$SO$_4$. The mixture is vigorously stirred 2½ hrs. at 50°, cooled, treated with 10 g. Na$_2$SO$_4$ and extracted 10 times with CH$_2$Cl$_2$. The extracts are dried with MgSO$_4$, filtered and evaporated to provide 450 mg. 2-oxo-3-azido-4-(3-keto-4-hydroxybutyl)-N-azetidinyl diethylphosphonoacetic acid admixed with anisyl alcohol. NMR (δ, CDCl$_3$): 1.35 t, J=7, POCH$_2$C$\underline{H}_3$; 2.1 m, CH$_2$CH$_2$; 2.5 m, OH; 3.80 s, OMe (An. Alc.); 4.22 s, COC$\underline{H}_2$OH; 4.0–4.4 m, POC$\underline{H}_2$CH$_3$; 4.58 s, OC$\underline{H}_2$Ar (An. Alc.); 4.8 m CHN$_3$; 6.89, 7.15 d of d, J=9, C$_6$H$_4$. IR (μ, film): 4.72, azido; 5.65, β-lactam; 5.72, ester; 2.85 broad H-bonded, OH.

STEP D

Benzhydryl (2-oxo-3-azido-4-[3-keto-4-hydroxybutyl]-N-azetidinyl)diethylphosphonoacetate To 450 mg. 2-oxo-3-azido-4-(3-keto-4-hydroxybutyl)-N-acetidinyl diethylphosphonoacetic acid in 36 ml. MeCN is added portionwise 220 mg. diphenyldiazomethane. After ½ hour, a little AcOH is added, the solvent evaporated and the residue chromatographed on 21 g. silica gel with EtOAc, affording 251 mg. pure benzhydryl (2-oxo-3-azido-4-[3-keto-4-hydroxybutyl]-N-azetidinyl)diethyl phosphonoacetate. NMR (δ, CDCl$_3$): 1.22 m, POCH$_2$C$\underline{H}_3$; 2.05–2.45 m, CH$_2$CH$_2$; 3.15 m, OH; 4.15 s, COC$\underline{H}_2$OH; 4.0–4.4 m, POC$\underline{H}_2$CH$_3$; 4.8 m, CHN$_3$; 6.96 s, C$\underline{H}$φ$_2$; 7.38 s, Ar. IR (μ, film): 2.85, OH; 4.73, azide; 5.64, β-lactam; 5.73, ester. MS (silylated): 602, M$^+$—N$_2$, et al.

STEP E

Benzhydryl (2-oxo-3-azido-4-[3-keto-4-methanesulfonyloxybutyl]-N-azetidinyl)diethylphosphonoacetate Benzhydryl (2-oxo3-azido-4-[3-keto-4-hydroxybutyl]-N-azetidinyl)diethylphosphonoacetate, 251 mg., is treated at 0° under N$_2$ in 22 ml. CH$_2$Cl$_2$ with 0.056 ml. methanesulfonyl chloride for 5 min., and then .100 ml. triethylamine is added. After 2 min. more at 0° and 30 min. at 25°, the solvent is evaporated and the product chromatographed by PLC, eluting with 10:3 CHCl$_3$-acetone, affording 197 mg. pure benzyhydryl (2-oxo-3-azido-4-[3-keto-4-methanesulfonyloxybutyl]-

N-azetidinyl)diethylphosphonoacetate. NMR (δ, CDCl$_3$): 1.24 m, POCH$_2$CH$_3$; 2.0–2.5 m, CH$_2$CH$_2$; 3.14 s, CH$_3$SO$_2$; 3.8–4.4 m, POCH$_2$CH$_3$; 4.71 s, COCH$_2$OSO$_2$Me; 5.09 d, J=22, CHP; 6.93 s, CHφ$_2$; 7.36 s, Ar. IR (μ, film): 4.73, azido; 5.64, β-lactam; 5.72, ester.

STEP F

Benzhydryl (2-oxo-3-azido-4-[3-keto-4-{5-[1-methyl-1,2,3,4-tetrazolyl]-thio}]-N-azetidinyl)diethylphosphonoacetate Benzhydryl (2-oxo-3-azido-4-[3-keto-4-methanesulfonyloxybutyl]-N-azetidinyl)diethylphosphonoacetate, 179 mg., is treated in 11 ml. MeCN with 36 mg. 1-methyl-5-sulfhydryl-1,2,3,4-tetrazole and then with 36 mg. 57% NaH dispersion. After stirring overnight at room temperature under N$_2$, benzhydryl (2-oxo-3-azido-4-[3-keto-4-{5-[1-methyl-1,2,3,4-tetrazolyl]-thio}]-N-azetidinyl)diethylphosphonoacetate is obtained, which is carried forward to benzhydryl 7β-azido-3-(5-[1-methyl-1,2,3,4-tetrazolyl]-thiomethyl)-1-carbadethio-decephalosporanate without purification.

STEP G

Benzhydryl 7β-azido-3(5-[1-methyl-1,2,3,4-tetrazolyl]-thiomethyl)-1-carbadethio-decephalosporanate The crude reaction mixture containing benzhydryl (2-oxo-3-azido-4-[3-keto-4-{5-[-methyl-1,2,3,4-tetrazolyl]-thio}]-N-azetidinyl)diethylphosphonoacetate above is heated 1¼ hours at 41°, evaporated, treated with brine and extracted four times with CH$_2$Cl$_2$. The organic extracts are dried with MgSO$_4$, filtered, evaporated and chromatographed on silica gel with 10:1 CHCl$_3$-acetone, affording 69 mg. pure benzhydryl 7β-azido-3-(5-[1-methyl-1,2,3,4-tetrazolyl]-thiomethyl)-1-carbadethio-decephalosporanate. NMR (δ, CDCl$_3$): 1.6–2.8 m, CH$_2$CH$_2$, 3.8 m, 6—H; 3.86 s, CH$_3$; 4.27, 4.40 d of d, J=12, CH$_2$S; 4.96 d, J=5, 7—H; 6.92 s, CHφ$_2$; 7.40 Ar. IR (μ, film): 4.71, azido; 5.63, β-lactam; 5.80, ester. MS: 474, 419 et al.

STEP H

Benzhydryl 7β-amino-3-(5-[1-methyl-1,2,3,4-tetrazolyl]-thiomethyl-1-carbadethio-decephalosporanate Benzhydryl 7β-azido-3-(5-[1-methyl-1,2,3,4-tetrazolyl]-thiomethyl)-1-carbadethio-decephalosporanate, 351 mg., is treated in 9.6 ml. CHCl$_3$ with 0.512 ml. Et$_3$N. Nitrogen is bubbled through, and then H$_2$S for 15 min. The solution is evaporated and flushed three times with benzene, affording crude benzhydryl 7β-amino-3-(5-[1-methyl-1,2,3,4-tetrazolyl]-thiomethyl)-1-carbadethiodecephalosporanate suitable for the next step. IR (μ, film): 2.9, NH$_2$; 5.66, β-lactam; 5.80, ester; no azide band. NMR (δ, CDCl$_3$): 1.6–2.8 m, CH$_2$CH$_2$; 3.8 m, 6—H; 3.75 s, CH$_3$; 4.24, 4.34 d of d, J=12, CH$_2$S; 4.48 d, J=5, 7—H; 6.89 s, CHφ$_2$; 7.32 s, Ar.

STEP I

Benzhydryl 7β-(l-2-phenyl-2-formyloxy acetamido)-3-(5-[1-methyl-1,2,3,4-tetrazolyl]-thiomethyl)-1-carbadethiodecephalosporanate and Benzhydryl 7β-(l-2-phenyl-2-hydroxy acetamido)-3-(5-[1-methyl-1,2,3,4-tetrazolyl]-thiomethyl)-1-carbadethio-decephalosporanate To the crude benzhydryl 7β-amino-3-(5-[1-methyl-1,2,3,4-tetrazolyl]-thiomethyl)-1-carbadethio-decephalosporanate from the previous preparation in 30 ml. CH$_2$Cl$_2$ is added 0.5 ml. pyridine and then, over ½ min., 0.236 ml. l-phenyl formyloxy acetyl chloride. After 30 min., the reaction mixture is evaporated, taken up in 30 ml. benzene, washed successively with water, pH 3 aq phosphate, water, pH 8 aq phosphate and brine, dried with MgSO$_4$, filtered, evaporated and chromatographed on silica gel with 10:1 CHCl$_3$-acetone, affording pure benzhydryl 7β-(l-2-phenyl-2-formyloxy acetamido)-3-(5-[1-methyl-1,2,3,4-tetrazolyl]-thiomethyl)-1-carbadethio-decephalosporanate and benzhydryl 7β-(l-2-phenyl)-2-hydroxy acetamido)-3-(5-[1-methyl-1,2,3,4-tetrazolyl]-thiomethyl)-1-carbadethio-decephalosporanate in that order. NMR of benzhydryl 7β-(l-2-phenyl-2-formyloxyacetamido)-3-(5-[1-methyl-1,2,3,4-tetrazolyl]-thiomethyl)-1-carbadethio-decephalosporanate (δ, CDCl$_3$): 1.4–2.6 m, CH$_2$CH$_2$; 3.8 m, 6—H; 3.83 s, CH$_3$; 4.2 m, CH$_2$S; 5.35 m, 7—H; 6.15 m, φCH; 6.89 s, CHφ$_2$; 7.4 s, CHφ$_2$; 8.10 s, OCHO. IR of benzhydryl 7β-(l-2-phenyl-2-formyloxy acetamido)-3-(5-[1-methyl-1,2,3,4-tetrazolyl]-thiomethyl)-1-carbadethio-decephalosporanate (μ, film): 3.0, NH; 5.65, β-lactam; 5.78, ester, 5.91 sh, amide. NMR of benzhydryl 7β-(l-2-phenyl-2-hydroxy acetamido)-3-(5-[1-methyl-1,2,3,4-tetrazolyl]thiomethyl)-1-carbadethio-decephalosporanate (δ, CDCl$_3$): Same as benzhydryl 7β-(l-2-phenyl-2-formyloxy acetamido)-3-(5-[1-methyl-1,2,3,4-tetrazolyl]thiomethyl)-1-carbadethio-decephalosporanate except OCHO absent, and φCH is a singlet at 5.19. IR (μ,film): 2.9–3.0, OH and NH; 5.65, β-lactam; 5.80, ester; 5.95 amide.

STEP J

Sodium 7β-(l-2-phenyl-2-hydroxyacetamido)-3-(5-[1-methyl-1,2,3,4-tetrazolyl]thiomethyl)-1-carbadethio-decephalosporanate and free acid Benzhydryl 7β-(l-2-phenyl-2-formyloxy acetamido)-3-(5-[1-methyl-1,2,3,4-tetrazolyl]thiomethyl)-1-carbadethio-decephalosporanate, 215 mg., is dissolved in 0.5 ml. anisole, cooled to 0° and treated with 2.5 ml. trifluoroacetic acid for 2.0 min. The TFA is pumped off at 0.1 torr and then the anisole. More anisole, 1 ml., is added and pumped off. To the residue is added 15 ml. water and 200 mg. NaHCO$_3$, and the solution washed twice with CH$_2$Cl$_2$. After 3 hrs. at room temperature, the aq portion is made to pH 2 with phosphoric acid, saturated with NaCl and extracted 5 times with EtOAc. The extracts are dried with MgSO$_4$, filtered and evaporated to afford 133 mg. pure free acid. NMR (δ, acetone-d$_6$): 1.7–2.8 m, CH$_2$CH$_2$; 3.9 m, 6—H; 3.95 s, CH$_3$; 4.32 s, CH$_2$S; 5.12 s, φCH; 5.45 d of d, J=8, 5, 7—H, 7.38 m, C$_6$H$_5$; 8.27 d, J=8, NH; 8.87 m, OH. IR (μ, film): 3.0 broad, OH; 5.64, β-lactam; 5.76, COOH; 5.95 sh, amide. A sample converted to the Me ester with CH$_2$N$_2$ had MS 458 et al. The free acid is converted to the Na salt of sodium 7β-(l-2-phenyl-2-hydroxyacetamido)-3-(5-[1-methyl-1,2,3,4-tetrazolyl]thiomethyl)-1-carbadethio-decephalosporanate by adding water and 30 mg. NaHCO$_3$, and lyophilizing; yield 129 mg. UV (H$_2$O): E% 234 at 267 nm.

EXAMPLE 121

7β-(l-2-phenyl-2-hydroxyacetamido)-3-(5-[1-methyl-1,2,3,4-tetrazolyl]-thio)methyl-1-oxadethio-decephalosporanic acid

STEP A

1-Acetoxy-2-oxo-3-(5-[1-methyl-1,2,3,4-tetrazolyl]thio)-propane

A mixture of 58 mg. 1-methyl-5-sulfhydryl-1,2,3,4-tetrazole, 76 mg., 1-chloro-3-acetoxy-acetone, 73 mg. powdered $K_2CO_3$ and 5 ml. acetone is stirred overnight under nitrogen, filtered, and chromatographed on silica gel with 4% AcOH in $CHCl_3$, affording 77 mg. pure 1-acetoxy-2-oxo-3-(5-[1-methyl-1,2,3,4-tetrazolyl]thio)-propane, m.p. 92°. NMR (δ, $CDCl_3$): 2.12 s, Ac; 3.96 s, NMe; 4.31 s, $CH_2S$; 4.89 s, $CH_2O$. MS: 230, 188, 157, 130, 116 et al.

STEP B

1-Hydroxy-2-oxo-3-(5-[1-methyl-1,2,3,4-tetrazolyl]thio)-propane

1-Acetoxy-2-oxo-3-(5-[1-methyl-1,2,3,4-tetrazolyl]-thio)-propane, 5.52 g., is heated in 410 ml. 10% $H_2SO_4$ for 1½ hrs., cooled, treated with 88 g. $Na_2SO_4$, and extracted 8 times with $CH_2Cl_2$. The extracts are dried with $MgSO_4$, filtered and evaporated to yield 1.7 g. 1-hydroxy-2-oxo-3-(5-[1-methyl-1,2,3,4-tetrazolyl]thio)-propane. NMR (δ, $CDCl_3$): 3.95 s, NMe; 4.32 s, $CH_2S$; 4.46 s, $CH_2O$.

STEP C p-Methoxybenzyl S-methyl-thioformimino-diethylphosphonoacetate

A mixture of 375 mg. p-methoxybenzyl thioformamido-diethylphosphonoacetate, 152 mg. powdered $K_2CO_3$, 0.075 ml. MeI and 9 ml. acetone is stirred overnight under nitrogen, filtered and evaporated to afford 411 mg. p-methoxybenzyl S-methyl-thioformimino-diethylphosphonoacetate. NMR (δ, $CDCl_3$): 1.30 t, J=7, $POCH_2CH_3$; 2.45 s, SMe; 3.85 s, OMe; 4.20 m, $POCH_2$, 4.74 d, J=20, CHP; 5.23 s, $OCH_2Ar$; 6.97 d, 7.37 d, J=9, $C_6H_4$; 8.50 d, J=4, CH=N.

STEP D p-Methoxybenzyl-2-(2-oxo-3-azido-4-methylthio-N-azetidinyl)-2-diethyl phosphonoacetate To 411 mg. p-methoxybenzyl S-methyl-thioformiminodiethylphosphonoacetate in 6½ ml. $CH_2Cl_2$ at 0° under nitrogen is added 0.131 ml. azidoacetyl chloride and then, over 40 min., a solution of 0.208 ml. triethylamine in 3 ml. $CH_2Cl_2$. The mixture is stirred 30 min. more at 25° and then 3 min. with 5 ml. 1M aq $K_2HPO_4$. The organic layer is separated, dried with $MgSO_4$, filtered and chromatographed on silica gel with 10:1 $CHCl_3$-acetone to obtain 375 mg. pure p-methoxybenzyl-2-(2-oxo-3-azido-4-methylthio-N-azetidinyl)-2-diethyl phosphonoacetate. NMR (δ, $CDCl_3$): 1.25 t, J=7, $POCH_2CH_3$; 2.10 s, SMe; 3.77 s, OMe; 4.15 m, $POCH_2$; 4.5–4.9 m, CHCH and CHP; 5.19 s, $OCH_2Ar$; 6.90 d, 7.27 d, J=9, $C_6H_4$. IR (μ, film): 4.72, azide; 5.60, β-lactam; 5.73, ester.

STEP E p-Methoxybenzyl-2-(2-oxo-3-azido-4-chloro-N-azetidinyl)-2-diethyl phosphonoacetate To 375 mg. p-methoxybenzyl-2-(2-oxo-3-azido-4-methylthio-N-azetidinyl)-2-diethyl phosphonoacetate in 1.9 ml. $CCl_4$ at 0° is added 1.0 ml. of a solution of 0.46 ml. liquified chlorine in 10 ml. $CCl_4$. The mixture is stirred 2 min. at 0° and 2 min. at 25°, evaporated, and flushed 2 times with benzene to provide 405 mg. p-methoxybenzyl-2-(2-oxo-3-azido-4-chloro-N-azetidinyl)-2-diethyl phosphonoacetate. NMR (δ, $CDCl_3$): 1.28 t, J=6, $POCH_2CH_3$; 3.80 s, OMe; 4.15 m, $POCH_2$; 4.5–5.1 m, $CHN_3$ and CHP; 5.20 s, $OCH_2Ar$; 5.6–6.3 m, CHCl; 6.91 d, 7.22 d, J=9 $C_6H_4$. IR (μ, film): 4.72, azide, 5.56, β-lactam; 5.72, ester.

STEP F p-Methoxybenzyl-2-(2-oxo-3-azido-4-[2-oxo-3-[5{1-methyl-1,2,3,4-tetrazolyl}thio]propoxy]-N-azetidinyl)-2-diethylphosphonoacetate To ½ millimole p-methoxybenzyl-2-(2-oxo-3-azido-4-chloro-N-azetidinyl)-2-diethyl phosphonoacetate and 2½ millimoles 1-hydroxy-2-oxo-3-(5-[1-methyl-1,2,3,4-tetrazolyl]thio)propane in 1 ml. MeCN is added 58 mg. $Ag_2O$ and 130 mg. $AgBF_4$ with vigorous stirring, at 0°. The mixture is stirred at 25° 30 min., diluted with $CH_2Cl_2$, filtered, washed with aq $K_2HPO_4$, filtered again, dried with $MgSO_4$, filtered and chromatographed on silica gel using ethyl acetate to afford 35 mg. p-methoxybenzyl-2-(2-oxo-3-azido-4-[2-oxo-3-[5{1-methyl-1,2,3,4-tetrazolyl}thio]propoxy]-N-azetidinyl)-2-diethylphosphonoacetate. NMR (δ, $CDCl_3$): 1.0–1.4 m, $POCH_2CH_3$, 3.75 s, OMe, 3.92 s, NMe; 4.0–4.4 m, $POCH_2$; 4.6 m, $OCH_2CO$, $CHN_3$ and CHP; 5.15 s, $OCH_2Ar$; 5.3–5.8 m, CHO; 6.86 d, J=9, $C_6H_4$. IR (μ, film): 4.74, azide; 5.59, β-lactam; 5.74, ester. MS: 496, 116 et al.

STEP G p-Methoxybenzyl 7β-azido-3-(5-[1-methyl-1,2,3,4-tetrazolyl]-thiomethyl-1-oxadethio-decephalosporanate p-Methoxybenzyl-2-(2-oxo-3-azido-4-[2-oxo-3-[5{1-methyl-1,2,3,4-tetrazolyl}thio]propoxy]-N-azetidinyl)-2-diethylphosphonoacetate, 57 mg., and 5.0 mg. 50% NaH are stirred overnight under $N_2$ in 1 ml. glyme at 25°. The reaction mixture is diluted with $CH_2Cl_2$ and washed with brine, which in turn is washed 3 times with $CH_2Cl_2$. The combined organic extracts are dried with $MgSO_4$, filtered and chromatographed on silica gel with 10:1 $CHCl_3$-acetone affording 6 mg. pure p-methoxybenzyl 7β-azido-3-(5-[1-methyl-1,2,3,4-tetrazolyl]thiomethyl-1-oxadethio-decephalosporanate. NMR (δ, $CDCl_3$): 3.73 s, OMe, 3.81 s, NMe; 4.21 d, 4.28 d, J=12, $CH_2S$, 4.5–4.6 m, $OCH_2$ and $CHN_3$; 5.00 d, J=4, 6—H; 5.16 s, $OCH_2Ar$; 6.84 d, 7.24 d, J=9 $C_6H_4$. IR (μ, film): 4.72, azide, 5.58, β-lactam; 5.81, ester. MS: 458, 430 et al.

STEP H p-Methoxybenzyl 7β-amino-3-(5-[1-methyl-1,2,3,4-tetrazolyl]-thiomethyl-1-oxadethio-decephalosporanate p-Methoxybenzyl 7β-azido-3-(5-[1-methyl-1,2,3,4-tetrazolyl]thiomethyl-1-oxadethio-decephalosporanate, 30 mg., is hydrogenated at 45 PSI in 3 ml. dioxane for 6 hrs. with 40 mg. 10% Pd/C (Bolhoffer), filtered and evaporated, affording 29 mg. p-methoxybenzyl 7β-amino-3-(5-[1-methyl-1,2,3,4-tetrazolyl]thiomethyl-1-oxadethio-decephalosporanate. IR (μ, film): 3.0, NH$_2$; 5.69, β-lactam; 5.80, ester.

STEP I p-Methoxybenzyl 7β-(l-2-phenyl-2-formyloxy acetamido)-3-(5[1-methyl-1,2,3,4-tetrazolyl]thio)methyl-1-oxadethio-decephalosporanate To 82 mg. p-methoxybenzyl 7β-amino-3-(5-[1-methyl-1,2,3,4-tetrazolyl]thio)methyl-1-oxadethio-decephalosporanate in 2 ml. CH$_2$Cl$_2$ is added 0.030 ml. l-phenyl-formyloxy acetyl chloride and then 0.020 ml. pyridine. After 2 min. stirring, 1 ml. water is added, and after ½ min., 0.75 ml. 1M aq pH2 phosphate. Benzene is added and the organic layer separated, washed with water, aq pH 8 phosphate and brine, dried with MgSO$_4$, filtered, and chromatographed on silica gel with 10:3 CHCl$_3$-acetone to provide 24 mg. pure p-methoxybenzyl 7β-(l-2-phenyl-2-formyloxy acetamido)-3-(5-[1-methyl-1,2,3,4-tetrazolyl]thio)-methyl-1-oxadethio-decephalosporanate. NMR (δ, CDCl$_3$): 3.80 s, OMe; 3.90 s, NMe, 4.30 s, CH$_2$S; 4.62 m, OCH$_2$; 5.04 d, J=4, 6—H; 5.24 s, OCH$_2$Ar; 5.60 d of d, J=4, 9, 7—H; 6.27 s, φCHOCHO; 6.92 d, 7.30 d, J=9, C$_6$H$_4$; 7.41 s, C$_6$H$_5$; 8.13 s, φCHOCHO. IR (μ, film): 5.59, β-lactam; 5.80, ester; 5.90, amide; 3.05, NH. MS: 594, 478, 473, 376, 357, 121, 116 et al.

STEP J

Sodium 7β-(l-2-phenyl-2-hydroxyacetamido)-3-(5-[1-methyl-1,2,3,4-tetrazolyl]thio)methyl-1-oxadethio-decephalosporanate and free acid p-Methoxybenzyl 7β-(l-2-phenyl-2-formyloxy acetamido)-3-(5-[1-methyl-1,2,3,4-tetrazolyl]thio)methyl-1-oxadethio-decephalosporanate, 8 mg., is dissolved in 0.1 ml. anisole and treated at 0° for 2.0 min. with 0.5 ml. trifluoroacetic acid. The TFA and anisole are pumped off at 0.1 torr and the residue flushed with more anisole. One ml. water and 8 mg. NaHCO$_3$ are added. The aq portion is washed with CH$_2$Cl$_2$, kept 3 hrs. at 25°, acidified to pH 2 with aq phosphate, saturated with NaCl and extracted 6 times with ethyl acetate. The extracts are dried with MgSO$_4$, filtered and evaporated to give 5 mg. of the free acid of sodium 7β-(l-2-phenyl-2-hydroxyacetamido)-3-(5-[1-methyl-1,2,3,4-tetrazolyl]thio)methyl-1-oxadethio-decephalosporanate. NMR (δ, acetone-d$_6$): 3.99 s, NMe, 4.37 s, CH$_2$S; 4.73 m, OCH$_2$; 5.21, s and d, J=4, φCHOH and 6—H; 5.67 d of d, J=4, 9, 7—H, 7.36 m, C$_6$H$_5$, 7.8 m, OH and NH. IR (μ, film): 3.0 broad, OH and NH; 5.57, β-lactam; 5.85, COOH; 5.93, amide.

The acid is converted to the sodium salt of sodium 7β-(l-2-phenyl-2-hydroxyacetamido)-3-(5-[1-methyl-1,2,3,4-tetrazolyl]thio)methyl-1-oxadethio decephalosporanate by adding water and 2.5 mg. NaHCO$_3$, and lyophilizing; yield 6 mg. UV (H$_2$O): E% 183 at 264 nm.

EXAMPLE 122

Sodium dl-7α-methoxy-7-(2-thienylacetamido)-1-oxadethiacephalosporante

STEP A 1-(p-methoxybenzyloxycarbonyldiethylphosphono)-methyl3-azido-4-(3'-acetoxy-2'-oxo)-propyloxy-2-azetidinone 6.4 g. of p-methoxybenzyl-2-(2-oxo-3-azido-4-chloro-N-azetidinyl)-2-diethylphosphonoacetate (prepared according to Example 121, Step E) is dissolved in 30 ml. of anhydrous methylene chloride followed by addition of 10.0 ml. of freshly distilled 1,3-dihydroxy-2-propanone-monoacetate. The mixture is stirred for 10 minutes at 0°-5°, under N$_2$. To the solution is added a mixture of 3.2 g. of silver fluoroborate and 1.6 g. of silver oxide, and the mixture is stirred vigorously for ½ hour at room temperature. The reaction mixture is then diluted with methylene chloride and filtered through supercel. The filtrate is evaporated in vacuo, and the residue is then taken up in benzene, and washed with pH 7 phosphate buffer three times and once with brine. The organic layer is dried with magnesium sulfate, filtered and evaporated in vacuo to a crude product (7.42 g.) containing 1-(p-methoxybenzyloxycarbonyl-diethyl (phosphono)-methyl-3-azido-4-(3'-acetoxy-2'-oxo)propyloxy-2-azetidinone.

STEP B p-Methoxybenzyl-7-azido-1-oxadethiacephalosporante

Sodium hydride (1.28 g. of a 57% dispersion in mineral oil) is thoroughly washed with dry hexane. A solution of crude 1-(p-methoxybenzyloxycarbonyldiethylphosphono)-methyl-3-azido-4-(3'-acetoxy-2'-oxo)-propyloxy-2-azetidinone as prepared above in 26.0 ml. of dry glyme is added to the hydride under N$_2$. The mixture is stirred under nitrogen for 2½ hours at room temperature. The reaction mixture is diluted with benzene and washed with pH 2 phosphate buffer, water, pH 9 phosphate buffer, water and brine. The organic layer is dried over magnesium sulfate, filtered, and evaporated in vacuo to a crude product (4.2 g.). The crude cephem derivative is purified by column chromatography on EM silica gel (300 g.) using 1:1 benzene-ethylacetate as eluting solvent to give p-methoxybenzyl-7-azido-1-oxadethiacephalosporanate, 986.0 mg., as a mixture of 7-isomers. IR (film)λ4.72μ (azide), 5.58μ (β-lactam), 5.75μ (ester). NMR (CDCl$_3$): δ7.28 A$_2$B$_2$ (aromatic), 5.25 s (CH$_2$Ar), 5.01–4.50 m (β-lactam protons); 4.08 s (OCH$_2$) and 3.8 s (O—CH$_3$); 2.16 s

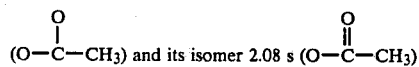

STEP C p-Methoxybenzyl-7-(2-thienylacetamido)-1-oxadethiacephalosporanate

A mixture of p-methoxybenzyl-7-azido-1-oxadethiacephalosporanate (493 mg.), 10% palladium on carbon (246 mg.), and dioxane (25 ml.) is hydrogenated at 41-42 psi for 25 hours at room temperature. The catalyst is filtered off and washed with methylene chloride (3x). The combined filtrates and washings are evaporated in vacuo to give p-methoxy-7-amino-1-oxade-thiacephalosporanate, which is immediately thienylated in 25 ml. of methylene chloride. The solution is cooled to 0° and 515.4 mg. of potassium monophosphate in 80 ml. of of water is added. With vigorous stirring under N₂ is added 224 μl. of thienyl acid chloride in 6.0 ml. of methylene chloride, and the reaction is allowed to proceed for ½ hour at 0°. Towards the end of the reaction, 150 μl. of pyridine is added, and the reaction continues for another 20 minutes with stirring at 0° under N₂. The organic layer is separated, washed twice with water, once with pH 2 phosphate buffer, twice with water, and finally with brine twice. The organic layer is dried with magnesium sulfate, and evaporated in vacuo to a crude product (656.0 mg.) which is purified by column chromatography on EM silica gel (350 g.) using 1:1 benzene-ethylacetate to give 356 mg. of p-methoxybenzyl-(2-thienylacetamido)-1-oxa-dethiacephalosporanate as a mixture of 7-isomers. IR (film)λ: 3.0 λμ(NH); 5.65 (β-lactam), 5.78 (ester); 5.92, 6.18 and 6.38μ (aromatics and amide). NMR (CDCl₃): δ7.2–6.97 m (aromatics and NH), 5.23 s (OCH₂Ar), 5.01–4.92 m(CH₂OAc, H₇ for both cis and trans isomers), 4.5 m(H₆), 4.4 broad (OCH₂), 3.85 m(OCH₃, thienyl CH₂) and

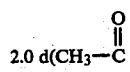
2.0 d(CH₃—C)

and its isomer).

STEP D p-Methoxybenzyl dl-7α-methoxy-7-(2-thienylacetamido)-1-oxade-thiacephalosporanate Phenyllithium (1.45 ml. of 2M solution) and anhydrous methanol (8.92 ml.) are added with stirring to ice-cold, anhydrous tetrahydrofuran (20 ml.) under N₂. The resulting solution is cooled to −70° (dry ice-acetone) and treated with a solution of p-methoxybenzyl dl-7-(2-thienylacetamido)-1-oxa-dethiacephalosporanate (356.4 mg.) in dry tetrahydrofuran (80 ml). After stirring for 2 minutes at −70°, the reaction mixture is treated with t-butyl hypochlorite (110 μl.) and stirred for an additional 10 minutes. Glacial acetic acid (34 μl.) is then added, and the reaction mixture is concentrated in vacuo. The residue is then dissolved in methylene chloride, and the solution is washed with dilute aqueous sodium thiosulfate (2%), aqueous pH 9 phosphate buffer, and finally with saturated brine. The methylene chloride solution is dried over magnesium sulfate, filtered and evaporated in vacuo to yield crude p-methoxybenzyl-dl-7α-methoxy-7-(2-thienylacetamido)-1-oxadethiacephalosporanate. The crude is purified by preparative layer chromatography on silica gel using 1:1 benzene-ethyl acetate as developing solvent to give 157.0 mg. of p-methoxybenzyl-dl-7α-(2-thienylacetamido)-1-oxa-dethiacephalosporanate. IR (film)λ 2.8–3.0μ, (NH), 5.60μ (β-lactam), 5.78 (ester); 5.82, 6.2 and 6.32 (aromatics and amide). NMR (CDCl₃): 7.2–6.97 m (aromatic and NH protons); 5.23 s (OCH₂ Ar); 5.01–4.92 m (CH₂OAc); 4.4 broad (OCH₂and H₆); 3.85 s(OCH₃); 3.8 s(O—CH₃ at 7 position);

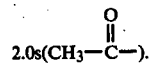
2.0s(CH₃—C—).

STEP E

Sodium dl-7α-methoxy-7-(2-thienylacetamido)-1-oxade-thiacephalosporanate

To an ice-cold mixture of p-methoxybenzyl dl-7α-methoxy-7-(2-thienylacetamido)-1-oxa-dethiacephalosporanate (10 mg.) and anisole (0.08 ml.) is added ice-cold trifluoroacetic acid (0.3 ml.). The mixture is swirled to make it homogeneous, and then kept at 0° for 3 minutes. The trifluoroacetic acid is evaporated in vacuo at 0°, and the residue is warmed to 35° in vacuo. The remaining oil is diluted with water (2 ml.) containing 16.8 mg. of sodium bicarbonate, and extracted with methylene (2×2 ml.). The aqueous portion is acidified to pH 2.6 with pH 2 phosphate buffer, and extracted with ethyl acetate (3×7 ml.). The combined ethyl acetate extracts are dried over magnesium sulfate, filtered, and evaporated in vacuo to provide dl-7α-methoxy-7-(2-thienylacetamido)-1-oxa-dethiacephalosporanic acid.

The free acid is stirred with sodium bicarbonate (1.68 mg.) in water (2.0 ml.) for 20 minutes under a stream of nitrogen. The resulting mixture is washed with ethyl acetate (2×10 ml.). The aqueous phase is separated, concentrated in vacuo to remove dissolved ethyl acetate, and lyophilized to afford sodium d,l-7α-methoxy-7-(2-thienylacetamido)-1-oxa-dethiacephalosporate (4.3 mg.) as white amorphous powder. IR (Nj) λ 3.1 NH(broad); 5.62μ (β-lactam); 6.4 (carboxylate anion). NMR (D₂O): δ 7.2–6.97 m (aromatic); 5.09–4.92 m

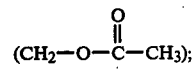
(CH₂—O—C—CH₃);

4.4 s and 4.2s (OCH₂) and H₆); 3.8 s

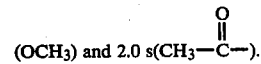
(OCH₃) and 2.0 s(CH₃—C—).

U.V. (pH 7 buffer) λ max 232 (ε8700) and 255 (ε5880) nm.

EXAMPLE 123 dl-7β-(D-α-amino-phenylacetamido)-3-methyl-1-oxaceph-3-em-4-carboxylic acid

STEP A 1-(Benzyloxy-carbonyl-diethylphosphono)-methyl-3-azido-4-chloro-2-azetidinone 1.9 g. of 1-(benzyloxycarbonyl-diethylphosphono)-methyl-3-azido-4-(methylthio)-2-azetidinone (prepared according to Example 3, Step C) is dissolved in 7.0 ml. of CCl₄, and treated with 3 ml. of a solution of 0.3 g. chlorine in CCl₄ at 0°–5°. The solution is stirred in the cold for 2 minutes, and then for additional 2 minutes at room temperature. The solvent is removed under reduced pressure to give 1.30 g. of 1-(benzyloxycarbonyl-diethylphosphono)-methyl-3-azido-4-chloro-2-azetidinone. NMR (CDCl₃)δ: 7.27 s(C₆H₅); 5.26 s (CH₂—C₆H₅); 5.01–4.92 (β-lactam protons); 4.09 q (OCH₂—CH₃); 1.23 t (CH₃—CH₂—O). Absence of singlet in the S—CH₃ proton region.

STEP B 1-(Benzyloxycarbonyl-diethylphosphono)-methyl-3-azido-4-(2'-oxo)-propyloxy-2-azetidinone 1.30 g. of 1-(benzyloxycarbonyl-diethylphosphono)-methyl-3-azido-4-chloro-2-acetidinone is dissolved in 8.5 ml. of methylene chloride followed by adding 0.8 ml. of freshly distilled hydroxy acetone. The reaction mixture is stirred room temperature for 10 minutes under $N_2$. To the solution is added a mixture of 383.0 mg. of $Ag_2O$, and 766.0 mg. of silver fluoroborate, and the mixture is stirred for 0.5 hr. at room temperature under $N_2$. The reaction mixture is then diluted with $CH_2Cl_2$ and filtered through supercel. The filtrate is then evaporated in vacuo, and the residue is taken up in benzene and washed 3 times with pH 7 phosphate buffer. The organic layer is dried over magnesium sulfate and evaporated to give 847.5 mg. of crude 1-(benzyloxycarbonyldiethylphosphono)-methyl-3-azido-4-(2'-oxo)-propyloxy-2-azetidinone. Chromatography on silica gel (60 g.) using 1:1 EtOAc/ benzene as eluant gives 508.1 mg. of pure 1-(benzyloxycarbonyl-diethylphosphono)-methyl-3-azido4-(2'-oxo)-propyloxy-2-acetidinone as a mixture of cis and trans isomers. IR film$\lambda$: 4.70$\mu$ (azido); 5.60$\mu$ ($\beta$-lactam); 5.72 (benzyl ester). NMR (CDCl$_3$)$\delta$: 7.33, s (C$_6$H$_5$); 5.25, s (C$\underline{H}_2$—C$_6$H$_5$); 4.35–4.50 multiple (H$_3$ and H$_4$); 2.13, s (C$\underline{H}_3$), and the other isomer showes 2.5, s (C$\underline{H}_3$); 1.26, m, (C$\underline{H}_3$—CH$_2$—O).

STEP C

Benzyl d,l-7$\beta$-azido-3-methyl-1-oxa-dethiaceph-3-em-4-carboxylate

Sodium hydride (94.5 mg. of a 57% dispersion in mineral oil) is added to a solution of isomeric 1-(benzyloxycarbonyl-diethylphoshono)-methyl-3-azido-4-(2-oxo)-propyloxy-2-acetidinones (350 mg.) in anhydrous benzene (10 ml.). The mixture is stirred under nitrogen for 2¼ hrs. at 62°. The reaction mixture is cooled, diluted with benzene, and washed with pH 2 phosphate buffer, water, pH 9 phosphate buffer, water, and brine. The organic layer is dried with magnesium sulfate, filtered, and evaporated in vacuo to crude product (176.5 mg.). This is purified by preparative layer chromatography on silica gel using 95:5 (cyclohexane-isopropanol) as developing solvent to give benzyl d,l-7$\beta$-azido-3-methyl-1-oxadethiaceph-3-em-4-carboxylate, 91.9 mg., and the 7$\alpha$-azidoisomer in 61.6 mg. quantity. IR (film)$\lambda$: 4.70$\mu$ (azido), 5.58 ($\beta$-lactam), 5.89$\mu$ (benzyl ester). NMR (CDCl$_3$) $\delta$: 7.40 (C$_6$H$_5$); 5.25, s, (C$\underline{H}_2$—$\phi$), 5.1, d, (J=5 cps, H$_7$), 4.58, d, (J=5 cps, H$_6$), 4.40 d, (O—C$\underline{H}_2$), 2.06 s, (CH$_3$). M$^+$ (Calc. 314.29) Found 314.29-N$_2$.

STEP D

Benzyl d,l-7$\beta$-amino-3-methyl-1-oxa-dethiaceph-3-em-4-carboxylate

Hydrogen sulfide is slowly bubbled into an ice-cold solution of benzyl d,l-7$\beta$-azido-3-methyl-1-oxa-dethiaceph-3-em-4-carboxylate (91.9 mg.) and triethylamine (161 $\mu$l. ) in 2 ml. of chloroform over 25 minutes. The mixture is diluted with chloroform, washed with water, pH 3 phosphate buffer, water, and brine, dried over magnesium sulfate, filtered, and evaporated in vacuo to provide crude benzyl d,l-7$\beta$-amino-3-methyl-1-oxa-dethiaceph-3-em-4-carboxylate (94.0 mg.). IR (film)$\lambda$: 5.62 $\mu$ ($\beta$-lactam), 5.79$\mu$ (ester). NMR (CDCl$_3$)$\delta$: 7.40 (C$_6$H$_5$), 5.25 s, (CH$_2$-$\phi$), 5–4.58 m (H$_6$ and H$_7$), 4.40 d, (OCH$_2$), 2.06 s (CH$_3$).

STEP E

Benzyl d,l-7$\beta$-(D-$\alpha$-azido-phenylacetamido)-3-methyl-1-oxadethiaceph-3-em-4-carboxylate D-$\alpha$-azidophenylacetic acid (72 mg.) is added to a solution of benzyl d,l-7$\beta$-amino-3-methyl-1-oxadethiaceph-3-em-4-carboxylate (94.0 mg.) in anhydrous CH$_2$Cl$_2$ (2 ml.) and the resulting solution is stirred under nitrogen at 0°–5° for 5 minutes.

Dicyclohexylcarbodiimide (76.3 mg.) in 2 ml. of dry methylene chloride is then added to the reaction mixture and stirring continued overnight at 15°-20°. The precipitate of dicyclohexyl urea is filtered off and washed with three portions of methylene chloride. The combined filtrate and washings is washed with water, 5% sodium bicarbonate, water and brine, dried with magnesium sulfate, filtered and evaporated in vacuo. The residue (184.0 mg.) is purified by silica gel preparative layer chromatography using 5:1 cyclohexane-isopropanol as developing solvent to yield benzyl d,l-7$\beta$-(D-$\alpha$-azidophenylacetamido)-3-methyl-1-oxadethiaceph-3-em-4-carboxylate (39 mg.). IR (film)$\lambda$: 2.98 (NH), 4.71$\mu$ (N$_3$), 5.57 ($\beta$-lactam), 5.82 ester, 5.91 and 6.4 (amide). NMR (CDCl$_3$)$\delta$: 7.23 s ($\phi$), 5.53 m (H$_7$), 5.21 m, (CH$_2\phi$), 5.05 d (J=5, H$_6$), 5.03 and 4.95 (two singlets, diastereomeric C$\underline{H}$N$_3$), 2.03 s (CH$_3$).

STEP F d,l-7$\beta$-(D-$\alpha$-amino-phenylacetamido)-3-methyl-1-oxadethiaceph-3-em-4-carboxylic acid A mixture of benzyl d,l-7$\beta$-(D-$\alpha$-azido-phenylacetamido)-3-methyl-1-oxadethiaceph-3-em-4-carboxylate (39.0 mg.), 10% palladium on charcoal (39.0 mg.), methanol (6 ml.) and water (1 ml.) is hydrogenated at 45 psi for 1¼ hrs. at room temperature. The catalyst is filtered off and washed with water and methanol (4 times). The combined filtrate and washings is evaporated in vacuo to remve methanol, and then lyophilized to afford d,l-7$\beta$-(d-$\alpha$-amino-phenylacetamido)-3-methyl-1-oxadethiaceph-3-em-4-carboxylic acid in 7.0 mg. as an amorphous material. IR (Nj)$\lambda$=2.8–3.0$\mu$ (broad NH); 5.6 ($\beta$-lactam). NMR (D$_2$O)$\delta$: 7.49 s ($\phi$), 4.89 and 5.29 (two singlets diastereomeric); 3,85 m, (H$_6$), and 1.78 s (CH$_3$).

EXAMPLE 124 d,l-7$\beta$-(D-$\alpha$-amino-phenylacetamido)-3-methyl-1-methylene-dethiaceph-3-em-4-carboxylic acid

STEP A

5-Ethylenedioxy-1-hexene

A mixture of 5-oxy-1-hexene (9.8 g.), ethylene glycol (18.6 g.), p-toluene sulfonic acid monohydrate (1.56 g.) and benzene (250 ml.) is heated at reflux under a Dean-Stark water separator. After 2 hrs., the reaction mixture is washed with water and the organic layer is separated, dried with magnesium, and evaporated in vacuo. Distillation of the residue gives 5-ethylenedioxy-1-hexene (90% yield) b.p. 34°–37°/1.5 mm. nmr (CDCl$_3$)$\delta$: 1.27 (s, CH$_3$), 1.5–2.4 (m, CH$_2$—CH$_2$); 2.83 (s, —O—CH$_2$—CH$_2$—O); 4.80–6.1 (m, CH$_2$=CH—). IR (film)$\mu$: 6.06 (CH$_2$=CH—).

STEP B

4-Ethylenedioxy-pentanal

A mixture of 5-ethylenedioxy-1-hexene (6.0 g.), osmium tetroxide (0.5 g.), ether (150 ml.) and water (150 ml.) is treated portionwise with sodium metaperiodate (19.3 g.) so that the reaction temperature does not exceed 30°. After the addition of the periodate, a voluminous white solid precipitates out. The mixture is stirred 2.5 hrs. at room temperature, then filtered, and the solid portion is washed with more aqueous ether. The aqueous portion of the filtrate is separated and extracted with three portions of methylene chloride. The combined organic phases are dried with magnesium sulfate, filtered, and evaporated in vacuo. Distillation of the residue yields 4-ethylenedioxy-pentanal (65% yield) b.p. 56°–58°/10.5 mm nmr (CDCl$_3$)δ: 1.27 (s, CH$_3$), 2.04–2.80 (m, —CH$_2$—CH$_2$—); 3.9 (s, —OCH$_2$—CH$_2$—O), 9.73 (t, O=C—H). IR (film) μ: 3.66; 3.79.

STEP C

Benzyl N-(4-ethylenedioxy)pentylidene-α-amino-diethylphosphonoacetate

Anhydrous magnesium sulfate (9.5 g.) is added to a solution of benzyl α-amino-diethylphosphonacetate (1.86 g.) in anhydrous ether (90 ml.) and the resulting mixture is stirred at room temperature for 15 mins. A solution of 4-ethylenedioxy-pentanal (0.83 g.) in anhydrous ether (90 ml.) is then added and the resulting mixture is stirred overnight under nitrogen at room temperature. The mixture is filtered and the filtrate evaporated in vacuo to give benzyl N-(4-ethylenedioxy)pentylidene-α-amino-diethylphosphonoacetate (2.54 g.) as an oil. NMR (CDCl$_3$)δ: 1.33 (s, CH$_3$), 1.32 (m, O—CH$_2$—C$\underline{H}$$_3$) 3.93 (s, —O—CH$_2$—CH$_2$—O); 4.1 (m, OC$\underline{H}$$_2$CH$_3$); 4.5 (d, J=20 Hz; HC-P); 5.27 (s, OC$\underline{H}$$_2$φ); 7.37 (φ); 7.83 (d,d —HC=N—). IR (film) μ: 5.72 (CO$_2$CH$_2$φ); 6.05 (C=N—).

STEP D cis-1-(Benzyloxycarbonyldiethylphosphono)methyl-3-azido-4-(3-ethylenedioxybutyl)-2-azetidinone A solution of azidoacetyl chloride (1.05 ml.) in anhydrous cyclohexane (120 ml.) is added dropwise over 1.5 hrs. to a stirring solution of benzyl N-(4-ethylenedioxy)-pentylidene-α-amino-diethylphosphonoacetate (2.54 g.) and triethylamine (1.68 mls.) in anhydrous 1:1 cyclohexane-benzene. The resulting mixture is dilute with benzene and washed two times with water, two times with pH 3 phosphate buffer, two times with water, once with pH 9 phosphate buffer, two times with water, and finally two times with brine. The organic layer is dried with magnesium sulfate, filtered, and evaporated in vacuo. The crude β-lactam (3.04 g.) is purified by column chromatography on EM silica gel using 1:1 benzene-ethyl acetate as eluting solvent to give pure cis-1-(benzyloxycarbonyldiethylphosphono)methyl-3-azido-4-(3-ethylenedioxybutyl)-2-azetidinone (0.98 g.) as an oil. NMR (CDCl$_3$) δ: 1.29 (s, CH$_3$); 1.30 (m, O—CH$_2$—C$\underline{H}$$_3$); 3.93 (s, OCH$_2$CH$_2$O) <4.1 (m, OC$\underline{H}$$_2$CH$_3$ and H4); 4.72 (d, J=5.5 Hz, H3); 4.5 (d, J=20 cps, HC—P); 5.27 (s, OC$\underline{H}$$_2$φ); 7.35 (φ). IR (film) mμ: 4.70 (N$_3$); 5.62 (β-lcatam); 5.72 (benzyl ester).

STEP E cis-1-(Benzyloxycarbonyldiethylphosphono)methyl-3-azido-4-(3-oxobutyl)-2-azetidinone A suspension of cis-1-(benzyloxycarbonyldiethylphosphono)-methyl-3-azido-4-(3-ethylenedioxybutyl)-2-azetidinone (0.10 g.) in 10% aqueous sulfuric acid (8 ml.) and glacial acetic acid (1 ml.) is heated with stirring at 50° for 2 hrs. The mixture is cooled to room temperature and extracted with methylene chloride (3×15 ml.) The combined extracts are washed with brine (2×10 ml.), dried with magnesium sulfate, filtered, and evaporated in vacuo to yield 60% of cis-1-(benzyloxycarbonyldiethylphosphono)methyl-3-azido-4-(3-oxobutyl)-2-azetidinone as a light brown oil. NMR (CDCl$_3$)δ: 1.27 (m, O—CH$_2$—C$\underline{H}$$_3$); 2.13 (s, CH$_3$), 4.12 (m, O—C$\underline{H}$$_2$CH$_3$ and H4); 4.72 (d, J=5.5 Hz, H3); 5.23 (s, OCH$_2$φ); 7.35 (φ). IR (film) μ: 4.70 (N$_3$); 5.61 (β-lactam); 5.70 (ester); 5.82 (C=O) M+ (Calc. 466) Found 466.

STEP F

Benzyl d,l-7β-azido-3-methyl-1-methylene-dethiaceph-3-em-4-carboxylate.

Sodium hydride (127 mg. of a 57% dispersion in mineral oil) is added to a solution of cis-1-(benzyloxycarbonyldiethylphosphono)-methyl-3-azido-4-(3-oxybutyl)-2-azetidinone (523 mg.) in anhydrous benzene (12 ml.). The mixture is stirred under nitrogen for 15 min. at room temperature and then at 68°–69° for 5 hrs. The reaction mixture is cooled, diluted with benzene, and washed with pH 2 phosphate buffer, water, pH 9 phosphate buffer, water and brine. The organic layer is dried with magnesium sulfate, filtered, and evaporated in vacuo to a crude produdct (200 mg.). This is purified by preparative layer chromatography on silica gel using 3:1 cyclohexane-isopropanol as developing solvent to afford benzyl d,l-7β-azido-3-methyl-1-methylene-dethiaceph-3-em-4-carboxylate (159 mg.) as an oil. NMR (CDCl$_3$)δ: 2.05 (s, CH$_3$), 3.72 (m, H6); 4.86 (d, J=5 cps, H7); 5.25 (s, C$\underline{H}$$_2$φ); 7.40 (φ). IR (film) μ: 4.71 (N$_3$); 5.61 (β-lactam); 5.79 (ester); 6.11 (C=C); M+ (Calc. 312) Found 312.

STEP G

Benzyl d,l-7β-amino-3-methyl-1-methylene-dethiaceph-3-em-4-carboxylate

Hydrogen sulfide is slowly bubbled into an ice-cold solution of benzyl d,l-7β-azido-3-methyl-1-methylene-dethiaceph-3-em-4-carboxylate (200 mg.) and triethylamine (177 μl.) in chloroform (8 ml.) for 15 mins. The mixture is diluted with more chloroform, washed with water, pH 3 phospahte buffer, water, and brine, dried over magnesium sulfate, filtered, and evaporated in vacuo to provide crude benzyl d,l-7β-amino-3-methyl-1-methylene-dethiaceph-3-em-4-carboxylate (200 mg.). NMR (CDCl$_3$)δ: 2.05 (s, CH$_3$); 3.72 (m, H6); 4.86 (d, J=5 Hz, H7); 5.25 (s, CH$_2$φ); 7.40 (φ). IR (film) μ: 2.94 (NH$_2$); 5.62 (β-lactam); 5.82 (ester).

STEP H

Benzyl d,l-7β-(D-α-azido-phenylacetamido)-3-methyl-1-methylenedethiaceph-3-em-4-carboxylate D-α-Azidophenylacetic acid (124 mg.) is added to a solution of benzyl d,l-7β-amino-3-methyl-1-methylene-dethiaceph-3-em-4-carboxylate (200 mg.) in anhydrous methylene chloride (0 ml.) and the resulting solution is stirred under nitrogen at 0°–5° for 5 mins. Dicyclohexylcarbodiimide (144 mg.) is then added to the reaction mixture and stirring is continued overnight at 15°–20°. The precipitate of dicyclohexyl urea is filtered off and washed with three portions of methylene chloride. The combined filtrate and washings is washed with water, 5% sodium bicarbonate, water, and brine, dried with magnesium sulfate, filtered, and evaporated in vacuo. The residue (327 mg.) is purified by silica gel preparative layer chromatography using 4:1 cyclohexane-isopropanol as developing solvent to yield benzyl d,l-7β-(D-α-azidophenylacetamido)-3-methyl1-methylene-dethiaceph-3-em-4-carboxylate (178 mg.) as an oil. NMR (CDCl$_3$)δ: 2.03 (s, CH$_3$); 3.75 (m, H6); 4.95 and 5.03 (two singlets, diastereomeric CHN$_3$); 5.21 (m, CH$_2$φ and H7); 7.23 (s, 100). IR (film)μ3.0 (NH), 4.71 (N$_3$); 5.65 (β-lactam); 5.82 (ester); 5.92, 6.48 (amide). M+ (Calc. 445), Found 445.

STEP I d,l-7β-(D-α-Amino-phenylacetamido)-3-methyl-1-methylene-dethiaceph-3-em-4-carboxylic acid A mixture of benzyl d,l-7β-(D-α-azidophenylacetamido)-3-methyl-1-methylene-dethiaceph-3-em-4-carboxylate (119 mg.), 10% palladium on carbon (119 mg.), methanol (10 ml.), water (5 ml.) and glacial acetic acid (1 drop) is hydrogenated at 45 psi for 1.5 hrs. at room temperature. The catalyst is filtered off and washed with water (4×2 ml.). The combined filtrate and washings is evaporated in vacuo to remove methanol and then lyophilized to afford d,l-7β-(D-α-aminophenylacetamido)-3-methyl-1-methylene-dethiaceph-3-em-4-carboxylic acid (48 mg.) as an amorphous solid. NMR (D$_2$O) δ: 1.78 (s, CH$_3$); 3.85 (m, H6); 4.89 and 5.29 (two singlets, diastereomeric CHNH$_2$; 7.49 (s, φ). IR (film) μ: 2.8–3.0 (broad NH$_2$); 5.56 (β-lactam); 6.4 (carboxylate). UV (pH 7 buffer) λ max 257 (E$^1$ %=187)nm.

EXAMPLE 125

Sodium d,l-7α-methoxy7-(2-thienylacetamido)-3-carbamoyloxymethyl1-oxa-dethiaceph-3-em-4-carboxylate To a 1 dram vial equipped with magnetic stirrer is added sodium d,l-7α-methoxy-7-(2-thienylacetamido)-1-oxadethia-cephalosporanate (91.0 mg.) and citrus acetyl esterase (2.6 ml.). The initial pH of 7.8 is adjusted to pH 6.7 with dilute phosphoric acid, and then maintained at pH 6.7 by addition of 1 N NaOH. After 8.5 hrs. at 30°, the addition of base is slow and the reaction is stopped. The mixture is cooled to room temperature, and then treated with powdered sodium chloride (900 mg.), and stirred. The resulting thin suspension is cooled to 0°, overlaid with 6 ml. of ethyl acetate, the pH brought to 2.3 with 5% phosphoric acid. The layers are separated. The aqueous portion is extracted with more ethyl acetate (3×4 ml.). The combined ethyl acetate solution is dried over magnesium sulfate, filtered, and evaporated i.v. to yield d,l-7α-methoxy-7-(2-thienylacetamido)-3-hydroxymethyl-1-oxa-dethicaeph-3-em-4-carboxylic acid (55.1 mg.) as a yellow foam.

The above free acid is immediately dissolved in anhydrous tetrahydrofuran (3.0 ml.) and the solution cooled to −78° (dry ice-acetone) under N$_2$. Chlorosulfonyl isocyanate (15 μl.) is added via syringe. The resulting solution is stirred at −78° for 2.5 hrs., and then treated with 0.1 M pH 7 phosphate buffer (0.6 ml.) at −40°. The THF is evaporated i.v., the aqueous residue is treated with 0.1M pH 7 phosphate buffer (2 ml.) and EtOAc (4 ml.). The pH of aqueous layer is 2.2. The mixture is rapidly stirred for 1 hr. at room temperature. The pH of aqueous layer is brought to pH 8 with 5% aqueous Na$_3$PO$_4$. The organic layer is separated and washed 2 times with 0.1 M pH 7 phosphate (4 ml.). The combined aqueous layers are acidified to pH 2.2 with 5% phosphoric acid, and the extracted with ethyl acetate (2×10 ml.). The combined ethyl acetate solution is washed with brine, dried over MgSO$_4$, and evaporated in vacuo to yield d,l-7α-methoxy-7-(2-thienylacetamido)-3-carbamoyloxymethyl-1-oxa-dethiaceph-3-em-4-carboxylic acid as a pale yellow foam (30.0 mg.). NMR

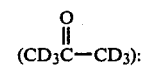

δ 7.2–6.97 m (aromatic & NH protons), 5.09–4.92

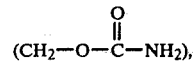

4.6 and 4.5 (H$_2$ and H$_6$), 3.82

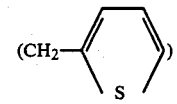

and 3.3 (7-OCH$_3$).

The free acid is dissolved in 10 ml. of water containing 6.4 mg. of sodium bicarbonate. The mixture is filtered, and the filtrate lyophilized to give 17.1 mg. of sodium d,l-7α-methoxy-7-(2-thienylacetamido)-3-carbamoyloxymethyl- 1-oxa-dethiaceph-3-em-4-carboxylate. NMR (D$_2$O)δ 7.2–6.97 m (aromatic protons), 5.09–4.92

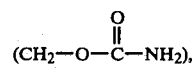

4.6 and 4.5 (H$_2$ and H$_6$), 3.82

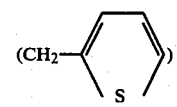

and 3.3 (OCH$_3$). UV (pH 7 buffer) λ max 230 (ε9100) and 260 (ε4600) nm.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lowwer alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric, hydrobromic, sulfuric, nitric, toluene-p-sulphonic and methane sulphonic acids may also be employed.

The salts can be mono-salts such as the monosodium salt obtained by treating one equivalent of sodium hydroxide with one equivalent of the product (I), also mixed di-salts may be obtained by treating one equivalent of a mono-salt with one equivalent of a different base. Alternatively, salts may be obtained by treating one equivalent of a base having a divalent cation, such as calcium hydroxide, with one equivalent of the product (I). In addition, mixed salts and esters such as those obtained by treating the product (I) with one equivalent of sodium hydroxide and then with one equivalent of lactic acid are also within the scope of this invention.

The salts of this invention are pharmacologically acceptable nontoxic derivatives which can be used as the active ingredient in suitable unit-dosage pharmaceutical forms. Also, they may be combined with other drugs to provide compositions having a broad spectrum of activity. In addition, the instant salts and, also, the corresponding ester and amide derivatives, have utility as intermediates in preparing the carboxylic acid product illustrated by formula I, supra.

The compounds of Formula I are free acids, i.e., having a carboxylic acid group at position 4. In addition to salts, the scope of this invention contemplates equally the preparation of various esters of this carboxylic acid functionality. Examples of suitable derivatives that might be mentioned are esters of alcohols, phenols, mercaptans, and thiophenols. for example, esters of interest are the compounds of Formula I having the following group at the 4-position: —COXR$^1$ wherein X is oxygen or sulfur, and R$^1$ can be alkyl having 1–10 carbon atoms, straight or branched, such as methyl, ethyl, t-btuyl, pentyl, decyl, etc.; carbonylmethyl including phenacyl, p-bromophenacyl, p-t-butylphenacyl, acetoxyacetylmethyl, pivaloxyacetylmethyl, carboxymethyl and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1–10 and preferably 1–6 carbon atoms, but can be branched, straight, or cyclic, and the alkyl portion has 1–6 carbon atoms, such as methoxymethyl, ethoxymethyl, isopropoxymethyl, decyloxymethyl, ethoxypropyl, decyloxypentyl, cyclohexyloxymethyl, etc.; alkanoyloxyalkyl wherein the alkanoyloxy portion is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, etc.; haloalkyl wherein halo is chloro, bromo, fluoro, or iodo, and the alkyl portion is straight or branched having 1–6 carbon atoms, e.g., 2,2,2-trichloroethyl, trifluoroethyl, 2-bromopropyl, diiodomethyl, 2-chloroethyl, 2-bromoethyl, etc.; alkenyl having 1–10 carbon atoms, wither straight or branched, e.g., allyl, 2-propenyl, 3-butenyl, 4-butenyl, 4-pentenyl, 2-butenyl, 3-pentenyl, 3-methyl-3-butenyl, methanallyl, 1,4-cyclohexadien-1-methyl, etc.; alkynyl having 1–10 carbon atoms, either straight or branched, e.g., 3-pentynyl, propargyl, ethynyl, 3-butyn-1-yl, etc.; alkanoyl, either straight or branched, having 1–10 carbon atoms, such as pivaloyl, acetyl, propionyl, etc.; aralkyl or heteroaralkyl wherein alkyl has 1–3 carbon atoms, and hetero means 1–4 hetero atoms being O, S, or S, such as benzyl, benzhydryl, and substituted benzyl or benzhydryl, e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinemethyl, 5-phenylthio-1-tetrazolylmethyl, or the like (the use of the terms lower alkyl or loweralkoxy in this context means 1–4 carbon atom chain); or phthalidyl; or phenylethyl, 2-(p-methylphenyl)ethyl, and the arylthioalkyl analogues; aryloxyalkyl wherein aryl is preferably a phenyl ring having 0–3 substituents, preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)-phenoxymethyl, (4-methoxy)phenylthiomethyl, (4-chloro)phenylthiomethyl, phenylthioethyl; aryl wherein aryl is phenyl, 5-indanyl, or substituted phenyl having 0–3 substituents, preferably 0 or 1 sutstituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)benzyloxymethyl, (4-chloro)benzyloxymethyl; alkylthioalkyl wherein the alkylthio portion has 1–10 and preferably 1–6 carbon atoms, but can be branched, straight, or cyclic, and the alkyl portion has 1–6 carbon atoms, such as methylthioethyl, ethylthioethyl, cyclohexylthiomethyl, decylthiobutyl, methylthiopropyl, isopropylthioethyl, methylthiobutyl, etc.

In addition to the esters listed above, amides can also be employed, i.e., wherein X is the

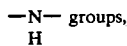 groups, and $R^1$ is as defined.

Particularly preferred esters are those wherein IX is oxygen and $R^1$ is aralkyl, aryloxyalkyl, aralkoxyalkyl, alkylthioalkyl, haloalkyl, or alkenyl.

Methods for the preparation of the esters andd amide derivatives include the reaction of the carboxylic acid product (I) or corresponding acid halide with an alcohol or phenol, for example, methanol, ethanol, cyclohexanol, phenol, benzyl alcohol, dibenzhydrol and the like. The amide derivatives may be obtained by treating the corresponding acid halide with ammonia or with an appropriate alkylamine, dialkylamine, aralkylamine or heterocyclic amine. These and other conventional methods for the preparation of the esters and amides will be obvious to those skilled in the art.

It will be apparent from a further reading of this application that in many of the chemical reactions described, the cephalosporin is blocked at position 4 by a so-called "easily removable blocking group." Many of these groups are contained within the above definition of the chain —$COXR^1$.

In this connection, it is noted that preferred "blocking groups" include the sub-generic groups defined above as aralkyl, haloalkyl, alkanoyloxyalkyl, alkoxyalkyl, alkenyl, substitiuted alkyl, or aralkoxyalkyl, and also including alkylsilyl, wherein alkyl has 1–10 carbon atoms.

More specifically, preferred "blocking groups" including benzyl, phenacyl, methoxymethyl, trichloreothyl, trimethylsilyl, tributyltin, p-methoxybenzyl, benzhydryl. These blocking groups are preferred since they are generally recognized easily-removable blocking groups in cephalosporin and penicillin art. Although we describe procedures for the removal of these blocking groups, such processes are considered within the skill of those in the art.

Thus the novel cephalosporins are valuable antimicrobial substances which are active against various gram-positive and gram-negative pathogens such as *Bacillus subtilis, Salmonella schottmuelleri* and *Proteus vulgaris*. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups elixirs and the like which can be prepared in accordance with procedures well known in this art.

The novel cephalosporins are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus*. The antibacterial cephalosporins of the invention may further be utilized as additives to animal feeding stuffs, for preserving foodstuffs and as disinfectants. For example, they may be employed in aqueous compositions in concentrations ranging form 0.1 to 10 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum sterate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oil or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid from, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary prepartion in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The examples which follow illustrate the methods by which the products of this invention may be obtained. however, the examples are illustrative only and it should be apparent to one having ordinary skill in the art that this invention includes the functionally equivalent products and methods for their preparation. Therefore, any modification of the synthesis described herein which results in the formation of an identical product should be construed as constituting an analogous method. The claimed process is capable of wide variation and modification and any minor departure or extension is considered as being within the skill of the artisan and as falling within the scope of this invention.

What is claimed is:

1. A compound of the formula:

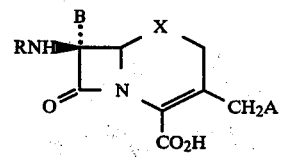

and its isomers wherein R is a carboxylic acyl radical; B is H, OCH₃, CH₃ or SR″ wherein R″ is lower alkyl of 1–6 carbons and phenyl; A is azido, halo, cyano, quaternary ammonium, hydroxy, carbamoyloxy, N-lower alkyl carbamoyloxy, N,N-di-lower alkyl carbamoyloxy, amino mercapto, lower alkylthio, lowe alkanoyloxy, aroyloxy or a 5-membered heterocyclic thio radical selected from the group consisting of 1-methyltetrazolylthio and 2-methyl-1,3,4-thiadiazolylthio; X is —O— and non-toxic pharmacologically acceptable salts, esters and amides thereof.

2. The compound according to claim 1 wherein R is of the formula:

wherein R³ is phenyl, thienyl, furyl, tetrazolyl, or

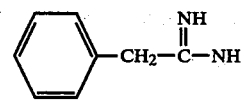

and R² is hydrogen, halo, amino, guanidino, phosphono, hydroxy, tetrazolyl, carboxyl, sulfo or sulfamino.

3. A compound accroding to claim 2 wherein R² is hydrogen, amino or carboxyl;
R³ is phenyl, thienyl, furyl or tetrazolyl; and
A is lower alkanoyloxy, carbamoyloxy, pyridinium, 1-methyl tetrazolylthio, or 2-methyl-1,3,4-thiadiazolylthio.

4. A compound according to claim 2 wherein the radical

is 2-thienylacetyl, 2-furylacetyl, 3-thienylacetyl, 1-tetrazolylacetyl, D-phenylglycyl, phenylmalonyl, 3-thienylmalonyl, or α-hydroxyphenylacetyl; and A is acetoxy, carbamoyloxy, 1-methyltetrazolylthio, 2-methyl-1,3,4-thiadiazolylthio, or pyridinium.

5. A compound of claim 4 which is d,1-7α-methoxy-7-(2-thienylacetamido)-1-oxadethia-cephalosporanic acid.

6. A compoundof claim 4 which is d,1-7α-methoxy-7-(2-thienylacetamido)-3-carbamoyloxymethyl-1-oxadethiaceph-3-em-4-carboxylic acid.

7. A compound of claim 4 which is sodium 7β-(2′-thienylacetamido)-1-oxa-1-dethiacephalosporanate.

8. A compound of claim 4 which is 7β- (2-thienylacetamido)-1-oxadethiacephalosporanic acid.

9. A compound of claim 2 which is 7β- (2-tetrazolylacetamido)-3-(2-methyl-1,3,4-thiadiazolyl-5-thiomethyl)-1-oxadethiacephalosporanic acid.

10. A process for preparing a compound of the formula:

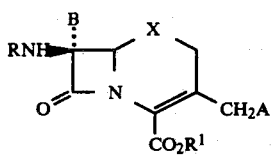

wherein

R is a carboxylic acyl radical;

B is H, CH₃, OCH₃ or SR wherein R is lower alkyl of 1-6 carbon atoms or phenyl;

$R^1$ is hydrogen or a protecting group;

A is azido, halo, cyano, quaternary ammonium, hydroxy, carbamoyloxy, N-loweralkyl carbamoyloxy, N,N-di-lower alkyl carbamoyloxy, amino, mercapto, lower alkylthio, lower alkanoyloxy, aroyloxy or a 5-membered heterocyclic thio radical selected from the group consisting of 1-methyltetrazolylthio and 2-methyl-1,3,4-thiadiazolylthio; and X is —O— which comprises treating a compound of the formula:

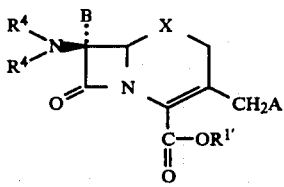

wherein

X and A are as defined above;

$R^{1'}$ is a blocking group;

$R^4$ is hydrogen or both $R^4$ are joined to form a benzylidene with an acylating agent; and removal of said blocking group to form the free acid.

11. A compound of the formula:

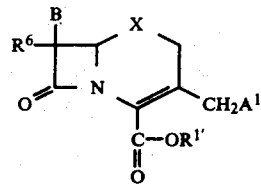

wherein B is H, CH₃, OCH₃ or SR wherein R is lower alkyl of 1-6 carbon atoms or phenyl; $A^1$ is azido, halo, cyano, quaternary ammonium, hydroxy, carbamoyloxy, N-loweralkyl carbamoyloxy, N,N-di-lower aljyl carbamoyloxy, amino, mercapto, lower alkylthio, lower alkyanoyloxy, aroyloxy or a 5-membered heterocyclic thio radical selected from the group consisting of 1-methyltetrazolylthio andd 2-methyl-1,3,4-thiadiazolylthio;

$R^{1'}$ is H or a protecting group;

X is —O—,; and $R^6$ is azido, amino, or a benzaldimino.

12. A compound according to claim 11 wherein $R^6$ is 7β-amino.

13. A compound accroding to claim 12 wherein B is -CH₃.

14. Acompound according to claim 12 wherein B is —OCH₃.

15. A compound according to claims 1 and 18 wherein R is:

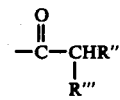

wherein R''' is selected from the group consisting of amino, hydroxy, azido, carbamoyl, guanidino, halo, sulfamino, tetrazolyl, sulfo, carboxy, and carbalkoxy; and R'' is substituted and unsubstituted aryl wherein the aryl is phenyl and wherein the substituent is selected from the group consisting of OH, SH, halo, cyano, carboxy, sulfamino, carbamoyl, sulfonyl, azido, amino and guanidino.

16. A method of treatment comprising administering an antibiotically effective amount of a compound according to claim 1.

17. An antibiotic pharmaceutical composition comprising a therapeutically effective amount of a compound according to claim 1 and a pharmaceutically acceptable carrier.

18. A compound according to claim 1 wherein B is —OCH₃.

19. A compound of claim 4 which is 7β-(D-2-phenyl-2-hydroxyacetamido)-3-(5-(1-methyl-1,2,3,4-tetrazolyl)-thio)methyl-1-oxadethio-decephalosporanic acid.

* * * * *